(12) United States Patent
Benny-Ratsaby et al.

(10) Patent No.: US 9,782,489 B2
(45) Date of Patent: *Oct. 10, 2017

(54) METAP-2 INHIBITOR POLYMERSOMES FOR THERAPEUTIC ADMINISTRATION

(71) Applicant: CHILDREN'S MEDICAL CENTER CORPORATION, Boston, MA (US)

(72) Inventors: Ofra Benny-Ratsaby, Jerusalem (IL); Robert D'Amato, Lexington, MA (US); Takeru Yoshimura, Boston, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/248,043

(22) Filed: Aug. 26, 2016

(65) Prior Publication Data

US 2016/0361428 A1 Dec. 15, 2016

Related U.S. Application Data

(63) Continuation of application No. 14/313,020, filed on Jun. 24, 2014, now Pat. No. 9,446,140, which is a continuation of application No. 12/648,155, filed on Dec. 28, 2009, now Pat. No. 8,790,634, which is a continuation-in-part of application No. PCT/US2008/068367, filed on Jun. 26, 2008.

(60) Provisional application No. 61/054,595, filed on May 20, 2008, provisional application No. 60/937,198, filed on Jun. 26, 2007.

(51) Int. Cl.
| | |
|---|---|
| A61K 47/48 | (2006.01) |
| A61K 31/77 | (2006.01) |
| A61K 31/336 | (2006.01) |
| A61K 9/00 | (2006.01) |
| A61K 9/107 | (2006.01) |

(52) U.S. Cl.
CPC ...... *A61K 47/48215* (2013.01); *A61K 9/0053* (2013.01); *A61K 9/107* (2013.01); *A61K 9/1075* (2013.01); *A61K 31/336* (2013.01); *A61K 47/482* (2013.01); *A61K 47/488* (2013.01); *A61K 47/4883* (2013.01)

(58) Field of Classification Search
None
See application file for complete search history.

(56) References Cited

U.S. PATENT DOCUMENTS

| | | | |
|---|---|---|---|
| 5,190,989 A | 3/1993 | Himori | |
| 5,384,333 A | 1/1995 | Davis et al. | |
| 5,593,658 A | 1/1997 | Bogdanov et al. | |
| 5,693,751 A | 12/1997 | Sakurai et al. | |
| 6,548,477 B1 | 4/2003 | Olson et al. | |
| 6,592,899 B2 | 7/2003 | Fowers et al. | |
| 6,623,729 B2 | 9/2003 | Park et al. | |
| 6,919,307 B2 | 7/2005 | Olson et al. | |
| 6,949,620 B2 | 9/2005 | Aida et al. | |
| 7,037,890 B2 | 5/2006 | Olson et al. | |
| 7,084,108 B2 | 8/2006 | Olson et al. | |
| 7,087,768 B2 | 8/2006 | Han et al. | |
| 7,105,482 B2 | 9/2006 | Olson et al. | |
| 7,157,420 B2 | 1/2007 | Olson et al. | |
| 7,268,111 B2 | 9/2007 | Olson et al. | |
| 7,304,082 B2 | 12/2007 | Marino, Jr. et al. | |
| 7,332,523 B2 | 2/2008 | Satchi-Fainaro et al. | |
| 7,348,307 B2 | 3/2008 | Olson et al. | |
| 2002/0151493 A1 | 10/2002 | Olson et al. | |
| 2002/0193298 A1 | 12/2002 | Olson et al. | |
| 2003/0017131 A1 | 1/2003 | Park et al. | |
| 2003/0109671 A1 | 6/2003 | Olson et al. | |
| 2004/0242681 A1 | 12/2004 | Han et al. | |
| 2004/0265917 A1 | 12/2004 | Benjamin et al. | |
| 2005/0014737 A1 | 1/2005 | Agoston et al. | |
| 2005/0059585 A1 | 3/2005 | Olson et al. | |
| 2005/0175665 A1 | 8/2005 | Hunter et al. | |
| 2005/0239878 A1 | 10/2005 | Thompson et al. | |
| 2006/0069028 A1 | 3/2006 | Olson et al. | |
| 2006/0223758 A1 | 10/2006 | Olson et al. | |
| 2007/0010452 A1 | 1/2007 | Olson et al. | |
| 2007/0117758 A1 | 5/2007 | Olson et al. | |
| 2007/0161570 A1 | 7/2007 | Olson et al. | |

(Continued)

FOREIGN PATENT DOCUMENTS

| | | |
|---|---|---|
| CN | 101 336 890 | 1/2009 |
| WO | 03/027104 A1 | 4/2003 |
| WO | 03/086178 A2 | 10/2003 |

(Continued)

OTHER PUBLICATIONS

Ahmed et al.,"Self-porating polymersomes of PEG-PLA and PEG-PCL: hydrolysis-triggered controlled release vesicles", Journal of Controlled Release 96(1):37-53 (2004).

(Continued)

*Primary Examiner* — Robert A Wax
*Assistant Examiner* — Randeep Singh
(74) *Attorney, Agent, or Firm* — Nixon Peabody LLP; Mark FitzGerald; Tari W. Mills

(57) ABSTRACT

The present invention provides methods to treating inflammation related disease and disorders such as an autoimmune disease and autoimmune related uveitis by administering compositions and formulations comprising MetAP-2 inhibitors as disclosed herein. The composition comprises a formulation of a fumagillol derivative that retains anti-inflammation activity and is associated with a block copolymer comprising a hydrophilic polymer moiety and a hydrophobic polymer moiety.

7 Claims, 32 Drawing Sheets

(56) References Cited

U.S. PATENT DOCUMENTS

2007/0254843 A1    11/2007    Hannig et al.

FOREIGN PATENT DOCUMENTS

| WO | 03/086382 A1 | 10/2003 |
|---|---|---|
| WO | 2005/035606 | 4/2005 |
| WO | 2005/058376 A1 | 6/2005 |
| WO | 2007/024500 A1 | 3/2007 |
| WO | 2009/036108 A1 | 3/2009 |

OTHER PUBLICATIONS

Alexis et al., "HER 2 Targeted Nanoparticle-Affibody Bioconjugates for Cancer Therapy", ChemMedChem 2 3:1839-1843 (2008).

Amadi-Obi et al.,"TH17 cells contribute to uveitis and scleritis and are expanded by IL-2 and inhibited by IL-27/STAT1", Nature Medicine 13(6):711-718 (2007).

Antoine et al., "AGM-1470, a potent angiogenesis inhibitor, prevents the entry of normal but not transformed endothelial cells into the G1 phase of the cell cycle", Cancer Research 54:2073-2076 (1994).

Benny et al., "An orally delivered small-molecule formulation with antiangiogenic and anticancer activity", Nature Biotechnology 26(7):799-807 (2008).

Benny et al., "Lodamin (PEG-PLA-TNP-470), a novel formulation for oral administration of TNP-470 as a potent antiangiogenic and anti-cancer drug," Proceedings of the American Association for Cancer Research Annual Meeting 49:264 (2008).

Bernier et al., "Fumagillin class inhibitors of methionine aminopeptidase-2", Drugs of the Future 30(5):497-508 (2005).

Bernier et al., "A methionine aminopeptidase-2 inhibitor, PPI-2458, for the treatment of rheumatoid arthritis", PNAS 101(29):10768-10773 (2004).

Betelli et al., "Induction and effector functions of Th17 cells", Nature 453:1051-1057 (2008).

Bhargava et al.,"A phase I and pharmacokinetic study of TNP-470 administered weekly to patients with advanced cancer", Clinical Cancer Research 5:1989-1995 (1999).

Blanco et al., "Multifunctional Micellar Nanomedicine for Cancer Therapy", Exp. Biol. Med. 234:123-131 (2009).

Duncan, "Polymer conjugates as anticancer nanomedicines", Nature Reviews Cancer 6:688-701 (2006).

Francis et al., "Polymeric micelles for oral drug delivery: Why and how", Pure Appl. Chem. 76(7-8):1321-1335 (2004).

Folkman, "Tumor angiogenesis", Cancer Medicine (eds. Holland, J. et al.) 132-152 (B. C. Decker Inc., Ontario, Canada, 2000).

Herbst et al., "Safety and pharmacokinetic effects of TNP-470, an angiogenesis inhibitor, combined with paclitaxel in patients with solid tumors: Evidence for activity in non-small-cell lung cancer", Journal of Clinical Oncology 20(22):4440-4447 (2002).

Ingber et al., "Synthetic analogues of fumagillin that inhibit angiogenesis and suppress tumour growth", Nature 348:555-557 (1990).

James et al., "Hitting the mother lode of tumor angiogenesis", Nature Biotechnology 26(7):769-770 (2008).

Kataoka et al., "Block copolymer micelles for drug delivery: design, characterization and biological significance", Advanced Drug Delivery Reviews 47(1):113-131 (2001).

Kawai et al., "Development of sulfonamide compounds as potent methionine aminopeptidase type II inhibitors with antiproliferative properties", Bioorganic and Medicinal Chemistry Letters 16:3574-3577 (2006).

Kim et al., "Angiogenesis inhibitors in lung cancer", Current Oncology Reports 4:325-333 (2002).

Korn et al., "IL-17 and Th17 cells", Annu. Rev. Immunol. 27:485-517 (2009).

Kudelka et al., "A phase I study of TNP-470 administered to patients with advanced squamous cell cancer of the cervix", Clinical Cancer Research 3:1501-1505 (1997).

Kudelka et al., "Complete remission of metastatic cervical cancer with the angiogenesis inhibitor TNP-470", The New England Journal of Medicine 338(14):991-992 (1998).

Lai et al., "Comparison of In vitro Nanoparticles Uptake in Various Cell Lines and In vivo Pulmonary Cellular Transport in Intratracheally Dosed Rat Model", Nanoscale Res. Lett. 3:321-329 (2008).

Liu et al., "Structure of human methionine aminopeptidase-2 complexed with fumagillin", Science 282:1324-1327 (1998).

Logothetis et al., "Phase I trial of the angiogenesis inhibitor TNP-470 for progressive androgen-independent prostate cancer", Clinical Cancer Research 7:1198-1203 (2001).

Lu et al., "Cationic albumin-conjugated pegylated nanoparticles as novel drug carrier for brain delivery", Journal of Controlled Release 107:428-448 (2005).

Nishiyama et al., "Current State, achievements, and future prospects of polymeric micelles as nanocarriers for drug and gene delivery", Pharmacology & Therapeutics 112:630-648 (2006).

Satchi-Fainaro et al., "Targeting angiogenesis with a conjugate of HPMA copolymer and TNP-470", Nature Medicine 10(3):255-261 (2004).

Satchi-Fainaro et al., "Inhibition of vessel permeability by TNP-470 and its polymer conjugate, caplostatin", Cancer Cell 7(3):251-261 (2005).

Selvakumar et al., "Methionine aminopeptidase 2 and cancer", Biochimica et Biophysica Acta 1765:148-154 (2006).

Sheppard et al., "3-Amino-2-hydroxyamides and related compounds as inhibitors of methionine aminopeptidase-2", Bioorganic and Medicinal Chemistry Letters 14:865-868 (2004).

Stadler et al., "Multi-institutional study of the angiogenesis inhibitor TNP-470 in metastatic renal carcinoma", Journal of Clinical Oncology 17(8):2541-2545 (1999).

Torchilin, "Targeted polymeric micelles for delivery of poorly soluble drugs", Cell. Mol. Life Sci. 61:2549-2559 (2004).

Wang et al., "Physiologically relevant metal cofactor for methionine aminopeptidase-2 is a manganese", Biochemistry 42:5035-5042 (2003).

Wang et al., "Correlation of tumor growth suppression and methionine aminopetidase-2 activity blockade using an orally active inhibitor", PNAS 105(6):1838-1843 (2008).

Wang et al., "Tumor Suppression by a Rationally Designed Reversible Inhibitor of Methionine Aminopeptidase 2", Cancer Research 63:7861-7869 (2003).

Xiao et al., "Recent advances in PEG-PLA block copolymer nanoparticles", International Journal of Nanomedicine 5:1057-1065 (2010).

Benny et al., "Broad Spectrum Antiangiogenic Treatment for Ocular Neovascular Diseases" PLOS ONE 5:e12515 (2010).

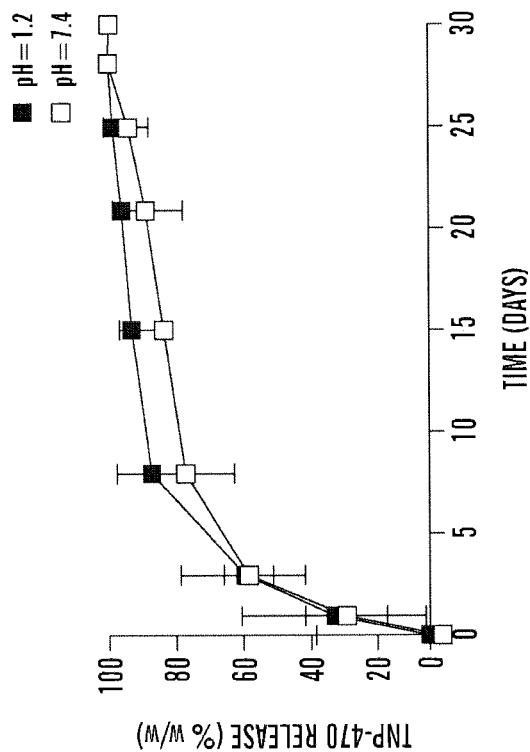
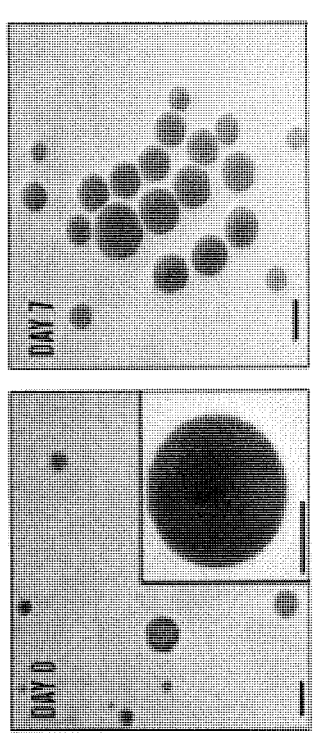
FIG. 6C
FIG. 6B

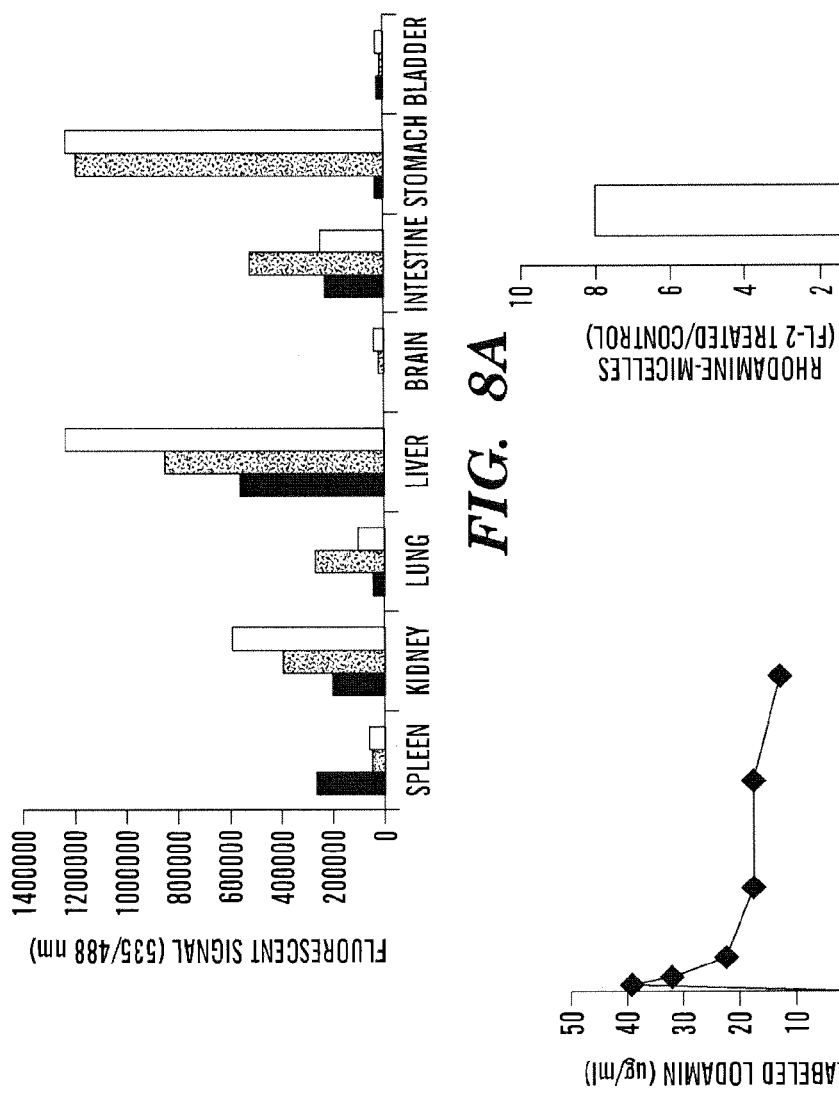

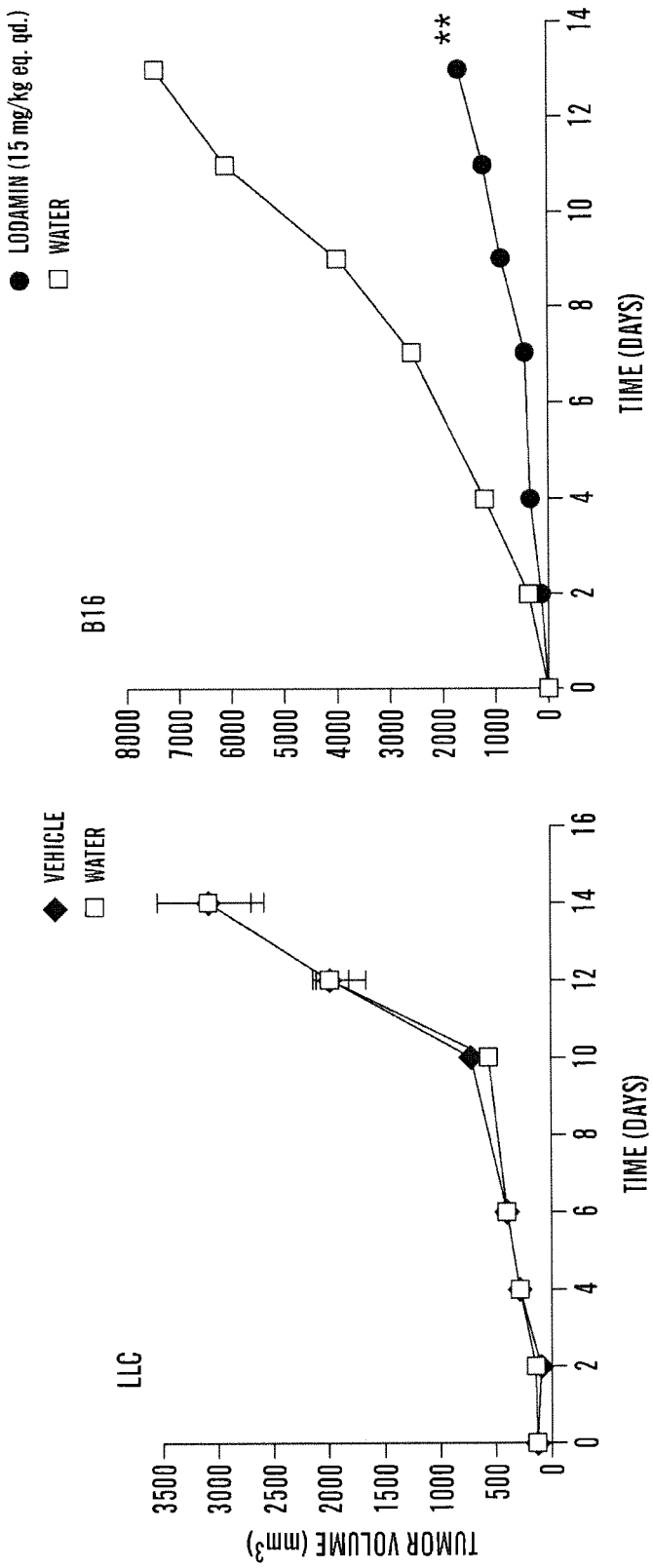

LITERATURE SYNTHESIS OF TNP-470

SYNTHETIC EXAMPLE #1

SYNTHETIC EXAMPLE #2

EXPERIMENTAL MODELS FOR AUTOIMMUNE DISEASES
EXPERIMENTAL AUTOIMMUNE UVEITIS, EAU: (MODEL OF HUMAN ENDOGENOUS UVEITIS)

EXPERIMENTAL MODELS FOR AUTOIMMUNE DISEASES
EXPERIMENTAL ALLERGIC ENCEPHALOMYELITIS, EAE: (MODEL OF HUMAN MULTIPLE SCLELOSIS)

METAP-2 INHIBITOR POLYMERSOMES FOR THERAPEUTIC ADMINISTRATION

CROSS REFERENCE TO RELATED APPLICATIONS

This application is a continuation of U.S. Non-Provisional Utility application Ser. No. 14/313,020, filed on Jun. 24, 2014, which is a is a continuation of U.S. Non-Provisional Utility application Ser. No. 12/648,155, filed on Dec. 28, 2009, which is a continuation-in-part of the International Application Serial No. PCT/US2008/068367, filed on Jun. 26, 2008, which claims benefit of priority under 35 U.S.C. §119(e) of U.S. Provisional Application No. 60/937,198 filed Jun. 26, 2007, and U.S. Provisional Application No. 61/054,595 filed May 20, 2008, the contents of each of which are incorporated herein by reference in their entireties.

GOVERNMENT SUPPORT

This invention was made with Government support under Grant No.: W81XWH-05-1-0115 awarded by the Department of Defense. The Government has certain rights in the invention.

FIELD OF THE INVENTION

The present invention relates generally to methods for the treatment of inflammation and autoimmune diseases and disorders.

BACKGROUND

Emerging data strongly implicates a ubiquitous eukaryotic enzyme "methionine aminopeptidase type 2" (MetAP-2) in many diseases (Kass 2007, Yeh 2005, Bo 2004, Bringardner 2008, Zhang 2001, Watanabe 2006). While MetAP-2's role is not yet fully understood, it is clear that expression and activity of MetAP-2, including, but not necessarily limited to over-expression or over-activity of MetAP-2, is correlated with disease progression and stage of disease (Salvukumar 2006). Compounds that inhibit MetAP-2 activity could lead to significant therapeutic benefit across a wide variety of diseases.

It is a widely accepted hypothesis that tumor growth is angiogenesis-dependent, which is supported by both biological and pharmacological evidence and confirmed by genetic evidence which provides a scientific basis for current clinical trials of angiogenesis inhibitors. Increased tumor angiogenesis and elevated levels of proangiogenic factors such as vascular endothelial growth factor (VEGF/VPF), basic fibroblast growth factor (bFGF), and interleukin-8 (IL-8) correlate with decreased survival and increased risk of relapse in studies of patients with malignant solid tumors. The importance of angiogenesis is further supported by the observation that antiangiogenic agents inhibit tumor growth in a variety of animal models.

In the U.S. there are currently more than 30 angiogenesis inhibitors in various clinical trials for late-stage cancer. One of these angiogenesis inhibitors, O-(chloracetyl-carbamoyl) fumagillol (TNP-470), is a low molecular weight synthetic compound. Fumagillol is the alcohol derived from the hydrolysis of fumagillin[3], a compound secreted by the fungus *Aspergillus fumigatus fresenius*. TNP-470 is a potent endothelial inhibitor in vitro[30]. Recently, TNP-470 has been tested as a potential new anticancer agent. TNP-470 is also referred to as AGM-1470, an analog of fumagillin, is among the most potent inhibitors of angiogenesis. The anti-angiogenic properties of the TNP-470 were tested on different tumor models in animals, and in clinical trials with a variety of malignancies such as prostate, breast, lung and cervical cancer.

In animal models, TNP-470 has the broadest anticancer spectrum of any known agent[32, 31]. TNP-470 inhibited the growth of murine tumors up to 91%, human tumors up to 100% and metastatic tumors up to 100% in mice (reviewed in ref. 31). In most studies, mice were treated at the same optimal dose of 30 mg/kg subcutaneously every other day. In clinical trials TNP-470 has shown evidence of antitumor activity when used as a single agent, with a number of objective responses reported with relapsed and refractory malignancies[17,19,23]. It has also shown promise when used in combination with conventional chemotherapy[20,34], although many patients experience neurotoxicity (malaise, rare seizures, asthenia, anxiety and dysphoria)[20,21,22, 23] at high chemotherapeutic doses where antitumor activity has been seen. In addition to its anti-angiogenic activities, TNP-470 also inhibits or prevents vascular leakage.

Methionine aminopeptidase-2 (MetAP-2) has been identified as the target of anti-angiogenic fumagillol derivatives (e.g., TNP-470).[41] The crystal structure of fumagillin complexed with MetAP-2 was reported by Liu et al.[42]

TNP-470 is generally administered via injections, for example intramuscular or intravenous delivery systems or by a continuous intravenous infusion given every few days. TNP-470 is also typically administered at high doses for a specific period of time at infrequent time intervals, for example TNP-470 is administered at high doses as a chemotherapeutic. TNP-470 is not generally administered orally.

SUMMARY

TNP-470 and other fumagillol derivative are known anti-angiogenic agents. Described herein, however, is the surprising discovery that the diblock copolymer formulationsof fumagillol derivatives are effective for the treatment or prevention of autoimmume diseases and inflammation. In particular, it is shown herein that fumagillol derivative formulations are effective for inhibiting T cell activation, proliferation and differentiation of T cells to having characteristics of or involved in autoimmune disease and/or inflammation such as inflammatory cytokine production.

Accordingly, the present invention relates to methods of inhibiting T cell activation and proliferation, treating/inhibiting inflammation, treating auto-immune related diseases and disorders, inhibiting graft-versus-host disease, and inhibiting organ transplant rejection, comprising administering a MetAP-2 inhibitor formulation comprising a MetAP-2 inhibitor having anti-proliferative activity and/or anti-inflammation activity and the MetAP-2 inhibitor associates with a block copolymer, wherein the block copolymer comprises a hydrophobic and hydrophilic moiety. In some embodiments, the MetAP-2 inhibitor is associated with a block copolymer comprising a hydrophobic moiety, wherein the hydrophobic moiety is part of a block copolymer comprising hydrophilic and hydrophobic moieties. In one embodiment, the MetAP-2 inhibitor is covalently linked to the hydrophobic moiety is part of a block copolymer. In some embodiments, the block copolymer comprising hydrophilic and hydrophobic moieties forms a micelle.

The invention thus encompasses at least the following aspects and embodiments.

In one aspect, described herein is a method of treating an autoimmune disease in a subject in need thereof, the method comprising administering a MetAP-2 inhibitor formulation comprising a MetAP-2 inhibitor having anti-inflammation activity, wherein the MetAP-2 inhibitor is associated with a block copolymer comprising a hydrophilic polymer moiety and a hydrophobic polymer moiety.

In another aspect, provided herein is a method of treating an autoimmune disease in a subject in need thereof, the method comprising administering a composition comprising a formulation of a fumagillol derivative that has anti-inflammation activity, the formulation comprising the fumagillol derivative associated with a block copolymer comprising a hydrophilic polymer moiety and a hydrophobic polymer moiety. In one embodiment, the fumagillol derivative das anti-proliferative activity.

In another aspect, provided herein is a method of treating uveitis in a subject in need thereof, the method comprising administering a MetAP-2 inhibitor formulation comprising a MetAP-2 inhibitor having anti-proliferative activity and anti-inflammation activity, wherein the MetAP-2 is associated with a block copolymer comprising a hydrophilic polymer moiety and a hydrophobic polymer moiety.

In another aspect, provided herein is a method of treating uveitis in a subject in need thereof, the method comprising administering a composition comprising a formulation of a fumagillol derivative that has anti-inflammation activity, the formulation comprising the fumagillol derivative associated with a block copolymer comprising a hydrophilic polymer moiety and a hydrophobic polymer moiety. In one embodiment, the fumagillol derivative das anti-proliferative activity.

In one embodiment of this and all other aspects described herein, the MetAP-2 inhibitor is a fumagillol derivative.

In another embodiment of this and all other aspects described herein, the MetAP-2 inhibitor is an irreversible MetAP-2 inhibitor.

In another embodiment of this and all other aspects described herein, MetAP-2 inhibitor is a reversible MetAP-2 inhibitor. Reversible inhibitors include, for example, bestatin class inhibitors or 3-amino-2-hydroxyamides and related hydroxyamides and acylhydrazines, In another embodiment of this and all other aspects described herein, block copolymer is a diblock copolymer.

In another embodiment of this and all other aspects described herein, the MetAP-2 inhibitor is covalently linked with the hydrophobic moiety of the block copolymer.

In another embodiment of this and all other aspects described herein, the fumagillol derivative is covalently linked with the hydrophobic moiety of the block copolymer.

In another embodiment of this and all other aspects described herein, the hydrophobic polymer moiety of the block copolymer is selected from the group consisting of poly(d,L-lactic acid), poly(caprolactone) (PCL), and poly(propylene oxide).

In another embodiment of this and all other aspects described herein, the hydrophobic moiety is a poly(d,L-lactic acid) (PLA) polymer.

In another embodiment of this and all other aspects described herein, the hydrophobic polymer moiety is 1-15 kDa. For example, the hydrophobic polymer moiety can be between 1-10 kDa, 1-8 kDa, 1-5 kDa, 1-3 kDa, 3-15 kDa, 5-15 kDa, 8-15 kDa, 10-15 kDa, 12-15 kDa, 2-12 kDa, 4-10 kDa, 6-8 kDa in size. In another embodiment of this and all other aspects described herein, the hydrophobic polymer is approximately 2 kDa.

In another embodiment of this and all other aspects described herein, the hydrophilic moiety is a poly(ethylene glycol) (PEG) polymer.

In one embodiment of all other aspects described herein, the PEG polymer is a capped PEG polymer.

In one embodiment, the formulation comprises a diblock copolymer micelle formed with the diblock copolymer described herein.

In another embodiment of this and all other aspects described herein, the hydrophilic polymer moiety is between 1-15 kDa. For example, a hydrophilic polymer moiety useful in the compositions as described herein can be between 1-10 kDa, 1-8 kDa, 1-5 kDa, 1-3 kDa, 3-15 kDa, 5-15 kDa, 8-15 kDa, 10-15 kDa, 12-15 kDa, 2-12 kDa, 4-10 kDa, 6-8 kDa in size. In another embodiment of this and all other aspects described herein, the hydrophilic polymer is approximately 2 kDa.

In another embodiment of this and all other aspects described herein, the polymer is a diblock copolymer comprising a PEG-PLA diblock copolymer having hydrophilic PEG and hydrophobic PLA moieties.

In another embodiment of this and all other aspects described herein, the formulation is formulated for oral administration.

In another embodiment of this and all other aspects described herein, the formulation is formulated for topical administration.

In one embodiment, the composition or formulation is administered by intravitreous injection.

In another embodiment of this and all other aspects described herein, the formulation is formulated for administration by oral, IV, peritoneal, injected (e.g., subcutaneous, intramuscular, etc.), eyedrop or ocular, suppository, topical, pulmonary, including inhaled, and nasal routes, among others, and includes a reversible or irreversible MetAP-2 inhibitor.

In another embodiment of this and all aspects described herein relating to fumagillol derivatives having anti-proliferative and/or anti-angiogenic activity, the fumagillol derivative comprises a derivative selected from the group consisting of 6-O—(N-chloroacetylcarbamoyl) fumagillol (TNP-470), 6-O-(4-methoxyaniline)acetyl fumagillol; 6-O-(3,4, 5-trimethexyaniline)acetyl fumagillol; 6-O-(4-(N,N-dimethylethoxy) aniline)acetyl fumagillol; 6-O-(cyclopropylamino) acetyl fumagillol; 6-O-(cyclobutylamino)acetyl fumagillol; 4-((cyclopropylamino)acetyl) oxy-2-(1,2-epoxy-1,5-dimethyl-4-hexenyl)-3-methoxy-1-chloromethyl-1 cyclohexanol; 4-((cyclobutylamino)acetyl) oxy-2-(1,2-epoxy-1,5 dimethyl-4-hexenyl)-3-methoxy-1-chloromethyl-1-cyclohexanol.

In another embodiment of this and all aspects described herein relating to fumagillol derivatives having anti-proliferative and/or anti-angiogenic activity, the fumagillol derivative comprises 6-O—(N-chloroacetylcarbamoyl) fumagillol (i.e., TNP-470).

In another embodiment of this and all aspects described herein, the MetAP-2 inhibitor is selected from the group consisting of a bengamide, a sulphonamide MetAP-2 inhibitor compound, a bestatin, a 3-amino-2-hydroxyamide MetAP-2 inhibitor compound, a hydroxyamide MetAP-2 inhibitor compound, an acylhydrazine MetAP-2 inhibitor compound, ovacillin, a reversible MetAP-2 inhibitor and an irreversible MetAP-2 inhibitor.

In one embodiment, the MetAP-2 inhibitor is a fumagillol derivative that has anti-proliferative, anti-inflammation and/or anti-angiogenic activity.

In some embodiments, described herein are methods of inhibiting T cell activation and proliferation, treating inflammation, auto-immune related diseases and disorders, inhibiting graft-versus-host disease, and inhibiting organ transplant rejection, the method comprising administering a micelle of conjugated MetAP-2 inhibitor, wherein MetAP-2 is conjugated to a diblock copolymer comprising a hydrophilic polymer moiety and a hydrophobic polymer moiety, wherein micelles are formed therefrom. In these embodiments, the MetAP-2 inhibitor is a fumagillol derivative that has anti-proliferative, anti-inflammation and/or anti-angiogenic activity.

Other aspects of the invention are disclosed infra.

BRIEF DESCRIPTION OF FIGURES

FIG. 6B shows TEM images of Lodamin dispersed in water, the spherical structure of the micelles are shown at different time points post incubation in water bar=10 nm.

FIG. 6C shows TNP-470 release from Lodamin during a 30 d period as determined by HPLC; Micelles were incubated in gastric fluid pH=1.2 (■) or PBS pH=7.4 (□) and analysis of the released TNP-470 was done in duplicate. The results are presented as means±SD.

FIG. 8A shows the fluorescent signal of tissue extracts and in serum of mice treated with Lodamin. Mice (n=3) were given a single dose of oral 6-coumarin labeled polymeric micelles (150 µl 30 mg/ml). Data show the values of the three different mice, autofluorescence was omitted by subtracting the fluorescent signal of tissue extracts from an untreated mouse. The percent of labeled cells was measured for each organ.

FIG. 8B shows the levels of fluorescent signals in mouse serum as measured after different time points post oral administration. The results are presented as the concentration of micelles calculated by standard calibration curve.

FIG. 8C shows the percentage of $FL2^{high}$ positive cells as isolated from the designated organs (ratio of numbers $FL2^{high}$ cells of treated tumors to those of control mouse).

FIG. 9C shows the effect of the vehicle, empty mPEG-PLA micelles, on Lewis lung carcinoma (n=5 mice per group, $*P<0.05$).

FIG. 9D shows the effect of Lodamin given at a dose of 15 mg/kg q d. (●) on B16/F10 murine melanoma tumor in C57Bl/6J; water was given as control (□) (n=5 mice per group, $*P<0.05$).

DETAILED DESCRIPTION

Figure 1:
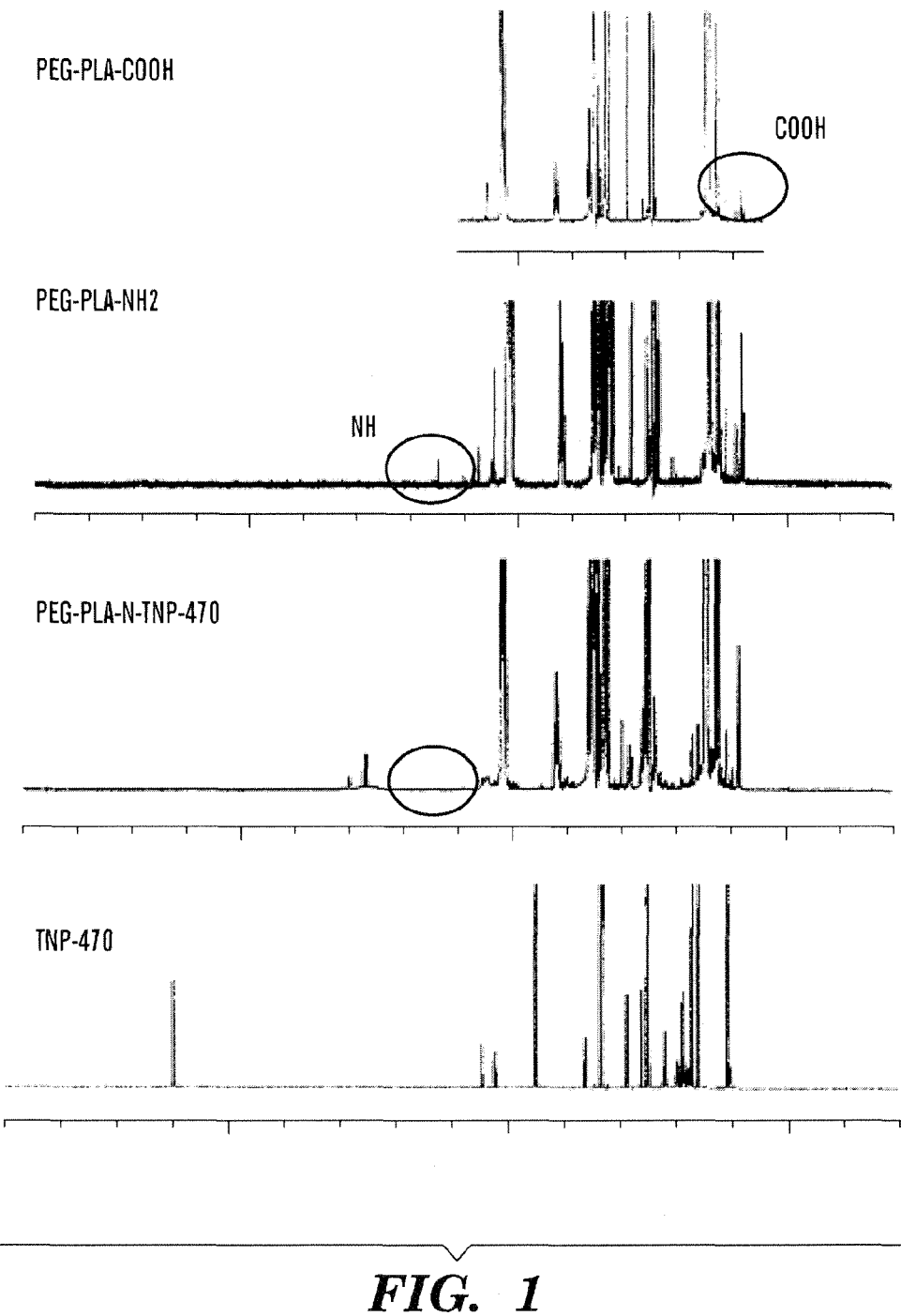
FIG. 1 shows NMR spectra for a block copolymer and a block copolymer conjugate with TNP-470. Differences in NMR pattern verify the binding of the ethylendiamine and the TNP-470 to the polymer.

The present invention relates in part to compositions and formulations comprising a MetAP-2 inhibitor associated with a block copolymer, wherein the block copolymer comprises a hydrophobic and hydrophilic moiety. The present invention relates in part to a composition comprising MetAP-2 inhibitors formulated for oral administration. In some embodiments, the composition comprises associating a MetAP-2 inhibitor with a block copolymer comprising a hydrophobic moiety, wherein the hydrophobic moiety is part of a block copolymer comprising a hydrophilic and a hydrophobic moiety. In one embodiment, the MetAP-2 inhibitor is covently linked to the hydrophobic moiety is part of a block copolymer. In some embodiments, the block copolymer comprising hydrophilic and hydrophobic moiety forms a micelle.

Accordingly, the present invention relates to a method to treat a condition in which MetAP-2 activity is involved in or required for the pathology of the condition, the method comprising administering a composition comprising a MetAP-2 inhibitor formulated as disclosed herein. In one embodiment, the composition is formulated for oral administration, although other routes including topical and by injection are specifically contemplated. In one embodiment, the condition is an autoimmune and/or inflammatory disease or disorder and the method comprises orally administering a composition comprising a MetAP-2 inhibitor formulated as disclosed herein. Other routes of administration are specifically contemplated, as discussed herein below.

Methionine aminopeptidases are essential for removal of the N-terminal methionine from nascent proteins. Following this removal, a variety of molecules are attached to the unstable, open N-terminus, including myristic acid. This acid changes the hydrophobicity of the nascent protein, and causes specific cellular localization and function. In some instances, this function may lead to pathological diseases, as with the oncogene Src.[46] Recently, MetAP-2, one of the 2 major types of aminopeptidases, has itself been identified as a possible oncogene.[47] Its importance in cell proliferation is well documented.[45]

As a result of this knowledge, numerous classes of therapeutics have been synthesized to target and inhibit MetAP-2 activity (including, but not necessarily limited to over-activity) including the fumagillin and ovacillin classes, bengamides, bestatins, pyrimidines, sulfonamides, among others (Bernier 2005). None have clinically succeeded, due partly to the non-specific nature of their bio-distribution and partly due to a poor PK (pharmacokinetic) profile, such as too rapid clearance, short half life, unacceptable levels of interaction with the nervous system, or crossing the blood-brain barrier. These issues are manifested in unwanted toxic side effects.

Many attempts have been made to overcome these issues associated with both the reversible and irreversible MetAP-2 classes of inhibitors largely through small molecule formulation, synthesis or high molecular weight (>60 kDa) polymeric conjugation. However, each formulation has shown insurmountable short-comings including too-short plasma half-life (a few minutes for the drug and less than 2 hr for the metabolites in the case of the fumagillin class compound TNP-470), weight loss with the sulfonamides and bestatins, unpredictable cardiovascular events with the bengamides, difficulty in manufacturing, questionable stability, the inability to dose patients over long periods of time, and lack of clearance or too slow clearance as with higher molecular weight polymer conjugated drugs. Again, the majority of these failures can be attributed to their non-specific biodistribution. It is therefore desirable to administer a MetAP-2 inhibitor to patients in doses and methods that are limited in overall toxicities, are stable, and can provide multiple routes of administration depending on the presentation of the disease.

Further, many MetAP-2 inhibitors, particularly those in the fumagillol class, are poorly soluble in water (1.9 mg/ml; see U.S. Pat. No. 5,536,623), and as such have low absorption and bioavailability if given orally.

In order to administer a MetAP-2 inhibitor one must overcome several issues associated with the chemical properties of the small molecule MetAP-2 inhibitors such as their poor solubility in water, low absorption, non-specific biodistribution and poor bioavailability if administered orally, topically, inhaled, or given via eyedrop. Due to these properties, the vast majority of MetAP-2 inhibitors are currently formulated for administration exclusively via injections (i.e. intramuscularly and intravenously).

As demonstrated herein, the inventors have discovered a composition that formulates MetAP-2 inhibitors such as TNP-470, among others, for alternative routes of administration other than injections, by binding the MetAP-2 inhibitor to a diblock copolymer, for example a diblock copolymer comprising PEG-PLA. The inventors have discovered that such conjugation of a MetAP-2 inhibitor with block copolymers (herein referred to as "block copolymer-MetAP-2 inhibitor conjugates") provides a highly suitable formulation for oral, topical, inhaled, intravitreal, eyedrop or intraperitoneal administration. While having advantages for oral or other non-injected routes of administration, is also contemplated herein that the block copolymer compositions described herein can also be administered by injection (e.g., intramuscular, subcutaneous, etc.).

The inventors demonstrate that a MetAP-2 inhibitor was successfully conjugated to a modified PEG-PLA polymer through its amine, and formed nano-size polymersomes. The inventors also demonstrate, using images taken by TEM, that spherical micelles were formed, and size measurement with DLS showed a low range of size distribution around 10 nanometers. By using confocal microscopy images of fluorescently-labeled polymersomes, the inventors demonstrate rapid uptake by Human Umbilical Vein Endothelial Cells (HUVECs), and when the MetAP-2 inhibitor polymersomes were added, a significant inhibition of HUVEC proliferation was shown (as compared to no effect of the carrier itself).

In-vivo studies done on mice showed a significant inhibition of subcutaneous Lewis Lung Carcinoma tumors with C57/BL mice given a daily oral administration of TNP470 micelles. A dose of 15 mg/kg TNP-470 equivalent showed 63% inhibition without any weight loss to the mice (data not shown).

Accordingly, the inventors have discovered that conjugating a MetAP-2 inhibitor such as TNP-470 to diblock copolymers is useful for formulation as an oral administration formulation and that such a MetAP-2 inhibitor-diblock copolymer conjugate is useful in a method to treat conditions that involve or require MetAP-2 activity for their pathologies, such as cancer, RA, viral infection, bacterial or fungal infection among others, and those associated with abnormal or hyperpermeable vasculature such as edema, age-related macular degeneration and diabetic retinopathy. Evidence is also provided for a surprising effect of oral or topical formulation of MetAP-2 inhibitor, particularly fumagillol derivative, for the inhibition of autoimmune disease and/or inflammation, and particularly, for example, T cell mediated inflammation.

One embodiment is an oral anti-inflammatory MetAP-2 inhibitor polymeric drug with potent efficacy in autoimmune disease modelsnamed Lodamin. The inventors characterized its physicochemical properties and show that this polymeric pro-drug derived from TNP 470 successfully overcomes the limitations of TNP-470 while retaining its anti-proliferative and antiangiogenic activities, and hemonstrate anti-inflammatory activity. Lodamin is produced by conjugation of TNP 470 to a di-block copolymer: PEG PLA. The amphiphilic nature of this polymeric drug enables self-assembly of micelles in an aqueous medium[26]. In this structure, the TNP-470 is located in the core, where it is protected from the acidic environment of the stomach, thus enabling oral availability. Furthermore, advantage is taken of using biocompatible and well characterized polymers[27,28].

Lodamin, administered orally, is effectively absorbed in the intestine and accumulates in tumor tissue. The drug significantly inhibits cell proliferation and angiogenesis, as demonstrated by inhibition of HUVEC proliferation, in the corneal micropocket assay, and in mouse tumor models. Lodamin significantly inhibited primary tumor growth as demonstrated in models of melanoma and lung cancer. Notably, oral Lodamin successfully prevented liver metastasis of smelanoma tumor cells without causing liver-toxicity or other side-effects and led to prolonged mouse survival (see PCT/US2008/68367).

Moreover, unlike the neurological impairments caused by free TNP-470, Lodamin does not penetrate the blood-brain barrier, and accordingly did not cause neurotoxicity in mice. Lodamin and similar fumagillol derivative formulations can therefore realize the benefit of fumagillol derivative with out the well known downside.

Accordingly, the inventors have discovered that conjugating MetAP-2 inhibitors to diblock copolymers is useful for formulation for an oral administration formulation.

Figure 23A:
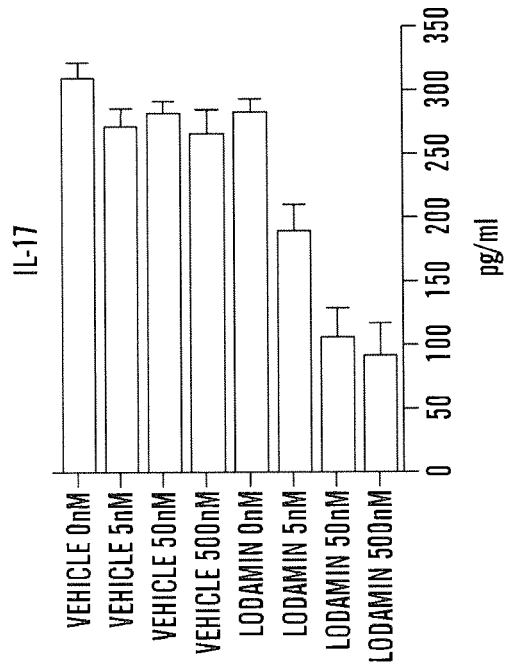
FIG. 23A shows the effects of increasing amounts of Lodamin on IFN-γ production in CD4+ T cells stimulated with plate-bound anti-CD3 (1 µg/ml) for three days as analyzed by ELISA.
Figure 23B:
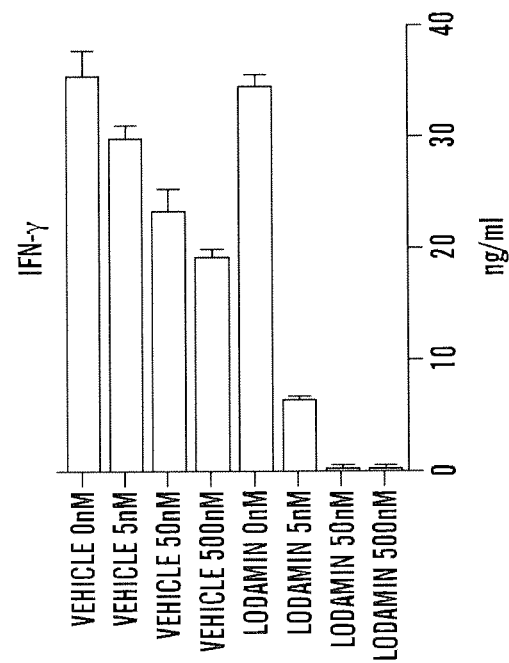
FIG. 23B shows the effects of increasing amounts of Lodamin on 11-17 production in CD4+ T cells stimulated with plate-bound anti-CD3 (1 µg/ml) for three days as analyzed by ELISA.
Figure 24:
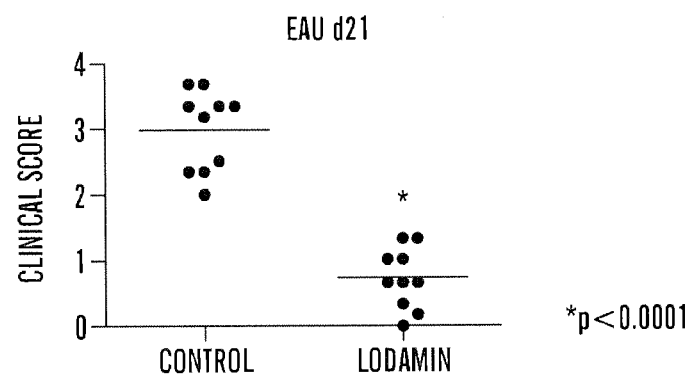
FIG. 24 shows that oral administration of Lodamin ameliorated experimental autoimmune uveoretinitis (EAU). EAU was induced by immunizing C57BL/6 mice with human interphotoreceptor retinoid-binding protein (IRBP) 1-20. Lodamin at a dose of 30 mg/kg, or vehicle was orally administrated every other day after immunization. EAU severity was evaluated clinically and histopathologically on day 21.
Figure 24:
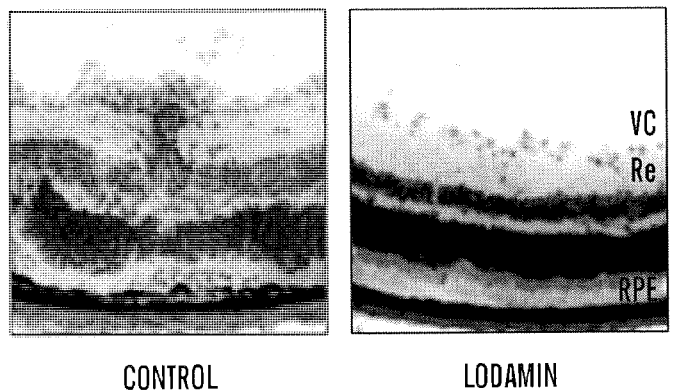
Figures 25A, 25B:
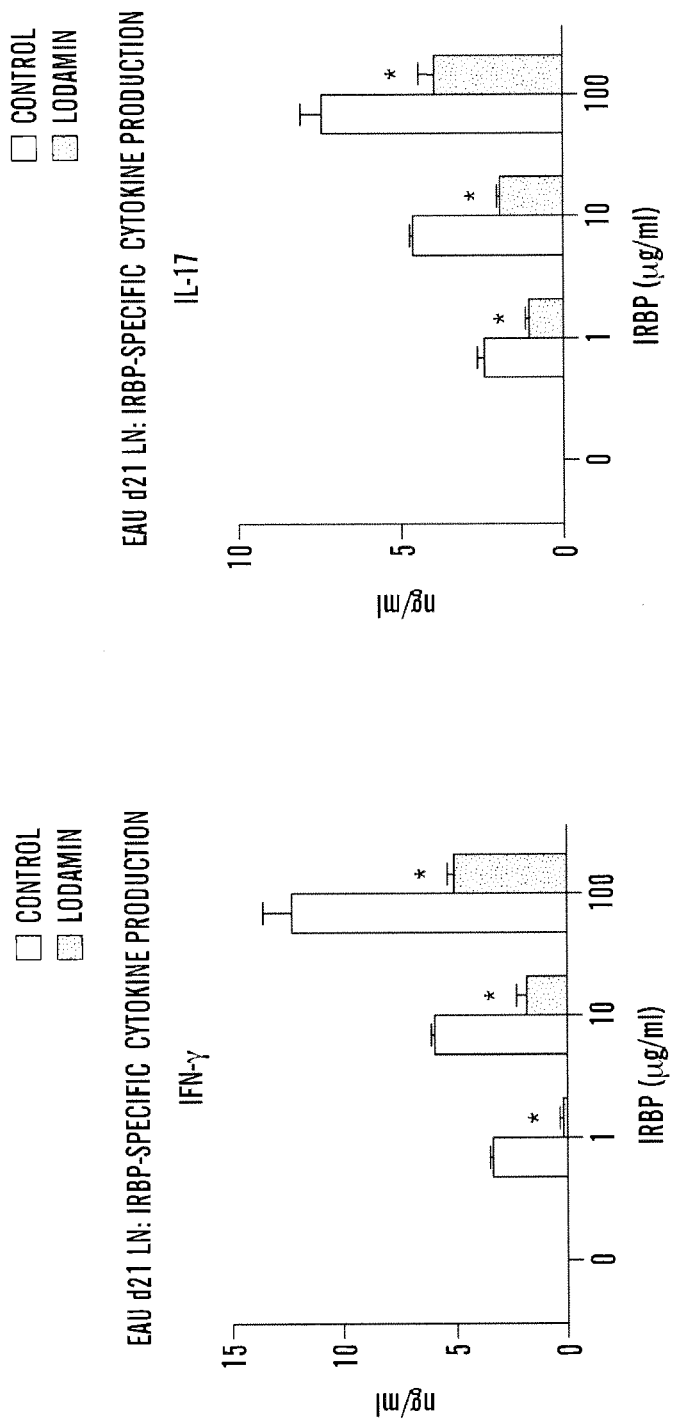
FIG. 25A and FIG. 25B show the suppression of antigen-specific cytokine production by lymph nodes from Lodamin administered EAU mice. On day 21 after immunization, draining lymph node cells were harvested and IRBP-specific IFN-γ (FIG. 25A) and IL-17 (FIG. 25B) production was analyzed by ELISA.
Figure 26:
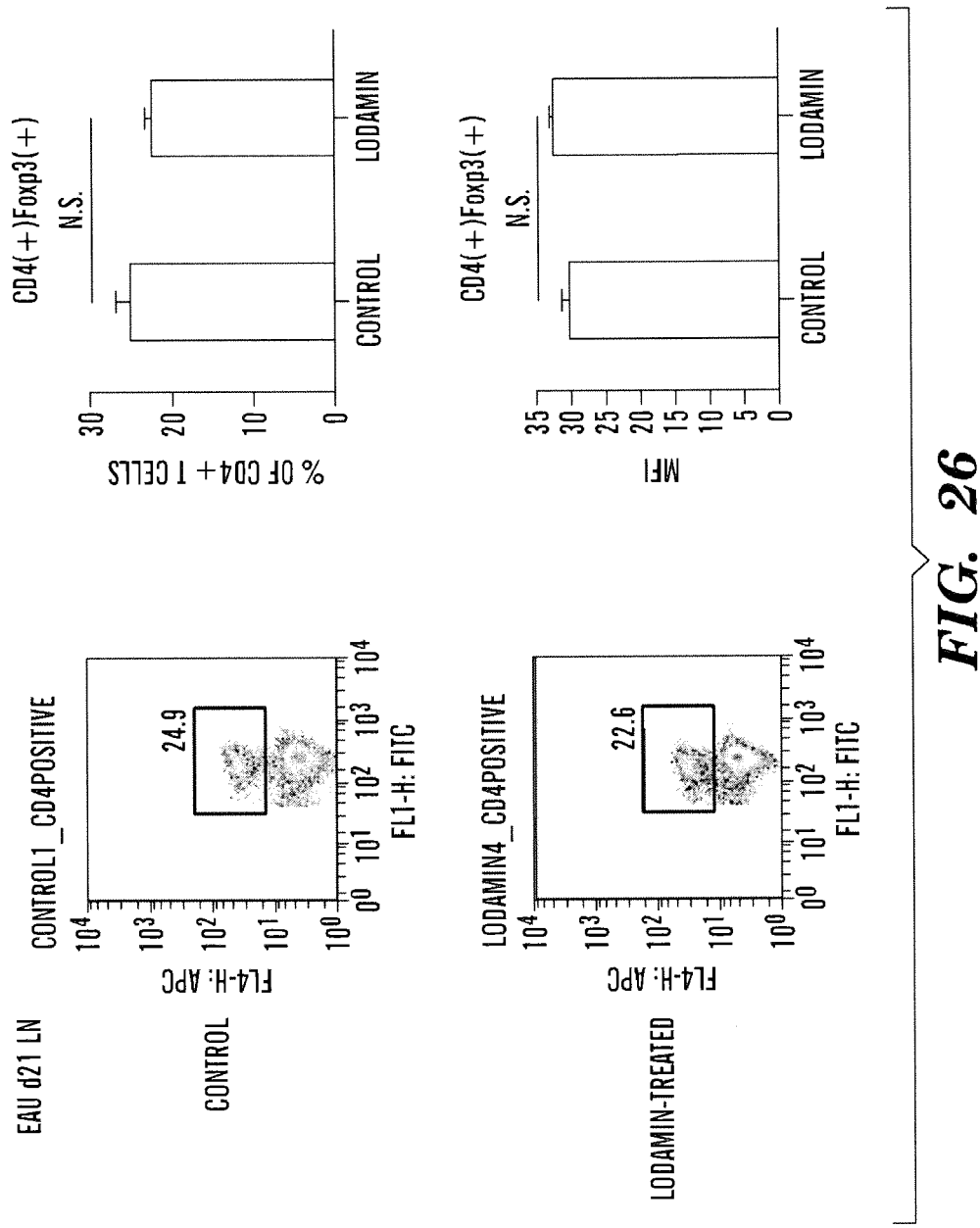
FIG. 26 shows Foxp3 expression, as a representative marker for regulatory T cells, by draining lymph node cells from Lodamin administered EAU mice (n=5). On day 21 after immunization, draining lymph node cells were harvested and cell surface was stained with APC-labeled anti-CD4 antibody, followed by intracellular Foxp3 staining.

Subsequent to the development of Lodamin for the treatment of proliferative and angiogenic disorders, the inventors have found that Lodamin, a polymeric conjugate of TNP-470, has anti-inflammatory properties. Lodamin suppressed the pro-inflammation cytokines INF-γ, and IL-17 production in T cells, suppressed T cell proliferation, suppressed T cell activation and suppressed T cell differentiation, and suppress inflammatory cytokine production (see Example 7, FIGS. 19-27). In addition, in the experimental autoimmune uveoretinitis model (EAU), oral administration of Lodamin to the mice for 21 days resulted in significantly reduced clinical score for the disease condition (FIG. 24). Orally administered Lodamin also suppressed the production of pro-inflammation cytokines INF-γ, IL-17A, and IL-6 in T cells from EAU mice retina (FIGS. 25 and 27), and suppressed CD4+ T cell proliferation (FIG. 26).

Accordingly, the invention herein provides a method of inhibiting the activation and/or proliferation of a CD4+ T cell in a subject in need thereof, the method comprising administering a MetAP-2 inhibitor formulation comprising a MetAP-2 inhibitor having anti-inflammation activity, associated with a block copolymer comprising a hydrophilic polymer moiety and a hydrophobic polymer moiety. In one embodiment, the MetAP-2 inhibitor is a fumagillol derivative. In one embodiment, the MetAP-2 inhibitor is covalently linked to the hydrophobic polymer moiety of the block copolymer.

In another embodiment, provided herein is a method of inhibiting of the activation and/or proliferation of a CD4+ T cell in a subject in need thereof, the method comprising administering a composition comprising a formulation of a fumagillol derivative that has anti-inflammation activity, the formulation comprising the fumagillol derivative associated with a block copolymer comprising a hydrophilic polymer moiety and a hydrophobic polymer moiety.

This ability of inhibiting T cells activation and/or proliferation represents a significant and clinically relevant avenue for the treatment and intervention of T cell-mediated diseases and disorders. T cell-mediated diseases and disorders include, but are not limited to, general inflammation, organ-specific auto-immune diseases such as inflammatory arthritis, type I diabetes mellitus, multiple sclerosis, psoriasis, inflammatory bowel diseases, vasculitis; allergic inflammation such as allergic asthma, atopic dermatitis, and contact hypersensitivity, organ transplant rejection; graft-versus-host disease; and T cell lymphomas and leukemia.

Inflammatory conditions, afflictions, illnesses, and diseases contemplated for treatment with the formulation described herein include but are not limited to: (1) all varieties of dermatitis, seborrhea, psoriasis, eczema, and allergic; (2) subcutaneous inflammatory conditions including tendonitis, myositis, fasciitis, neuritis, arthritis, arteritis, phlebitis, and back pain—especially back pain associated with inflammatory nodules; (3) repetitive strain injuries (RSIs) including cumulative trauma disorders, tendonitis, Raynaud's syndrome and phenomena, the tunnel syndromes, and reflex sympathetic dystrophy; (4) collagen vascular diseases including Systemic lupus erythematosis, rheumatoid arthritis, dermatomyositis, scleroderma, and polyarteritis nodosa; (5) pulmonitis, myocarditis, pericarditis, mediastinitis, peritonitis, pancreatitis, gastritis, hepatitis, cholecystitis, nephritis, cystitis, urethritis, temporal-mandibular joint (TMJ) problems or disease; (6) multiple sclerosis, amyotrophic lateral sclerosis, and inflammation due to trauma, e. g. burns or other injuries.

In one embodiment, the invention described herein is a method of treating inflammation in a subject in need thereof, the method comprising administering a MetAP-2 inhibitor formulation comprising a MetAP-2 inhibitor having anti-proliferative activity and/or anti-inflammation activity, aassociated with a block copolymer comprising a hydrophilic polymer moiety and a hydrophobic polymer moiety. In one embodiment, the MetAP-2 inhibitor is covalently linked to the hydrophobic polymer moiety of the block copolymer. In one embodiment, the MetAP-2 inhibitor is a fumagillol derivative. The formulation should at the minimum have anti-inflammatory activity or anti-autoimmune activity in the assays or model systems described herein.

In another embodiment, provided herein is a method of treating inflammation in a subject in need thereof, the method comprising administering a composition comprising a formulation of a fumagillol derivative that has anti-inflammation activity and/or anti-angiogenic activity, wherein the formulation comprises the fumagillol derivative associated with a block copolymer comprising a hydrophilic polymer moiety and a hydrophobic polymer moiety. In one embodiment, the fumagillol derivative is covalently linked to the hydrophobic polymer moiety of the block copolymer.

In one embodiment, the inflammation is T cell-mediated.

As used herein, treatment of "inflammation" refers to treatment of inflammation resulting from various causes, including the inflammation associated with diseases or conditions of the vascular system (inclusive of the heart, the brain and the renal system), for example inflammation from pathogen infection, sunburns, physical injury etc. Non limiting examples of inflammation associated diseases or conditions are: a gastrointestinal disease or condition other than GI complications of NSAIDs (e.g. inflammatory bowel diseases, Crohn's disease, regional enteritis, ulcerative colitis, diverticulitis, pancreatitis); a respiratory/pulmonary disease or condition (e.g. emphysema, acute respiratory distress syndrome, asthma, bronchitis, chronic obstructive pulmonary disease); a musculoskeletal disease or condition (e.g. arthritis including rheumatoid arthritis, osteoarthritis, gouty arthritis, juvenile arthritis, degenerative joint diseases, and spondyloarthropathies, muscle or joint strains or sprains, osteoporosis, loosening of artificial joint implants, myositis, polymyositis, bursitis, synovitis, ankylosing spondylitis, tendonitis); a dermal disease or condition (e.g. psoriasis, eczema, scleroderma, dermatitis, epidermolysis bullosa); an allergic disease or condition (e.g. allergic reactions, allergic contact hypersensitivity); ocular inflammatory diseases or conditions (e.g. uveitis, conjunctivitis, scleritis, episcleritis, optic uveitis, keratitis, retinal vasculitis, ocular cicatricial pemphigoid, Mooren's corneal ulcer, Birdshot retinochoroidopathy, Vogt-Koyanagi Harada syndrome and sympathetic opthalmia); a diabetes-associated condition (e.g. diabetic retinopathy, diabetic neuropathy, diabetic nephropathy, inflammatory conditions associated with type I and type II diabetes); and systemic lupus erythematosis; inflammation-associated with burns; an inflammatory disease or condition affecting multiple organs (e.g. Sarcoidosis, Behcet's syndrome).

In one embodiment, the inflammation is acute. In another embodiment, the inflammation is chronic. Inflammation is a basic way in which the body reacts to infection, irritation, foreign substances such as bacteria and viruses or other injury via the body's white blood cells and chemicals. It is the complex biological response of vascular tissues to harmful stimuli, such as pathogens, damaged cells, or irritants. Inflammation occurs as the body's protective attempt to remove the injurious stimuli as well as initiate the healing process for the tissue. Key inflammation feature being redness, warmth, swelling and pain.

Inflammation can be classified as either acute or chronic. Acute inflammation is the initial response of the body to harmful stimuli and is achieved by the increased movement of plasma and leukocytes (T-cells and B-cells) from the blood into the injured tissues. A cascade of biochemical events propagates and matures the inflammatory response, involving the local vascular system, the immune system, and various cells within the injured tissue.

The process of acute inflammation is initiated by cells already present in all tissues, mainly resident macrophages, dendritic cells, histiocytes, Kuppfer cells and mastocytes. At the onset of an infection, burn, or other injuries, these cells undergo activation and release inflammatory mediators (e. g. TNF-α, chemokines, IL-1, histamine, and reactive oxygen species, ROS) responsible for the clinical signs of inflammation. Vasodilation and its resulting increased blood flow cause the redness (rubor) and increased heat (calor). Increased permeability of the blood vessels results in an exudation (leakage) of plasma proteins and fluid into the tissue (edema), which manifests itself as swelling. Some of the released mediators such as bradykinin increase the sensitivity to pain (hyperalgesia, dolor). The mediator molecules also alter the blood vessels to permit the migration of leukocytes, mainly neutrophils, outside of the blood vessels (extravasation) into the tissue. The neutrophils migrate along a chemotactic gradient created by the local cells to reach the site of injury. The loss of function is probably the result of a neurological reflex in response to pain. Release of inflammatory mediators recruits all the types of white blood cell to the site, including T cells and B cells. In addition, the mediators also activate many of these recruited cells to produce their own mediators of inflammation, e. g. IFN-γ, LTB4, C5a, IL-8, IL17, IL-1, TNF-α and IL-6.

In addition to cell-derived mediators, several acellular biochemical cascade systems consisting of preformed plasma proteins act in parallel to initiate and propagate the inflammatory response. These include the complement system activated by bacteria, and the coagulation and fibrinolysis systems activated by necrosis, e.g. a burn or a trauma.

The acute inflammatory response requires constant stimulation to be sustained. Inflammatory mediators have short half lives and are quickly degraded in the tissue. Hence, inflammation ceases once the stimulus has been removed.

Prolonged inflammation, known as chronic inflammation, leads to a progressive shift in the type of cells which are present at the site of inflammation and is characterized by simultaneous destruction and healing of the tissue from the inflammatory process.

In acute inflammation, if the injurious agent persists, chronic inflammation can ensue. This process, marked by inflammation lasting many days, months or even years, may lead to the formation of a chronic wound. Chronic inflammation is characterised by the dominating presence of macrophages in the injured tissue. Macrophage release toxins (including reactive oxygen species) that are injurious to the organism's own tissues as well as invading agents. Consequently, chronic inflammation is almost always accompanied by tissue destruction.

In some diseases, however, the immune system inappropriately triggers an inflammatory response when there are no foreign substances to neutralize. In these diseases autoimmune diseases, the body's normally protective immune system causes damage to its own tissues.

In one embodiment, the invention herein provides a method of treating an auto-immune-related disease or disorder in a subject in need thereof, the method comprising administering a MetAP-2 inhibitor formulation comprising a MetAP-2 inhibitor having anti-proliferative activity and/or anti-inflammation activity, associated with a block copolymer comprising a hydrophilic polymer moiety and a hydrophobic polymer moiety. In one embodiment, the MetAP-2 inhibitor is a fumagillol derivative. In one embodiment, the MetAP-2 is covalently linked to the hydrophobic polymer moiety.

In another embodiment, provided herein is a method of treating an auto-immune-related disease or disorder in a subject in need thereof, the method comprising administering a composition comprising a formulation of a fumagillol derivative that has anti-inflammation activity, the formulation comprising the fumagillol derivative is associated with a block copolymer comprising a hydrophilic polymer moiety and a hydrophobic polymer moiety. In one embodiment, the fumagillol derivative is covalently linked to the hydrophobic polymer moiety.

In one embodiment, the auto-immune-related disease or disorder is T cell-mediated. T cell involvement may be evidenced by the presence of elevated numbers of T cells at the site of disease, the presence of T cells specific for autoantigens, the release of performs and granzymes at the site of disease, response to immunosuppressive therapy, etc. One skilled in the art can determine the level of involvement of T cells, e. g. based on the number of reactive T cells found in a sample, as compared to a negative control from a naive host, or standardized to a data curve obtained from one or more patients. In addition to detecting the qualitative and quantitative presence of auto-antigen reactive T cells, the T cells may be typed as to the expression of cytokines known to increase or suppress inflammatory responses. It may also be desirable to type the epitopic specificity of the reactive T cells.

T cells may be isolated from patient peripheral blood, lymph nodes, or preferably from the site inflammation. Reactivity assays may be performed on primary T cells, or the cells may be fused to generate hybridomas. Such reactive T cells may also be used for further analysis of disease progression, by monitoring their in situ location, T cell receptor utilization, etc. Assays for monitoring T cell responsiveness are known in the art, and include proliferation assays and cytokine release assays.

Proliferation assays measure the level of T cell proliferation in response to a specific antigen, and are widely used in the art. In an exemplary assay, patient lymph node, blood or spleen cells are obtained. A suspension of from about $10^4$ to $10^7$ cells, usually from about $10^5$ to $10^6$ cells is prepared and washed, then cultured in the presence of a control antigen, and test antigens. The test antigens may be peptides of any autologous antigens suspected of inducing an inflammatory T cell response. The cells are usually cultured for several days. Antigen-induced proliferation is assessed by the monitoring the synthesis of DNA by the cultures, e.g. incorporation of 3 H-thymidine during the last 18 H of culture.

Enzyme linked immunosorbent assay (ELISA) assays are used to determine the cytokine profile of reactive T cells, and may be used to monitor for the expression of such cytokines as IL-2, IL-4, IL-5, IFNγ, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

Auto-immune related diseases and disorders arise from an overactive and/or abnormal immune response of the body against substances (autoantigens) and tissues normally present in the body, otherwise known as self or autologous substance. This dysregulated inflammatory reaction causes an exaggerated response by macrophages, granulocytes, and/or T-lymphocytes leading to abnormal tissue damage and cell death. Subsequent loss of function is associated with inflammatory tissue damage.

An "autoimmune disease" or "auto-immune related disease" herein is a disease or disorder arising from and directed against an individual's own tissues or a co-segregate or manifestation thereof or resulting condition therefrom.

Autoantigens, as used herein, are endogenous proteins or fragments thereof that elicit this pathogenic immune response. Autoantigen can be any substance or a portion thereof normally found within a mammal that, in an autoimmune disease, becomes the primary (or a primary) target of attack by the immune system. The term also includes antigenic substances that induce conditions having the characteristics of an autoimmune disease when administered to mammals. Additionally, the term includes peptic subclasses consisting essentially of immunodominant epitopes or immunodominant epitope regions of autoantigens. Immunodominant epitopes or regions in induced autoimmune conditions are fragments of an autoantigen that can be used instead of the entire autoantigen to induce the disease. In humans afflicted with an autoimmune disease, immunodominant epitopes or regions are fragments of antigens specific to the tissue or organ under autoimmune attack and recognized by a substantial percentage (e.g. a majority though not necessarily an absolute majority) of autoimmune attack T-cells.

Autoantigens that are known to be associated with autoimmune disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA12) with insulin dependent diabetes.

Auto-immune-related diseases or disorders may be restricted to certain organs such as thyroiditis, type 1 diabetes mellitus, Hashimoto's thyroidits, Graves' disease, celiac disease, multiple scleroIsis, Guillain-Barre syndrome, Addison's disease, and Raynaud's phenomenon, or involve a particular tissue in different places, e.g. Goodpasture's disease which may affect the basement membrane in both the lung and the kidney.

Other examples of auto-immune-related diseases or disorders include, but should not be construed to be limited to, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimrnune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, an immune complex disorder such as immune complex nephritis, antibody-mediated nephritis, polyneuropathies, chronic neuropathy such as IgM polyneuropathies or IgM-mediated neuropathy, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, lupoid hepatitis, giant-cell hepatitis, autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies including channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, Sampter's syndrome, Caplan's syndrome, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, cyclitis such as chronic cyclitis, heterochronic cyclitis, iridocyclitis (acute or chronic), or Fuch's cyclitis, Henoch-Schonlein purpura, SCID, sepsis, endotoxemia, post-vaccination syndromes, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, idiopathic nephritic syndrome, minimal change nephropathy, benign familial and ischemia-reperfusion injury, transplant organ reperfusion, retinal autoimmunity, aphthae, aphthous stomatitis, arteriosclerotic disorders, aspermiogenesis, autoimmune hemolysis, Boeck's disease, enteritis allergica, erythema nodosum leprosum, idiopathic facial paralysis, chronic fatigue syndrome, febris rheumatica, Hamman-Rich's disease, sensoneural hearing loss, ileitis regionalis, leucopenia, transverse myelitis, primary idiopathic myxedema, ophthalmia symphatica, polyradiculitis acuta, pyoderma gangrenosum, acquired spenic atrophy, vitiligo, toxic-shock syndrome, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndrome type I, adult-onset idiopathic hypoparathyroidism (AOIH), myocarditis, nephrotic syndrome, primary sclerosing cholangitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, granulomas containing eosinophils, seronegative spondyloarthritides, polyendocrine autoimmune disease, sclerosing cholangitis, sclera, episclera, Bruton's syndrome, transient hypogammaglobulinemia of infancy, Wiskott-Aldrich syndrome, ataxia telangiectasia syndrome, angiectasis, autoimmune disorders associated with collagen disease, rheumatism, allergic hypersensitivity disorders, glomerulonephritides, reperfusion injury, ischemic re-perfusion disorder, lymphomatous tracheobronchitis, inflammatory dermatoses, dermatoses with acute inflammatory components, and autoimmune uveoretinitis (AUR).

A common feature in a number of autoimmune related diseases and inflammatory conditions is the involvement of pro-inflammatory $CD4^+$ T cells. These T cells are responsible for the release of inflammatory, Th1 type cytokines. Cytokines characterized as Th1 type include interleukin 2 (IL-2), γ-interferon, TNFα and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-β. It has been found that Th1 and Th2 type T cells may use the identical antigen receptor in response to an immunogen; in the former producing a stimulatory response and in the latter a suppressive response.

Cytokines play a critical role in the development and recovery from autoimmune diseases. For example, Th1 cytokines such as interleukin 12 (IL-12) and interferon gamma (IFNγ) have been found in the central nervous system (CNS) of multiple sclerosis (MS) patients as well as in animals with EAE (Issazadeh et al. (1995). J Neuroimmunol 61:205-12). Th2 cytokines such as IL-4, IL-5 and IL-10 have been found to be elevated either during remission of MS or EAE (Waisman et al. (1997) Immunointervention in autoimmunity by Th1/Th2 regulation, L. Adorini, ed. (Austin, Tex.: R.G. Landes Co.), pp. 129-50). Previous studies have shown that systemic administration of IL4 as well as local CNS administration of IFNγ can reduce the severity of EAE (Racke et al. (1994) J Exp Med 180:1961-6; Voorthuis et al. (1990) Clin Exp Immunol 81:183-8). Furthermore, the addition of IL-4 to naive T cells can result in the development of Th2 type cells, whereas the addition of IL-12 can result in the development of Th1 type cells (Macatonia et al. (1993) Int Immunol 5:1119-28).

Reagents targeting T cells have been developed and used to treat several autoimmune diseases (see review in Nature Immunology 2007, 8:25-30) For example, CTLA-4 Ig (Abatacept) inhibits the activation of T cells and has been approved for treating rheumatoid arthritis. Natalizumab interferes with the migration of T cells and is used for treating multiple sclerosis.

In one embodiment, the formulation comprising a MetAP-2 inhibitor and/or a fumagillol derivative having anti-inflammation activity, anti-proliferative activity and/or anti-angiogenic activity, covalently linked to a block copolymer comprising a hydrophilic polymer moiety and a hydrophobic polymer moiety can be administered in conjunction with the common drugs used for for the specific auto-immune disease and disorders such as azathioprine, infliximab, omalizumab, daclizumab, adalimumab, eculizumab, efalizumab, natalizumab, omalizumab and/or methotrexate among others.

In one embodiment, described herein is a method of inhibiting organ transplant rejection in a subject in need thereof, the method comprising administering a MetAP-2 inhibitor formulation comprising a MetAP-2 inhibitor having anti-proliferative activity and/or anti-inflammation activity, covalently linked to a block copolymer comprising a hydrophilic polymer moiety and a hydrophobic polymer moiety. In one embodiment, the MetAP-2 inhibitor is a fumagillol derivative.

In another embodiment, provided herein is a method of inhibiting organ transplant rejection in a subject in need thereof, the method comprising administering a composition comprising a formulation of a fumagillol derivative that has anti-inflammation activity and/or anti-proliferative activity, in which the formulation comprising the fumagillol derivative is associated with a block copolymer comprising a hydrophilic polymer moiety and a hydrophobic polymer moiety.

In one embodiment, organ transplant rejection is T cell-mediated.

Transplant rejection occurs when the immune system of the recipient of a transplant attacks the transplanted donor organ or tissue such as the heart, lungs, pancreas, liver, and kidneys.

Acute organ rejection is generally mediated by T cell responses to proteins from the donor organ which differ from those found in the recipient. The development of T cell responses first occurs several days after a transplant if the patient is not taking immunosuppressant drugs. Acute organ rejection is caused by mismatched human leukocyte antigens (HLA) antigens that are present on all cells. HLA antigens are polymorphic therefore the chance of a perfect match is extremely rare.

Physicians skilled in the art can recognize and diagnose transplant rejection. A biopsy of the transplanted organ can confirm that it is being rejected. Some of the signs and symptoms of rejection for specific organs include:

Kidney Rejection-Fever over 38° C. or 100.4° F., decreased urine output, weight gain over 2 pounds per day, increased blood pressure, and pain over kidney.

Liver Rejection-Fever over 38° C. or 100.4° F., fatigue, jaundice (yellowing of skin or eyes), darkening of urine, clay-colored stools, and pain over liver.

Pancreas Rejection-Fever over 38° C. or 100.4° F., increased blood sugars and pain over pancreas.

The risk of acute rejection is highest in the first 3 months after transplant. With the development of powerful immunosuppressive drugs such as cyclosporin, tacrolimus and rapamycin, the incidence of acute rejection has been greatly decreased, however, organ transplant recipients can develop acute rejection episodes months to years after transplant. Acute rejection episodes can destroy the transplant if it is not recognized and treated appropriately. Episodes occur in around 60-75% of first kidney transplants, and 50 to 60% of liver transplants. Untreated acute rejection leads to scarring and damage of the donor organ, which then require the recipient to undergo a second or third organ transplant, and often set the stage for chronic rejections of grafts.

Accordingly, administration of a therapeutically-effective amount of a formulation comprising a MetAP-2 inhibitor and/or a fumagillol derivative having anti-inflammation activity, anti-proliferative activity and/or anti-angiogenic activity, covalently linked to a block copolymer comprising a hydrophilic polymer moiety and a hydrophobic polymer moiety, shortly before organ or tissue transplant, or immediately after transplant can prevent organ/tissue transplant rejection from developing. The formulation described herein can also be administered at the initial diagnosis of such transplant rejection to stop and/or prevent the rejection from progressing further, or to slow the rejection progression to buy time while searching/waiting for another suitable organ to become available for transplant. It is also envisioned that the therapeutically-effective amount of a MetAP-2 inhibitor and/or a fumagillol derivative covalently linked to a block copolymer comprising a hydrophilic polymer moiety and a hydrophobic polymer moiety can be administered in conjunction with powerful immunosuppressive drugs such as cyclosporin, tacrolimus, daclizumab, anti-IL-2 antibody, azathioprine, mycophenolate and rapamycin to suppress organ or tissue transplant rejection.

In one embodiment, described herein is a method of inhibiting graft-versus-host disease in a subject in need thereof, the method comprising administering a MetAP-2 inhibitor formulation comprising a MetAP-2 inhibitor having anti-proliferative activity and/or anti-inflammation activity, associated with a block copolymer comprising a hydrophilic polymer moiety and a hydrophobic polymer moiety. In one embodiment, the MetAP-2 inhibitor is a fumagillol derivative. In one embodiment, the MetAP-2 inhibitor is covalently linked to the block copolymer. In one embodiment, the MetAP-2 inhibitor is covalently linked to the hydrophobic polymer moiety of the block copolymer.

In another embodiment, provided herein is a method of inhibiting graft-versus-host disease in a subject in need thereof, the method comprising administering a composition comprising a formulation of a fumagillol derivative that has anti-inflammation activity and/or anti-proliferative activity, in which the formulation comprising the fumagillol derivative is associated with a block copolymer comprising a hydrophilic polymer moiety and a hydrophobic polymer moiety. In one embodiment, the fumagillol derivative is covalently linked to the block copolymer. In one embodiment, the fumagillol derivative is covalently linked to the hydrophobic polymer moiety of the block copolymer.

In one embodiment, the graft-versus-host disease is T cell-mediated.

GVHD is a common complication of allogeneic bone marrow transplant in which functional immune cells in the transplanted marrow recognize the recipient as "foreign" and mount an immunologic attack. After bone marrow transplant, T cells present in the graft, neither as contaminants or intentionally introduced into the host, attack the tissues of the transplant recipient after perceiving host tissues as antigenically foreign. The T cells produce an excess of cytokines, including tumor necrosis factor (TNF) alpha and interleukin-1 (IL-1). A wide range of host antigens can initiate graft-versus-host-disease, among them the human leukocyte antigens (HLAs). However, graft-versus-host disease can occur even when HLA-identical siblings are the donors. HLA-identical siblings or HLA-identical unrelated donors often have genetically different proteins (called minor histocompatibility antigens) that can be presented by MHC molecules to the recipient's T-cells, which see these antigens as foreign and so mount an immune response.

While donor T-cells are undesirable as effector cells of graft-versus-host-disease, they are valuable for engraftment by preventing the recipient's residual immune system from rejecting the bone marrow graft (host-versus-graft). Additionally, as bone marrow transplant is frequently used to cure cancer, mainly leukemias, donor T-cells have proven to have a valuable graft-versus-tumor effect.

Classically, acute graft-versus-host-disease is characterized by selective damage to the liver, skin and mucosa, and the gastrointestinal tract. Newer research indicates that other graft-versus-host-disease target organs include the immune system (the hematopoietic system—e.g. the bone marrow and the thymus) itself, and the lungs in the form of idiopathic pneumonitis. Chronic graft-versus-host-disease damages the above organs, but also causes changes to the connective tissue (e.g. of the skin and exocrine glands).

Transfusion-associated graft versus host disease (TA-GvHD) is a rare complication of blood transfusion, in which the donor T lymphocytes mount an immune response against the recipient's lymphoid tissue. Donor lymphocytes are usually identified as foreign and destroyed by the recipient's immune system. However, in situations where the recipient is immunocompromised (inborn immunodeficiency, acquired immunodeficiency, malignancy), or when the donor is homozygous and the recipient is heterozygous for an HLA haplotype (as can occur in directed donations from first-degree relatives), the recipient's immune system is not able to destroy the donor lymphocytes. This can result in graft versus host disease.

Graft-versus-host-disease can largely be avoided by performing a T-cell depleted bone marrow transplant. These types of transplants result in reduced target organ damage and generally less graft-versus-host-disease, but at a cost of diminished graft-versus-tumor effect, a greater risk of engraftment failure, and general immunodeficiency, resulting in a patient more susceptible to viral, bacterial, and fungal infection. Methotrexate and cyclosporin are common drugs used for GVHD prophylaxis.

In some embodiments, the formulation comprising a MetAP-2 inhibitor and/or a fumagillol derivative having anti-inflammation activity, anti-proliferative activity and/or anti-angiogenic activity, which is covalently linked to a block copolymer comprising a hydrophilic polymer moiety and a hydrophobic polymer moiety of the present invention can be administered simultaneously during the bone marrow transplant or blood transfusion, or administered shortly thereafter as a prophylaxis in preventing GVHD and TA- GvHD respectively. In one embodiment, the formulation comprising a MetAP-2 inhibitor and/or a fumagillol derivative having anti-inflammation activity, anti-proliferative activity and/or anti-angiogenic activity which is covalently linked to a block copolymer comprising a hydrophilic polymer moiety and a hydrophobic polymer moiety can be administered in conjunction with the common drugs used for GVHD prophylaxis, such as methotrexate and cyclosporin.

In one embodiment, described herein is a method of treating uveitis in a subject in need thereof, the method comprising administering a MetAP-2 inhibitor formulation comprising a MetAP-2 inhibitor having anti-proliferation activity and/or anti-inflammation activity, associated with a block copolymer comprising a hydrophilic polymer moiety and a hydrophobic polymer moiety. In one embodiment, the MetAP-2 inhibitor is a fumagillol derivative. In one embodiment, the MetAP-2 inhibitor has anti-inflammation activity or anti-proliferative activity.

In another embodiment, described herein is a method of treating uveitis in a subject in need thereof, the method comprising administering a composition comprising a formulation of a fumagillol derivative that retains anti-inflammation activity and/or anti-angiogenic activity, the formulation comprising the fumagillol derivative is associated with a block copolymer comprising a hydrophilic polymer moiety and a hydrophobic polymer moiety.

In one embodiment, the MetAP-2 inhibitor is covalently linked to the block copolymer. In one embodiment, the MetAP-2 inhibitor is covalently linked to the hydrophobic polymer moiety of the block copolymer.

In one embodiment, the fumagillol derivative is covalently linked to the block copolymer. In one embodiment, the fumagillol derivative is covalently linked to the hydrophobic polymer moiety of the block copolymer.

In one embodiment, uveitis is T cell-mediated.

In one embodiment, uveitis is associated with an autoimmune related disease or disorder such as diabetes melitis, irritable bowel syndrome, Behcet's disease, Crohn's disease, sarcoidosis etc.

Uveitis encompasses all inflammatory processes of the middle layers of the eye, also called the uveal tract or uvea. The uvea includes the iris (colored part of the eye), choroid (a thin membrane containing many blood vessels) and ciliary body (the part of the eye that joins these together). The uvea is very important because its many veins and arteries transport blood to the parts of the eye that are critical for vision. Uveitis may cause inflammation of all three structures that make up the uvea. Alternately, only one of the structures may be affected. For instance, in the type of uveitis affecting only the iris, the condition is caller iritis, or anterior uveitis. Intermediate uveitis is also known as iridocyclitis, and posterior uveitis is known as choroiditis or chorioretinitis.

As an inflammatory eye condition, uveitis can occur alone or it can occur as part of a generalized inflammatory process in systemic autoimmune diseases. Uveitis can occur as a result of injury, infection (e. g. Lyme disease, tuberculosis, syphilis), or exposure to toxins. Uveitis is often associated with disorders that have an HLA B27 component, such as ankylosing spondylitis and Reiter's disease. Other possible triggers of uveitis include herpes (herpes simplex virus) infection, shingles (varicella-zoster virus), toxoplasmosis, and cytomegalovirus—which occurs mainly in people infected by the human immunodeficiency virus (HIV) and in fungal infections.

Complications of uveitis include visual impairment, vision loss, glaucoma, cataracts, or retinal damage. In the United States, uveitis is responsible for about 10 percent of all cases of blindness.

As an autoimmune disorder, uveitis may occur alone or it may accompany other systemic autoimmune diseases such as rheumatoid arthritis, Bechet syndrome, sarcoidosis, Kawasaki disease, Reiter disease, psoriasis, ulcerative colitis, multiple sclerosis, systemic lupus erythematosus, juvenile idiopathic arthritis, sarcoidosis, diabetes mellitus, inflammatory bowel disease, and/or ankylosing spondylitis.

The most common type of uveitis is anterior uveitis, which represents 75 to 90 percent of all cases, and involves inflammation in the front part of the eye. Anterior uveitis is characterized by flares lasting from a few days to a few weeks with appropriate treatment alternating with relapses. Posterior uveitis is generally a more serious condition, with inflammatory periods lasting as long as a year. In posterior uveitis permanent vision damage may occur even with treatment. Intermediate uveitis (vitritis or plans partitis) is caused by inflammation in the vitreous or fluid portion of the eye.

Symptoms in uveitis are related to which of the uvea's three structures are affected. Symptoms may have a sudden onset, and pain may not necessarily be present. Symptoms include: redness, light sensitivity (photophobia), floaters, blurred vision and pain. A skilled physician in the art would be able to differentially diagnose the condition.

Current treatment options for uveitis include steroid eye drops, injections, or pills taken orally and eye drops that dilate the pupil and reduce pain. In severe cases, chemotherapeutic immunosuppressants are used to suppress the immune system. It is recommended that early treatment be under taken as soon as definitive diagnosis is made to avoid the risk of permanent vision loss. In some embodiments, the method of treatement of uveitis described herein further comprises administering simultaneously any of the conventional treatment options such as steroid eye drops, injections, or pills taken orally and eye drops that dilate the pupil and reduce pain. In some emodiments, chemotherapeutic immunosuppressants are also administered in conjunction with the MetAP-2 inhibitor and/or fumagillol derivative formulation described herein. Ocular inflammation can be graded according to the scoring system described by Ruiz-Moreno et al., Ophthalmic Res. 24:162-168 (1992), which is incorporated herein by reference. The grading scale is as follows: no inflammatory reaction, 0; discrete inflammatory reaction, 1; moderate dilation of the iris and conjunctival vessels, 2; intense iridal hyperemia, with flare in the anterior chamber, 3; and the same clinical signs as grade 3 plus the presence of fibrinoid exudation in the papillary area, with intense flare in the anterior chamber, 4. As used herein, an improvement of one number grade or more is considered effective treatment for uveitis.

In one embodiment of all aspects described herein, MetAP-2 inhibitor is an irreversible MetAP-2 inhibitor.

In one embodiment of all aspects described herein, MetAP-2 inhibitor is a reversible MetAP-2 inhibitor.

In one embodiment of all aspects described herein, the block copolymer is a diblock copolymer.

In one embodiment of all aspects described herein, the formulation comprises a micelle comprising the block copolymer associated with the fumagillol derivative.

In one embodiment of all aspects described herein, the fumagillol derivative thereof is associated with the hydrophobic moiety of the block copolymer.

In one embodiment of all aspects described herein, the hydrophobic polymer moiety of the block copolymer is selected from the group consisting of poly(d,L-lactic acid), poly(L-lysine), poly(aspartic acid), poly(caprolactone) (PCL), poly(propylene oxide).

In one embodiment of all aspects described herein, the hydrophobic moiety is a poly(d,L-lactic acid) (PLA) polymer.

In some embodiments of all aspects described herein, MetAP-2 inhibitor is associated with the PLA moiety of the diblock copolymer.

In one embodiment of all aspects described herein, the hydrophilic polymer moiety of the block copolymer is polyethylene glycol (PEG). In one embodiment of all other aspects described herein, the PEG polymer is a capped PEG polymer.

In one embodiment of all aspects described herein, the block copolymer is a diblock copolymer comprising a PEG-PLA diblock copolymer having hydrophilic PEG and hydrophobic PLA moieties.

In one embodiment of all aspects described herein, the anti-angiogenic activity is an anti-tumor activity.

In one embodiment of all aspects described herein, the fumagillol derivative comprises a derivative selected from the group consisting of 6-O—(N-chloroacetylcarbamoyl) fumagillol (TNP-470), 6-O-(4-methoxyaniline)acetyl fumagillol; 6-O-(3,4, 5-trimethexyaniline)acetyl fumagillol; 6-O-(4-(N,N-dimethylethoxy) aniline)acetyl fumagillol; 6-O-(cyclopropylamino) acetyl fumagillol; 6-O-(cyclobutylamino)acetyl fumagillol; 4-((cyclopropylamino)acetyl) oxy-2-(1,2-epoxy-1,5 20 dimethyl-4-hexenyl)-3-methoxy-1-chloromethyl-1 cyclohexanol; 4-((cyclobutylamino) acetyl) oxy-2-(1,2-epoxy-1,5 dimethyl-4-hexenyl)-3-methoxy-1-chloromethyl-1-cyclohexanol.

In one embodiment of all aspects described herein, the fumagillol derivative comprises 6-O—(N-chloroacetylcarbamoyl) fumagillol (TNP-470).

In one embodiment of all aspects described herein, the formulation comprises a diblock copolymer micelle formed with the diblock copolymer described herein.

In one embodiment of all aspects described herein, the fumagillol derivative is associated with the PLA moiety of the diblock copolymer.

In one embodiment of all aspects described herein, the composition or formulation is administered orally.

In one embodiment of all aspects described herein, the composition or formulation is administered by intravitreous injection. In other embodiments, the composition or formulation is for topical administration, IV administration, peritoneal administration, injection, ocular administration, suppository administration, pulmonary administration or inhalation, and nasal administration.

In one embodiment of all aspects described herein, the composition is administered by intravitreous injection.

Definitions

The term "MetAP-2 inhibitor" refers to an agent that, at a minimum, inhibits the activity of MetAP-2 by at least 20% in a MetAP-2 assay as described in U.S. Pat. No. 6,548,477 or in U.S. Pat. No. 7,030,262 (which are both incorporated herein by reference), preferably at least 50%, at least 60%, at least 70%, at least 80%, at least 90%, at least 95%, at least 96%, at least 97%, at least 98%, at least 99% or more, up to and including complete or 100% inhibition relative to the absence of such an agent. Reversible and irreversible MetAP-2 inhibitors are known in the art and are encompassed by the term "MetAP-2 inhibitor." Fumagillol derivatives as described herein that have anti-proliferative activity are MetAP-2 inhibitors as the term is used herein. The fumagillol and ovacilin classes of MetAP-2 inhibitors have a reactive spiroepoxide moiety that reacts to form a covalent bond with the imidazole nitrogen of histidine 231 in the catalytic site of MetAP-2. Molecular modeling with potential irreversible MetAP-2 inhibitors will permit the skilled artisan to readily predict whether a given candidate inhibitor will react with histidine 231 of the enzyme and therefore have the desired inhibitory activity. Similarly, a rational design approach can be used to prepare reversible MetAP-2 inhibitors, as demonstrated by Wang et al.[43]

The term "fumagillol derivative" encompasses compounds represented by the Formula I below:

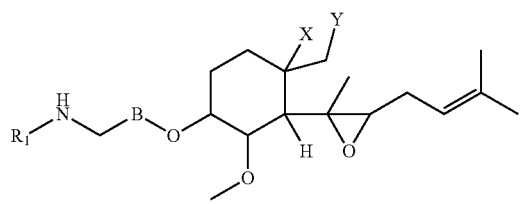

Formula I wherein, X is —OH and Y is halogen, or X and Y are linked together to form a oxyrane ring, B represents —(C=O)— or —CH2-, R1 represents hydrogen, hydroxyl, —CN; NO2, —CF3; formyl; $C_1$-$C_4$ thioalkyl, acetamido; acetoxy; $C_1$-$C_6$ alkyl, $C_1$-$C_4$ aminoalkyl, $C_1$-$C_4$ alkylaminoalkyl; $C_1$-$C_4$ dialkylaminoalkyl; $C_1$-$C_6$ alkyloxy, $C_1$-$C_6$ aminoalkyloxy; $C_1$-$C_4$ alkylaminoalkoyy, $C_1$-$C_4$ dialkylaminoalkoxy, amino; $C_1$-$C_6$ alkylamino; $C_1$-$C_4$ dialkylamino; C1-C4 hyrdoalkyl; $C_1$-$C_4$ alkyloxycarboxylic acid etc. Fumagillol derivatives are disclosed in European Patent Application 0354787, 0357061, and 0415294 and Japanese patent application JP-A01-233275 and U.S. Pat. No. 5,290,807, which are incorporated herein in their entirety by reference. Other MetAP-2 inhibitory fumagillol derivatives, such as PPI-2458, are described by Bernier et al., Proc. Natl. Acad. Sci. U.S.A. 101: 10768-10773 (2004). Fumagillol derivatives as described herein have, at a minimum, anti-angiogenic activity when tested, for example, in a HUVEC proliferation assay as known in the art and described herein below. It should be understood that the term "fumagillol derivative" refers to the derivatives of fumagillol of Formula I, whereas a "fumagillol derivative block copolymer conjugate" refers to such derivatives conjugated to a block copolymer. Similarly, a "MetAP-2 inhibitor" refers to the inhibitor itself, while a "MetAP-2 inhibitor block copolymer conjugate" refers to the MetAP-2 inhibitor conjugated to a block copolymer.

As used herein, the term "proliferation" refers to the development of cells that result in unwanted or undesirable physiological consequences, such as with a tumor or inflammation or hyperpermeable, abnormal vasculature, viral infections, bacterial infections and fungal infections. Angiogenesis should be understood to be a proliferative process. Thus, in certain instances, the term "proliferation" can apply to the development of blood vessels. Such development is also referred to herein as "angiogenesis." In some instances, the term "angiogenesis", as used herein refers to the sprouting of new blood vessels from pre-existing blood vessels, characterized by endothelial cell proliferation and migration triggered by certain pathological conditions, such as the growth of tumors, metastasis, AMD and arthritis, among others. It should be noted that the term "proliferation" can also apply to the proliferation of viruses, bacteria, fungi, microsporidia, etc. The context of the term will make it clear which type of "proliferation" is being referred to.

The term "anti-proliferative activity" refers to the the property of an agent that inhibits, suppresses or reduces the rate of growth or creation of new, undesired cells or blood vessels in the body in order to combat disease. A compound or agent with anti-proliferative activity as used herein is an agent that inhibits MetAP-2 and leads to the suppression of unwanted proliferating cells, e.g., in unwanted angiogenesis, unwanted proliferation of $CD4^+$ T cell, and unwanted proliferation of activated $CD4^+$ T cell. Also encompassed by the term "anti-proliferative activity" is an agent that inhibits MetAP-2 and leads to cell death.

The term "anti-angiogenesis activity" as used herein refers to an agent which inhibits or suppresses or reduces the rate of growth or creation of new blood vessels in the body in order to combat disease. A compound or agent with anti-angiogenesis activity as used herein is an agent capable of inhibiting the formation of blood vessels or the formation of vasculature with abnormal or hyperpermeable properties. A disease associated with vascular permeability includes vascular complications of diabetes such as non-proliferative diabetic retinopathy and diabetic nephropathy, nephrotic syndrome, pulmonary hypertension or fibrosis, burn edema, tumor edema, brain tumor edema, IL-2 therapy-associated edema, and other edema-associated diseases, inflammatory disorders, complications from spinal injury, fibrotic disorders, and infections, including viral infections, bacterial infections and fungal infections.

As used herein, the term "retains anti-proliferative activity" or has anti-proliferative activity" means that a given compound derived from a MetAP-2 inhibitor has at least 20% of the anti-proliferative activity of that MetAP-2 inhibitor. Thus, a given fumagillol derivative will "retain anti-proliferative activity" if it retains at least 20% of the anti-proliferative activity of fumagillol.

As used herein, the term "retains anti-angiogenesis activity" or has anti-angiogenesis activity" means that a given fumagillol derivative has at least 20% of the anti-angiogenic activity of TNP-470 in a HUVEC assay of angiogenesis as described herein.

MetAP-2 inhibitor formulations as described herein can also be used to prevent the leakage of cell proliferation stimulators from blood vessels. That is, MetAP-2 inhibitors can reduce or prevent vascular hyperpermeability, and prevent the accumulation of stimulatory factors at sites of such permeability.

The term "anti-inflammation activity" or "anti-inflammatory activity" as used herein refers to an agent which inhibits, suppresses or reduces the activation of $CD4^+$ T cells, the proliferation of $CD4^+$ T cells, the differentiation of $CD4^+Th0$ cells, the proliferation of activated $CD4^+$ T cells, and/or the cytokine production and/or secretion of pro-activation and pro-proliferation cytokines such as IFN-γ, IL-4, IL-13, TGF-β and transcription factors from $CD4^+$ T cells or activated $CD4^+$ T cells.

As used herein, the term "retains anti-inflammation activity" or "has anti-inflammation activity" means that a given fumagillol derivative has at least 20% of the anti-inflammation activity of TNP-470 in a $CD4^+$ T cell anti-CD3 activation assay as described herein.

As used herein, the terms "activated T cell" and "activation of T cell" refer to the binding of the T cell receptor/CD3 complex of a $CD4^+$ T cell to an antigen or an antibody whereby the receptor transduces the signal intracellularly resulting in increased transcription and protein synthesis for the production and/or secretion of pro-activation and pro-proliferation cytokines such as IFN-γ, IL-4, IL-13, TGF-β and transcription factors, and the proliferation of the activated T cell.

As used herein, the term "inhibit" or "inhibition" means the reduction or prevention of the subject phenomenon. Inhibition includes, for example, slowing the rate of tumor growth and metastasis. The term also refers, for example, to the reduction in ote or more indicia of inflammation or an autoimmune disease or disorder, as measured by methods described herein or known in the art. The one or more indicia can be reduced by about at least 20%, about 30%, about 40%, about 50%, about 60%, about 70%, about 80%, about 90%, about 100%, about 125%, about 150% or more compared to a control, untreated individual or the same individual prior to treatment. The prevention of inflammation or an autoimmune disease or disorder includes no further worsening of symptoms from the time of start of treatment or administration. Prevention also means status quo of substantially no indicia of disease where disease would otherwise be anticipated (e. g. in an untreated individual with a high risk of developing the autoimmune disease).

As used herein, the term "MetAP-2-mediated condition" refers to diseases or disorders in which MetAP-2 activity contributes to the pathology of the condition, whether it involves inappropriate cell proliferation, e.g., inappropriate angiogenesis, or, for example, vascular hyperpermeability resulting from the MetAP-2 activity or from inflammation/autoimmune disease or disorder. While MetAP-2 over-expression or over-activity can be involved, the expression or activity involved in a condition is not necessarily over-expression or over-activity—that is, normal levels of MetAP-2 activity can also contribute to pathological conditions and should be considered a target for therapy in such instances. Examples of conditions in which MetAP-2 activity is involved in or required for the pathology include, but are not limited to cancer, metastatic tumors, psoriasis, age-related macular degeneration (AMD), thyroid hyperplasia, preeclampsia, rheumatoid arthritis and osteo-arthritis, Alzheimer's disease, obesity, pleural effusion, atherosclerosis, endometriosis, diabetic/other retinopathies, ocular neovascularizations, IL-2 therapy associated edema and other edemas, malaria, SARS, HIV, herpes, lupus, IPF, COPD, asthma, cystic fibrosis, transplant rejection, allergic reaction, multiple sclerosis, bacterial infection, viral infection, and conditions involving or characterized by vascular hyperpermeability. Angiogenesis-mediated conditions are a sub-set of MetAP-2-mediated conditions, diseases or disorders that are the direct result of aberrant blood vessel proliferation (e.g. diabetic retinopathy and hemangiomas, among others known in the art and/or discussed herein). Inflammation and autoimmune disease or disorder represent another subset of MetAP-2 mediated conditions.

As used herein, the term "angiogenesis-mediated condition" refers to diseases or disorders that are dependent on a rich blood supply and blood vessel proliferation for the disease pathological progression (eg. metastatic tumors) or diseases or disorders that are the direct result of aberrant blood vessel proliferation (e.g. diabetic retinopathy and hemangiomas). Non-limiting examples include abnormal vascular proliferation, neovascularization, hyperpermeability, ascites formation, psoriasis, age-related macular degeneration, retinopathy, thyroid hyperplasia, preeclampsia, rheumatoid arthritis and osteo-arthritis, Alzheimer's disease, obesity, pleural effusion, atherosclerosis, endometriosis, diabetic/other retinopathies, ocular neovascularizations such as neovascular glaucoma and corneal neovascularization.

As used herein, the term "tumor" means a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic. Tumors are among the angiogenesis-mediated diseases encompassed by the therapeutic methods described herein.

As used herein, the term "tumor" is also used in reference to specific types of tumors, e.g., brain tumors including neuroblastoma, medulloblastoma, meningioma and glioblastoma; head and neck cancer, thyroid carcinoma, endocrine tumors, esophageal cancer, small cell and non-small cell lung cancer, colon cancer, rectal cancer, pancreatic cancer, gastric cancer, bladder cancer, hepatic cancer, malignant lymphoma, acute and chronic leukemia, Kaposi's sarcoma, glioma, hemangioma, osteosarcoma, soft tissue sarcoma, malignant melanoma, skin cancer, prostate cancer, breast carcinoma, choriocarcinoma, ovarian cancer, cervical cancer, uterine cancer and mesenchymal tumors, among others. In the context of the methods and compositions disclosed herein, and as highlighted by the inclusion of lymphomas and leukemias on the list above, it should also be understood that non-solid "tumors" can also benefit from the administration of MetAP-2 inhibitors formulated as described herein.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and generally showing a high degree of anaplasia. Anaplasia is the reversion of cells to an immature or a less differentiated form, and it occurs in most malignant tumors.

The terms "polymersomes" and "polymeric micelles" are used interchangeably herein to refer to the same block copolymer compositions.

The term "copolymer" also known as "heteropolymer" as used herein refers to a polymer derived from two (or more) monomeric species, as opposed to a homopolymer where only one monomer is used. Copolymerization refers to methods used to chemically synthesize a copolymer.

The term "block copolymer" as used herein refers to the polymer comprising more than one subunit (or oligomer) type, wherein the copolymer comprises regions of a polymer comprising one subunit type adjoined to a polymer region comprising a second subunit type, for example the term block copolymer refers to a copolymer comprised of two or more homopolymer subunits linked by covalent bonds. The union of the homopolymer subunits may require an intermediate non-repeating subunit, known as a junction block. Block copolymers are made up of blocks of different polymerized monomers. Block copolymers are interesting because they can "microphase separate" to form periodic nanostructures. Block copolymers are described in further detail in the section "Copolymers" herein below.

The term "diblock copolymer" as used herein refers to a block copolymer with two distinct blocks. A block copolymer with three distinct blocks is called a triblock copolymers. It is also possible to have tetrablocks, multiblocks, etc.

The term "hydrophilic" as used herein refers to a molecule or portion of a molecule that is typically charge-polarized and capable of hydrogen bonding, enabling it to dissolve more readily in water than in oil or other hydrophobic solvents. Hydrophilic molecules are also known as polar molecules and are molecules that readily absorb moisture, are hygroscopic, and have strong polar groups that readily interact with water. A "hydrophilic" polymer as the term is used herein, has a solubility in water of at least 100 mg/ml at 25° C.

The term "hydrophobic" as used herein refers molecules tend to be non-polar and prefer other neutral molecules and non-polar solvents. Hydrophobic molecules in water often cluster together. Water on hydrophobic surfaces will exhibit a high contact angle. Examples of hydrophobic molecules include the alkanes, oils, fats, and greasy substances in general. Hydrophobic materials are used for oil removal from water, the management of oil spills, and chemical separation processes to remove non-polar from polar compounds. Hydrophobic molecules are also known as non-polar molecules. Hydrophobic molecules do not readily absorb water or are adversely affected by water, e.g., as a hydrophobic colloid. A "hydrophobic" polymer as the term is used herein has a solubility in water less than 10 mg/ml at 25° C., preferably less than 5 mg/ml, less than 1 mg/ml or lower.

The term "hydrophobic drug" as used herein refers to any organic or inorganic compound or substance having biological or pharmacological activity and adapted or used for a therapeutic purpose having a water solubility less than 10 mg/ml. MetAP-2 inhibitors, in particular fumagillol derivatives, tend to be hydrophobic drugs.

The term "micelle" as used herein refers to an arrangement of surfactant molecules (surfactants comprise a non-polar, lipophilic "tail" and a polar, hydrophilic "head"). As the term is used herein, a micelle has the arrangement in aqueous solution in which the non-polar tails face inward and the polar heads face outward. Micelles are typically colloid particles formed by an aggregation of small molecules and are usually microscopic particles suspended in some sort of liquid medium, e.g., water, and are between one nanometer and one micrometer in size. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the headgroups at the centre with the tails extending out (water-in-oil micelle). Micelles are approximately spherical in shape. Other phases, including shapes such as ellipsoids, cylinders, and bilayers are also possible. The shape and size of a micelle is a function of the molecular geometry of its surfactant molecules and solution conditions such as surfactant concentration, temperature, pH, and ionic strength. The process of forming micellae is known as micellization.

The term "therapeutically effective amount" refers to an amount that is sufficient to effect a therapeutically or prophylactically significant reduction or measurable suppression of a marker or symptom associated with a disease, condition or disorder dependent upon MetAP-2 activity for its pathology when that amount is administered to a typical subject who has such a condition. A therapeutically or prophylatically significant reduction in a marker or symptom is, e.g. about 10%, about 20%, about 30%, about 40%, about 50%, about 60%, about 70%, about 80%, about 90%, up to and including 100%, i.e., no symptoms or a marker at levels characteristic of non-diseased individuals, as compared to a control or non-treated subject. Alternatively, or in addition, a "therapeutically effective amount" can refer to an amount which directly or indirectly provides a reduction (i.e., at least a 10% reduction, preferably at least 20%, at least 30%, at least 40%, at least 50%, at least 60%, at least 70%, at least 80%, at least 90%, at least 95% or more) in the expression or activity of MetAP-2. In some embodiments where the condition is, for example, cancer, the term "therapeutically effective amount" refers to the amount that is safe and sufficient to prevent or delay the development and further spread of metastases in cancer patients. The amount can also cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastasis.

The term "treat" or "treatment" refer to both therapeutic treatment and prophylactic or preventative measures (prevention is also understood to refer to a reduction in the likelihood of developing disease, e.g., at least a 20% reduced likelihood relative to an individual not receiving the subject treatment), wherein the object is to prevent or slow down the development or spread of disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with disease. Where the disease is, e.g., cancer, those in need of treatment include those likely to develop metastases.

The terms "composition" or "pharmaceutical composition" are used interchangeably herein and refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to oral, IV, peritoneal, injected (e.g., subcutaneous, intramuscular, etc.), eyedrop or ocular, suppository, topical, pulmonary, including inhaled, and nasal routes, among others.

The term "polymeric drug delivery composition" as used herein refers to the combination of drug, and block copolymer.

As used herein, the term "medicament" refers to an agent that promotes the recovery from and/or alleviates a symptom of a relevant condition.

The "pharmaceutically acceptable carrier" means a pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material which solubilizes, stabilizes or otherwise provides a drug formulation with properties necessary to deliver the drug to an individual in a controlled format. A "carrier" can also be involved in carrying or transporting the subject agents from one organ, or portion of the body, to another organ, or portion of the body. Each carrier must be "acceptable" in the sense of being compatible with the other ingredients of the formulation and is compatible with administration to a subject, for example a human. A diblock copolymer as described herein is a pharmaceutically acceptable carrier as the term is used herein. Other pharmaceutically acceptable carriers can be used in combination with the block copolymer carriers as described herein. A pharmaceutically acceptable carrier does not promote the raising of an immune response to the drug.

The terms "polymer solution," "aqueous solution" and the like, when used in reference to a block copolymer contained in such a solution, refer to water, i.e. aqueous, based composition having such block copolymer, or particularly to copolymer conjugates as described herein, such as a MetAP-2 inhibitor-PLA-PEG conjugate dissolved therein at a functional concentration. Polymer solution includes all free flowing forms of the composition comprising the conjugated copolymers as described herein and water. Polymer solutions act to solubilize the drug in a form that is acceptable for administration at physiologically relevant temperatures (temperatures <45° C.).

The term "aqueous solution" as used herein includes water without additives, or aqueous solutions containing additives or excipients such as pH buffers, components for tonicity adjustment, antioxidants, preservatives, drug stabilizers, etc., as commonly used in the preparation of pharmaceutical formulations.

The term "drug formulation" as used herein refers to all combinations of drug with polymer, for example polymer solutions that are mixed with drug to form drug solutions, as well as mixtures of undissolved polymer with drug, i.e. polymeric drug delivery compositions, that are subsequently dissolved into an aqueous environment to form a drug solution.

The term "administration" as used herein refers to the presentation of formulations to humans and animals in effective amounts, and includes all routes for dosing or administering drugs, whether self-administered or administered by medical practitioners. Oral administration is preferred.

The term "biodegradable" as used herein means the block copolymer can chemically break down or degrade within the body to form nontoxic components. The rate of degradation can be the same or different from the rate of drug release.

The term "PLA" as used herein refers to a polymer derived from the condensation of lactic acid or by the ring opening polymerization of lactide.

The term "biodegradable polyesters" as used herein refers to any biodegradable polyesters, which are preferably synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, γ-hydroxy valeric acid, hydroxybutyric acids, malic acid, and copolymers thereof.

As used herein, the term "patient" refers to a mammal, including a human, in need of the treatment to be administered.

The term "subject" and "individual" are used interchangeably herein, and refer to an animal, for example a human, to whom treatment, including prophylactic treatment, with a composition as described herein, is provided. The term "mammal" is intended to encompass a singular "mammal" and plural "mammals," and includes, but is not limited to: humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. Preferably, the mammal is a human subject. As used herein, a "subject" refers to a mammal, preferably a human. The term "individual", "subject", and "patient" are used interchangeably In this specification and the appended claims, the singular forms "a," "an," and "the" include plural references unless the context clearly dictates otherwise. Thus, for example, reference to a composition for delivering "a drug" includes reference to two or more drugs. In describing and claiming the present invention, the following terminology will be used in accordance with the definitions set out below.

As used herein, the term "inhibiting $CD4^+T$ cell activation" refers to inhibiting (as that term is described herein) and/or preventing T-cell proliferation that depends on T-cell receptor (TCR) stimulation. Inhibition a of T cell activation also means preventing or stopping the production and/or secretion of pro-activation and pro-proliferation cytokines such as IFN-$\gamma$, IL-4, IL-13, and TGF-$\beta$, and transcription factors. "Inhibiting $CD4^+T$ cell activation" also inhibiting, preventing or stopping the differentiation of $CD4^+T$ cell as described herein.

As used herein, the term "inhibiting graft-versus-host disease" refers to substantially preventing the T-cell activation and the T-cell mediate immune response to the donor graft which can lead to the destruction and/scarring of donated tissue such that the donated tissue cannot function or functions at less than 50% efficiency in the host. Inhibiting in this context also refers to reducing and ameliorating by at least 20% or more the symptoms associated with the disease such as swelling, inflammation, pain, and fever.

"Oral" administration includes oral, enteral or intragastric administration. Inhalation administration can also accomplish a tolerizing effect in autoimmune disease.

"Parenteral" administration includes subcutaneous, intradermal, intramuscular, intravenous, intraperitoneal or intrathecal administration.

Administration "in conjunction with" encompasses simultaneous and sequential administration, as well as administration in combined form or separately.

MetAP-2 Inhibitors

There are a number of MetAP-2 inhibitors known in the art, and MetAP-2 inhibitors of any kind are contemplated for formulation and use as described herein. That is, it is specifically contemplated herein that any of them can beneficially be prepared as block copolymer conjugates for delivery to a subject to treat a disease, disorder or condition related to, associated with or requiring MetAP-2 activity for its pathology. MetAP-2 inhibitors formulated as described herein retain anti-proliferative activity—that is, a MetAP-2 inhibitor formulated with a block copolymer conjugate as described herein will retain a meaningful portion of the anti-proliferative (including, but not limited to anti-angiogenic) activity of the inhibitor alone as measured in a MetAP-2 assay as described herein.

More specifically, however, MetAP-2 inhibitors including, but not limited to fumagillol derivatives, ovalicin, anthranilic acid sulfonamides (Wang et al., Proc. Natl. Acad. Sci. U.S.A. 105: 1838-1843 (2008)) e.g., A-800141, beng-amides, bestatins (including, but not limited to reversible MetAP-2 inhibitors such as A-357300 and others described by Wang et al., Cancer Res. 63: 7861-7869), triazoles (see, e.g., compounds described in U.S. Pat. No. 7,303,082, and compounds described, e.g., by Garrabrant et al., Angiogenesis 7: 91-96 (2004)), 3-amino-2-hydroxyamides, hydroxyamides and acylhydrazines are contemplated for use in the formulations and methods described herein.

MetAP-2 inhibitors of various classes are described, for example, in U.S. Pat. Nos. 7,348,307, 7,268,111, 7,157,420, 7,105,482, 7,084,108, 7,037,890, 6,919,307, 6,548,477, 6,242,494, 6,288,228, 6,849,757, 6,887,863, 4,831,135, 7,122,345 and 7,030,262 and in U.S. published Patent Applications 20070254843, 20070161570, 20070117758, 20070010452, 20060223758, 20060069028, 20050239878, 20050059585, 20030109671, 20020193298, and 20020151493, the disclosures of each of which are incorporated herein by reference. Each of the MetAP-2 inhibitors described is potentially suitable for formulation as a MetAP-2 inhibitor block copolymer conjugate as described herein, for the treatment of MetAP-2 associated diseases, disorders or conditions.

Figure 15:
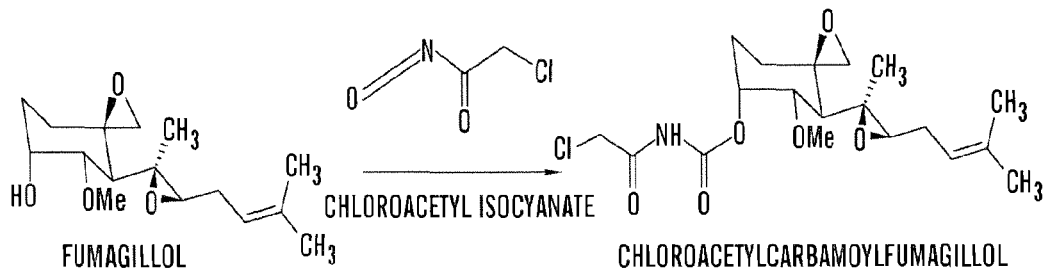
FIG. 15 shows schematics of exemplary approaches for functionalizing MetAP-2 inhibitors and coupling copolymers to them.
Figure 15:
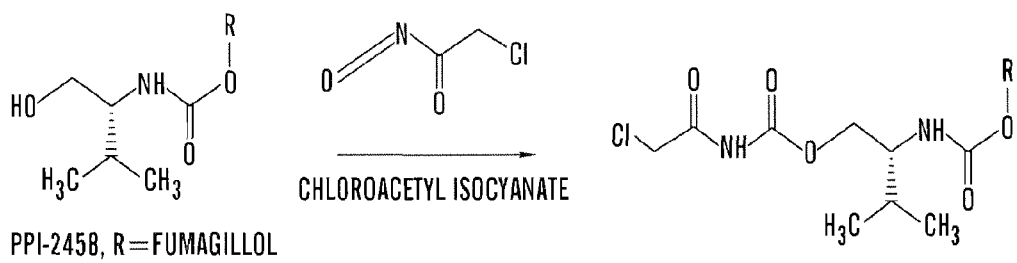
Figure 15:
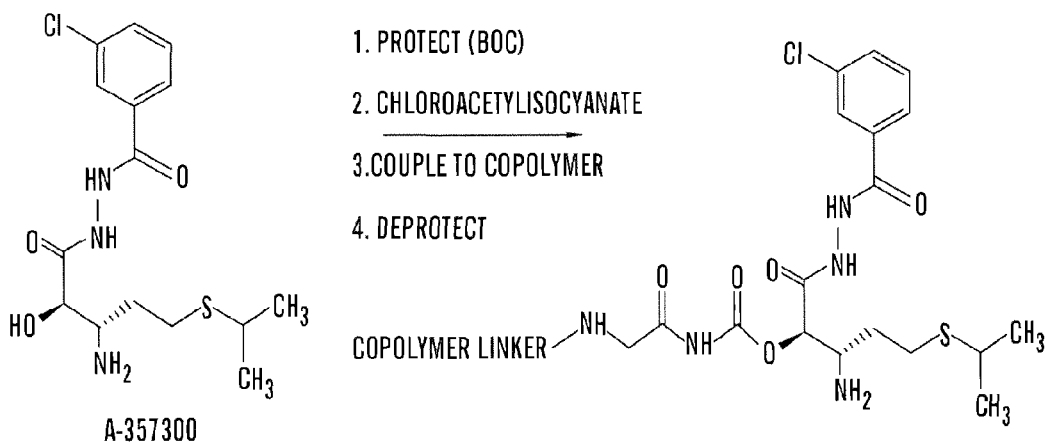

Standard chemical approaches known to those of skill in the art can be used to conjugate a MetAP-2 inhibitor to block copolymer to generate a composition as described herein; the specific approach will depend upon the type of MetAP-2 inhibitor selected. For example, MetAP-2 inhibitors with alcohol functionality can be coupled to PEG-PLA using the same type of synthesis used to functionalize fumagillol (e.g., reaction with chloroacetylisocyanate, followed by reaction with a polymer bearing primary amine functionality). As an example, the compound A-357300 can be coupled in this manner after amine protection. See, e.g., FIG. 15. Similar coupling for can also be used, for example, to couple compounds such as (1-hydroxymethyl-2-methyl-propyl)-carbamic acid -(3R, 4S, 5S, 6R)-5-methoxy-4-[(2R,3R)-2-methyl-3-(3-methyl-but-2-enyl)-oxiranyl]-1-oxa-spiro[2.5] oct-6-yl ester (see U.S. Pat. No. 6,548,477). Additional fumagillin derivatives with alcohol functionalities permitting such conjugation are described, for example, in U.S. Pat. No. 7,087,768 (Han et al.)—see, e.g., Example 35 therein.

Assays for MetAP-2 activity are also known in the art. Assays are described, for example in U.S. Pat. Nos. 6,548, 477 and 7,030,262. Any such assay can be used to evaluate the MetAP-2 inhibitory activity of a given compound or the activity of a given MetAP-2 inhibitor block copolymer conjugate as described herein. For the avoidance of doubt, however, a MetAP-2 inhibitor will demonstrate MetAP-2 inhibition (by at least 20%, preferably by at least 50%, at least 60%, at least 70%, at least 80%, at least 90%, at least 95%, up to and including 100% (complete inhibition)) at a dosage or concentration that is substantially not toxic to the cells or subject to which it is to be administered, in either of the following two MetAP-2 assays.

Recombinant human MetAP-2 is expressed and purified from insect cells as described in Li and Chang, (1996) Biochem. Biophys. Res. Commun. 227:152-159. Various amounts of candidate MetAP-2 inhibitor compound are then added to buffer H (10 mM Hepes, pH 7.35, 100 mM KC 1, 10% glycerol, and 0.1 M $Co^{2+}$) containing 1 nM purified recombinant human MetAP-2 and incubated at 37° C. for 30 minutes. To start the enzymatic reaction, a peptide containing a methionine residue, e.g., Met-Gly-Met, is added to the reaction mixture to a concentration of 1 mM. Released methionine is subsequently quantified at different time points (e.g., at 0, 2, 3, and 5 minutes) using the method of Zou et al. (1995) Mol. Gen Genetics 246:247-253). MetAP-2 inhibition is scored relative to a control lacking the candidate inhibitor, and can also be scored relative to a known MetAP-2 inhibitor, e.g. TNP-470 or, for example, TNP-470 block copolymer conjugate as described herein.

Assays for the inhibition of catalytic activity of MetAP-2 can be performed in 96-well microtiter plates. Compounds to be tested are dissolved in dimethyl sulfoxide at 10 mM and diluted ten-fold in assay buffer (50 mM HEPES, pH 7.4, 100 mM NaCl). Ten microliters of solution of each compound to be tested for inhibition are introduced into each cell of the plate. Zero inhibition of enzyme activity is taken to be the result obtained in cells in which 10 mL of assay buffer was placed. A mixture totaling 90 mL per well and made up of 84 mL of assay buffer containing 100 mM $MnCl_2$, 1 mL of L-amino acid oxidase (Sigma Catalog No. A-9378, ~11 mg/mL), 1 mL of horseradish peroxidase (Sigma Catalog No. P-8451, dissolved in assay buffer at a concentration of 10 mg/mL), 1 mL of the tripeptide Met-Ala-Ser (Bachem) dissolved in assay buffer at concentration of 50 mM, 1 mL of ortho-dianisidine (Sigma Catalog No. D-1954, freshly made solution in water at a concentration of 10 mg/mL), and MetAP-2 at a final concentration of 1.5 mg/mL are rapidly mixed and added to each cell containing test or control compound. The absorbence at 450 nanometers is measured every 20 seconds over a period of twenty minutes using an automatic plate reader (e.g., from Molecular Devices, California, USA). The Vmax in mOD/min, calculated for each well, is used to represent MetAP-2 activity. The $IC_{50}$ for each candidate inhibitor is obtained by plotting the remaining activity versus inhibitor concentrations.

It is noted that some pro-drugs may require pre-treatment (e.g., enxymatic or non-specific hydrolysis) before assaying for MEtAP-2 inhibitory activity.

Fumagillol Derivatives

As one class of MetAP-2 inhibitors, derivatives of fumagillol are formulated for oral administration in compositions and methods described herein. It should be understood that anywhere in which the instant description refers to a MetAP-2 inhibitor, it can also be said to be referring to a fumagillol derivative having anti-proliferative and anti-angiogenic activity. Fumagillol derivatives useful in the compositions and methods described herein retain anti-proliferative, including, but not limited to anti-angiogenic, activity—i.e., at least 50% of the anti-proliferative activity of TNP-470, as measured in a HUVEC assay (see below). Numerous fumagillol derivatives meeting this criterion are known in the art. In one embodiment, suitable fumagillol derivatives for use in the compositions and formulations as disclosed herein are described in U.S. Pat. No. 5,290,807 which is incorporated herein in its entirety by reference.

In other embodiments, suitable fumagillol derivatives for use in the compositions and formulations as disclosed herein are representative of general Formula II as disclosed in U.S. Pat. Nos. 5,166,172; 5,290,807; 5,180,738 and 5,164,410, which are hereby incorporated by reference. In further embodiments, fumagillol derivatives for use in the compositions and formulations as disclosed herein are listed in International Patent Application WO03/027104 which is incorporated herein in its entirety by reference.

In one embodiment, a fumagillol derivative is 6-O—(N-chloroacetylcarbamoyl) fumagillol, also known as TNP-470, a derivative of the fumagillol of Formula III of International Patent Application WO03/027104 shown below.

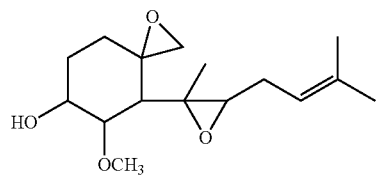

Formula III

The structures of fumagillin and 6-O—(N-chloroacetylcarbamoyl) fumagillol (TNP-470) are shown below:

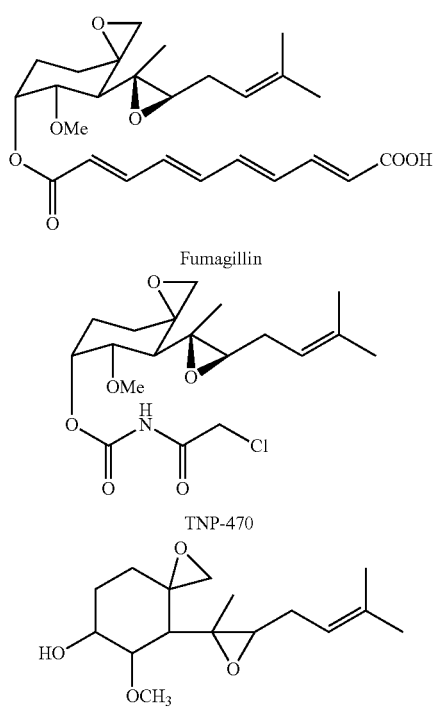

The synthesis of TNP-470 is disclosed in U.S. Pat. Nos. 5,180,738 and 5,290,807 which are hereby incorporated herein in their entirety by reference.

Fumagillin has been disclosed to be anti-proliferative and to have anti-angiogenic activity in U.S. Pat. No. 5,135,919 which is incorporated herein in its entirety by reference. Moreover, various fumagillol derivatives have been disclosed to be anti-proliferative and to have anti-angiogenic activity in U.S. Pat. Nos. 5,180,738; 5,164,410; 5,196, 406; 5,166,172; and 5,290,807 which are incorporated herein in their entirety by reference. Other MetAP-2 inhibitory fumagillol derivatives, such as PPI-2458, are described by Bernier et al., Proc. Natl. Acad. Sci. U.S.A. 101: 10768-10773 (2004), which is incorporated herein by reference. In particular, one fumagillol derivative (3R,4S,5S,6R)-5-methoxy-4-(2R, 3R)-2-methyl-3-(3-methyl-2-butenyl)-oxiranyl)-1-oxaspiro(2,5)oct-6-yl(chloroacetyl) carbamate, also known as 6-O—(N-chloroacetylcarbamoyl) fumagillol or TNP-470 (available from Takeda Chemical Industries, Ltd. of Japan) is a particularly potent anti-proliferative and anti-angiogenic compound. Bhargava et al. review TNP-470 in Chapter 26 of Angiogenesis in Health and Disease, G. M. Rubanyi, ed., Marcel/Dekkker: 2000, pp. 387-406. One can determine if a fumagillol derivative has anti-proliferative activity using a proliferation assay as described herein. Similarly, where the proliferation involves angiogenesis, anti-angiogenic activity can be measured using an angiogenesis assay as shown in the Examples or as disclosed herein.

In some embodiments, fumagillol derivatives include, for example, but not limited to, O-(3,4-dimethoxycinnamoyl) fumagillol; O-(4-methoxycinnamoyl) fumagillol; O-(3,4,5-trimethoxycinnamoyl)fumagillol; O-(4-Chlorocinnamoyl) fumagillol; 4-(3,4,5-trimethoxycinnamoyl)oxy-2-(1,2-epoxy-1,5-dimethyl-4-hexenyl)-3-methoxy-1-chloromethyl-1-cyclohexanol; O-(4-trifluoromethylcinnamoyl)fumagillol; O-(4-nitrocinnamoyl)fumagillol; O-(3, 4-dimethoxy-6-nitrocinnamoyl)fumagillol; O-(4-acetoxycinnamoyl) nimagillol; O-(4-hydroxycinnamoyl)fumagillol; O-(4-acetoxy-3,5-dimethoxycinnamoyl) fumagillol; O-(3,5-dimethoxy-4-hydroxycinnamoyl)fumagillol; 4-(4-methoxycinnamoyl)oxy-2-(1,2-epoxy-1,5-dimethyl-4-hexenyl)-3-methoxy-1-chloromethyl-1-cyclohexanol; O-(4-dimethylaminocinnamoyl)fumagillol; O-(4-aminocinnamoyl)fumagillol; O-(4-cyanocinnamoyl) fumagillol; O-(3,4,5-trimethoxycinnamyl)fumagillol; O-(4-dimethylaminoethoxycinnamyl) fumagillol; O-(3-dimethylaminomethyl-4-methoxycinnamoyl)fumagillol; O-(3, 4-methylenedioxycinnamoyl)fumagillol; O-(3,4-dimethoxy-6-aminocinnamoyl) fumagillol; O-(4-ethylaminocinnamoyl)fumagillol; O-(4-ethylaminoethoxycinnamoyl) fumagillol; O-(4-dimethylaminocinnamyl) fumagillol; and 4-(4-dimethylaminocinnamoyl)oxy-2-(1,2-epoxy-1,5-dimethyl-4-hexenyl)-3-methoxy-1-chloromethyl-1-cyclohexanol.

In some embodiments, fumagillol derivatives include derivatives of the formula I, for example, but are not limited to: 1) 6-O-(4-methoxyaniline)acetyl fumagillol; 2) 6-O-(3,4,5-trimethoxyaniline)acetyl fumagillol; 3) 6-O-(2,4-dimethexyaniline)acetyl fumagillol; 4) 6-O-(3,4-dimethoxyaniline)acetyl fumagillol; 5) 6-O-(3,4-dimethoxy-6-nitroaniline)acetyl 5 fumagillol; 6) 6-O-(3,4-dimethexy-6-cyaneaniline)acetyl fumagillol; 7) 6-O-(4-allyloxyaniline) acetyl fumagillol; 8) 6-O-(4-(2-acetoxyethexy)aniline) acetyl fumagillol; 9) 6-O-(3-cyano-4-methoxyaniline)acetyl fumagillol; 10) 6-O-(3-(dimethylaminomethyl)-4-methexyaniline) acetyl fumagillol; 11) 6-O-(4-(2-methylpropoxyaniline)acetyl fumagillol; 12) 6-O-(3-isopropoxy-4-methoxyaniline)acetyl 15 fumagillol; 13) 6-O-(4-(N,N-dimethylethoxy)aniline)acetyl fumagillol; 14) 6-O-(3,5-diisopropyl-4-methoxyaniline)acetyl fumagillol; 15) 6-O-(3,5-dimethyl-4-methoxyaniline)acetyl fumagillol; 16) 6-O-(3-isopropyl-4-ethoxy-6-methylaniline)acetyl fumagillol; 17) 6-O-(4-propyloxyaniline)acetyl fumagillol; 18) 6-c-(aniline)acetyl fumagillol; 19) 6-O-(4-chloroaniline)acetyl fumagillol; 20) 6-O-(4-dimethylaminoaniline)acetyl fumagillol; 21) 6-O-(4-hydroxyaniline)acetyl fumagillol; 22) 6-O-(4-aminoaniline)acetyl fumagillol; 23) 6-O-(3,4-methylenedioxyaniline)acetyl fumagillol; 24) 6-O-(4-nitroaniline)acetyl fumagillol; 25) 6-O-(2,3,4-trimethoxy-6-aminoaniline)acetyl fumagillol; 26) 6-0-(4-acetoxy-3,5-dimethoxyaniline) acetyl fumagillol; 27) 6-0-(3, 4-dimethoxy-5-hydroxyaniline)acetyl fumagillol; 28) 6-O-(4-dimethylaminoethoxyaniline)acetyl fumagillol; 29) 6-O-(4-ethylaminoaniline)acetyl fumagillol; 30) 6-O-(4-ethylaminoethoxyaniline) acetyl fumagillol; 31) 6-O-(3-dimethylaminomethyl-4 methoxyaniline)acetyl fumagillol; 32) 6-O-(4-trifluoromethylaniline) acetyl fumagillol; 33) 6-O-(4-acetoxy aniline) acetyl fumagillol; 34) 6-O-(4-cyanoaniline)acetyl fumagillol; 35) 6-O-(4-hydroxyethoxyaniline) acetyl fumagillol; 36) 6-O-(5-amino-2-methoxypyridine)acetyl fumagillol; 37) 6-O-(5-methoxypyrimidine-2-amino) acetyl fumagillol; 38) 6-o-(3-methoxy-6-aminopyridazine)acetyl fumagillol; 39) 4-((4-methoxyaniline)acetyl)oxy-2-(1,2-epoxy-1,5 dimethyl-4-hexenyl)-3-methoxy-1-chloromethyl-1 cyclohexanol; 40) 4-((3,4,5-trimethoxyaniline) acetyl)oxy-2-(1,2 5 epoxy-1,5-dimethyl-4-hexenyl)-3-methoxy-1-chloromethyl-1 cyclohexanol; 41) 6-O-(ethylamino)acetyl fumagillol; 42) 6-O-(isopropyl amino) acetyl fumagillol; 43) 6-O-(1-propyl amino) acetyl fumagillol; 44) 6-O-(1-butyl amino)acetyl fumagillol; 45) 6-O-(sec-butyl amino)acetyl fumagillol; 46) 6-O-(2-methyl-butylamino)acetyl fumagillol; 47) 6-O-(t-butyl amino)acetyl fumagillol; 48) 6-O-(pentyl amino)acetyl fumagillol; 49) 6-O-(1-methyl-butyl amino)acetyl fumagillol; 50) 6-O-(1-ethyl-propyl amino)acetyl-fumagilloli; 51) 6-O-(1-methyl-pentylamino)acetyl fumagillol; 52) 6-O-(1,2-dimethyl-butylamino) acetyl fumagillol; 53) 6-O-(1,2,2-trimethyl-propylamino)acetyl 20 fumagillol; 54) 6-O-(1-isopropyl-2-methylpropylamino)acetyl fumagillol; 55) 6-O-(3-methylbutylamino)acetyl fumagillol; 56) 6-O-(2-methylallylamino) acetyl fumagillol; 57) 6-O-(4-methyl-hepta-2,4-dienylamino)acetyl fumagillol; 58) 6-O-(1,5-dimethyl-4-hexenylamino)acetyl fumagillol; 59) 6-O-(1,1-dimethyl-2-propynylamino)acetyl fumagillol; 60) 6-O-(prop-2-enylamino) acetyl fumagillol; 61) 6-O-(2-bromoethylamino)acetyl fumagillol; 62) 6-O-(chloroethynylamino)acetyl fumagillol; 63) 6-O-(cyclopropylamino)acetyl fumagillol; 64) 6-O-(cyclobutylamino)acetyl fumagillol; 65) 6-O-(cyclopentylamino)acetyl fumagillol; 66) 6-O-(cyclohexylamino)acetyl fumagillol; 67) 6-O-(4-tert-butylcyclohexylamino)acetyl fumagillol; 68) 6-O-(2-dimethylamino-1-methylethylamino)acetyl 15 fumagillol; 69) 6-O-(2-dimethylamino-propylamino)acetyl fumagillol; 70) 6-O-(2-methexy-2-methyl-propylamino)acetyl fumagillol; 71) 6-O-(2-oxo-propylamine) acetyl fumagillol; 72) 6-O-(1,1-dimethyl-3-oxobutylamino)acetyl fumagillol; 73) 6-O-(ethyl-2-aminoacetate)acetyl fumagillol; 74) 6-O-(alanine-methylesteramino)acetyl fumagillol; 75) 6-O-(methyl-2-amino-3,3-dimethylbutanoate)acetyl fumagillol; 76) 6-O-(allylglycine-methylester)acetyl fumagillol; 77) 6-O-(2,2-dimethexy-ehtylamino)acetyl fumagillol; 78) 4-((cyclopropylamino)acetyl) oxy-2-(1,2-epoxy 1,5-dimethyl-4-hexenyl)-3-methoxy-1-chloromethyl-1 5 cyclohexanol; 79) 4-((cyclobutylamino)acetyl)oxy-2-(1,2-epoxy-1,5-: dimethyl-4-hexenyl)-3-methoxy-1-chloromethyl-1-1 cyclohexanol; and 80) 6-O-(chloro)acetyl fumagillol.

Among the compounds of the Formula I, fumagillol derivatives useful in the methods and compositions as disclosed herein include, for example, but are not limited to 1) 6-O-(4-methoxyaniline)acetyl fumagillol; 2) 6-O-(3,4,5-trimethexyaniline)acetyl fumagillol; 3) 6-O-(4-(N,N-dimethylethoxy) aniline)acetyl fumagillol; 4) 6-O-(cyclopropylamino) acetyl fumagillol; 5) 6-O-(cyclobutylamino)acetyl fumagillol; 6) 4-((cyclopropylamino)acetyl) oxy-2-(1,2-epoxy-1,5 20 dimethyl-4-hexenyl)-3-methoxy-1-chloromethyl-1 cyclohexanol; and 7) 4-((cyclobutylamino)acetyl) oxy-2-(1,2-epoxy-1,5 dimethyl-4-hexenyl)-3-methoxy-1-chloromethyl-1-cyclohexanol. Structural formulas of the above compounds are shown in Tables in International Patent Application No: WO03/027104, which is incorporated herein by reference.

To enhance the activity of anti-proliferative or anti-angiogenic treatments, use of adjunct treatments with MetAP-2 inhibitors, including fumagillol derivatives, can be performed. Thus in one embodiment, use of the compositions as disclosed herein including a MetAP-2 inhibitor block copolymer conjugate in conjunction with other agents is encompassed in the present invention for treatment of diseases, disorders or conditions associated with, characterized by, or otherwise requiring MetAP-2 activity for their pathologies. These include, but are not limited to diseases involving abnormally stimulated neovascularization, such as inflammatory diseases (rheumatism and psoriasis, among others), diabetic retinopathy and cancer.

Copolymers

One aspect of the invention relates to the use of copolymers as carriers for the solubilization and formulation of a MetAP-2 inhibitor, for example TNP-470, as disclosed herein. A copolymer is a polymer comprising subunits of more than one type, i.e a copolymer can comprise subunits of A and subunits of B etc. In some embodiments, a copolymer is an alternating copolymer, for example, having a repeating structure comprising the different types of subunits, for example an alternating copolymer can have the formula: -A-B-A-B-A-B-A-B-A-B-, or -(-A-B-)$_n$-.

In some embodiments, MetAP-2 inhibitors as disclosed herein are associated with a block copolymer to form a MetAP-2 inhibitor-block copolymer conjugate.

The polymers useful in the compositions and methods described herein are block copolymers. A block copolymer comprises subunits of more than one type, but instead of an alternating copolymer, a block copolymer comprises at a minimum, a block of subunits of one subunit type followed by a block of subunits of another subunit type. For example, a block copolymer comprising two subunits, for example A and B can have the formula of: -(A-A-)$_n$-(B-B-)$_n$- or -A-A-A-A-A-B-B-B-B-B-. The number of the different subunits can be different, for example; A-A-A-A-B-B-B-B-B. A diblock copolymer is a block copolymer comprising two different blocks of polymer subunits, whereas a triblock copolymer is a block copolymer comprising three different blocks of polymer subunits, and a tretrablock copolymer is a block copolymer comprising four different blocks of copolymer subunits, etc.

Figure 14:
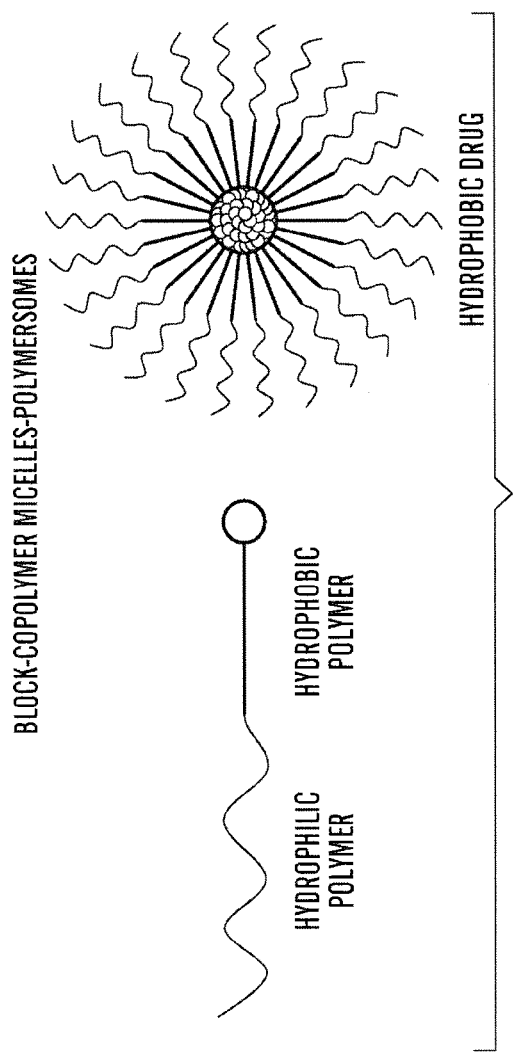
FIG. 14 shows schematic drawings of diblock-copolymer that is part hydrophilic and part hydrophobic conjugated to MetAP-2 inhibitors and diblock-copolymer micelles (polymersomes) formed.

As used herein, a block copolymer is a polymer comprising at least a first block comprising a polymer of hydrophobic monomers, and at least a second block comprising a polymer comprised of hydrophilic monomers (see FIG. 14). A "block" copolymer differs from a non-block copolymer in that a block copolymer comprises blocks of polymer of one type (e.g. a block of hydrophilic monomers) that are joined to a block of polymer of another type (e.g. a block of hydrophobic monomers), as opposed to a non-block copolymer in which the different monomers are not joined together in blocks. For example, for a block copolymer of monomers A and B, the block copolymer would have, e.g., the structure AAAAABBBBB. A non-block copolymer of the same monomer subunits would have, for example, the structure ABAABABBABAABB or the structure ABABABABABAB, for example. The blocks of a block copolymer as the term is used herein will have at least 5 monomers per block (i.e., for a block copolymer of A and B monomers, the A block will be at least 5 A monomers long, and the B block will be at least 5 B monomers long). In some embodiments the homopolymer blocks will be at least 10 monomers long, 15 monomers long, 20 monomers long or more. A block copolymer as the term is used herein can have different block lengths (but each block will be at least 5 monomers long)—differences in block lengths can influence the ability of the block copolymer to form certain structures, e.g., micelles. In some instances, the monomers making up the hydrophilic block of a block copolymer can comprise different hydrophilic monomer subunits, and similarly, in some embodiments, monomers making up the hydrophobic block of a block copolymer can comprise different hydrophobic monomer subunits.

Diblock copolymers can be made using living polymerization techniques, such as atom transfer free radical polymerization (ATRP), reversible addition fragmentation chain transfer (RAFT), ring-opening metathesis polymerization (ROMP), and living cationic or living anionic polymerizations.

Block copolymers can "microphase separate" to form periodic nanostructures, for example, when one block is hydrophobic and the other hydrophilic. Microphase separation is a situation similar to that of oil and water. Oil and water don't mix together—they macrophase separate. If you have an "oil-like" first block and a "water-like" second block, the block copolymers undergo microphase separation. The blocks want to get as far from each other as possible, but they are covalently bonded, so they're not going to get very far. In "microphase separation" the "oil" and "water" blocks form nanometer-sized structures, including micelles, which comprise essentially spherical arrangement with the hydrophilic blocks arrange to the outside of the sphere, in contact with an aqueous solution and the hydrophobic blocks forming an inner hydrophobic core. Thermodynamic terms can describe how the different blocks interact. The interaction parameter, "chi" gives an indication of how different, chemically, the two blocks are and whether or not they will microphase separate. Generally, if the product of chi and the molecular weight is large (greater than 10.5), the blocks will microphase separate. Conversely, if the product of chi and the molecular weight is too small (less than 10.5), the different blocks are able to mix, rather than microphase separate.

In some embodiments, amphiphilic block copolymers are useful in the formulations and compositions of the present invention, for example as effective drug carriers that solubilize hydrophobic drugs into an aqueous environment. For example, amphiphilic block copolymers exhibiting self-association properties are disclosed in EP No. 0397 307 and EP0583955 and EP0552802, which are incorporated herein by reference.

In some embodiments, useful biodegradable polyesters comprised by the hydrophobic block of copolymers described herein are, for example, biodegradable polyester oligomers or polymers synthesized from monomers selected from, e.g., D, L-lactide, D-lactide, L-lactide, D, L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydroxybutyric acids, malic acid, and copolymers thereof. More preferably, the biodegradable polyester is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof. Most preferably, the biodegradable polyester is synthesized from monomers selected from the group consisting of D, L-lactide, D-lactide, L-lactide, D, L-lactic acid, D-lactic acid, L-lactic acid, glycolide, glycolic acid, and copolymers thereof.

In some embodiments, the block copolymers comprise hydrophobic polyesters containing polyester bonds, for example but not limited to polylactic acid (PLA), polyglycolic acid (PGA), poly(D,L-lactic-co-glycolic acid)(PLGA), poly(caprolactone), poly(valerolactone), poly(hydroxybutyrate) and poly(hydroxyvalerate).

In some embodiments, the block copolymers comprise hydrophobic polymers, for example of said block copolymer is selected from the group consisting of poly(d,L-lactic acid), poly(L-lysine), poly(aspartic acid), poly(caprolactone) (PCL), poly(propylene oxide). In some embodiments, a hydrophobic polymer moiety is 1-15 kDa. For example, a hydrophobic polymer moiety is between 0.5-10 kDa, 1-8 kDa, 1-5 kDa, 1-3 kDa, 3-15 kDa, 5-15 kDa, 8-15 kDa, 10-15 kDa, 12-15 kDa, 2-12 kDa, 4-10 kDa, 6-8 kDa in size. In some embodiments, a hydrophobic polymer is approximately 2 kDa, for example 1.5 kDa, 2 kDa, or 2.5 kDa. In particular embodiments, a hydrophobic moiety useful in the composition as disclosed herein is a poly(d,L-lactic acid) (PLA) polymer, for example a poly(d,L-lactic acid) (PLA) polymer of lkDa (1000 Da).

In some embodiments, the copolymers comprise hydrophilic polymers, for example but not limited to polyethene glycol (PEG) polymer (which is also referred to a poly(ethylene oxide) (PEO) or poly(oxyethelene) in the art). In some embodiments, the hydrophillic polymer may be capped at one end. In some embodiments, the capping group is alkoxy. For example, a hydrophilic polymer useful in the composition as disclosed by be capped with a methoxy group. In some embodiments, a hydrophilic polymer is between 1-15 kDa. For example, a hydrophilic polymer moiety useful in the composition as disclosed is between 1-10 kDa, 1-8 kDa, 1-5 kDa, 1-3 kDa, 3-15 kDa, 5-15 kDa, 8-15 kDa, 10-15 kDa, 12-15 kDa, 2-12 kDa, 4-10 kDa, 6-8 kDa in size. In some embodiments, a hydrophilic polymer is approximately 2 kDa, for example 1.5 kDa, 2 kDa, or 2.5 kDa. In particular embodiments, a hydrophilic polymer is a poly(ethylene glycol) (PEG) polymer, for example a poly(ethylene glycol) (PEG) polymer of 2 kDa (2000 Da).

In some embodiments, the copolymers comprise a diblock copolymer comprising a PEG-PLA diblock copolymer, where block copolymer comprises blocks of the hydrophilic PEG monomers and blocks of the hydrophobic monomer PLA.

The hydrophilic blocks of a copolymer can be coupled to the hydrophobic blocks by covalent bonds, for example by ester or urethane links and the like. Condensation polymerization and ring opening polymerization procedures may be utilized as may the coupling of a monofunctional hydrophilic block to either end of a difunctional hydrophobic block in the presence of coupling agents such as isocyanates. Furthermore, coupling reactions may follow activation of functional groups with activating agents, such as carbonyl diimidazole, succinic anhydride, N-hydroxy succinimide and p-nitrophenyl chloroformate and the like.

In some embodiments, hydrophilic blocks of a copolymer can comprise PEG or derivatized PEG monomers of an appropriate molecular weight. PEG has particularly favorable biocompatibility, nontoxic properties, hydrophilicity, solubilization properties, and rapid clearance from a patient's body.

The hydrophobic blocks of a copolymer should also comprise biodegradable polyester momomers that are biodegradable and biocompatible. The in vitro and in vivo degradation of hydrophobic, biodegradable polyester blocks of a copolymer are well understood and the degradation products are readily metabolized and/or eliminated from the patient's body.

MetAP-2 inhibitors, including fumagillol derivatives, such as TNP-470, can be solubilized or dispersed using block copolymers as disclosed herein. One advantage of using the block copolymers as disclosed herein is that the MetAP-2 inhibitors such as TNP-470 that have limited solubility or dispersibility in an aqueous or hydrophilic environment have enhanced solubility and/or dispersibility and can be administered via oral administration. Another advantage of using the block copolymer is improved biodistribution versus the bengamide class of MetAP-2 inhibitors, or the sulphonamide class, or the bestatin class of inhibitors.

One can prepare block copolymer, MetAP-2 conjugates as micelles as disclosed in the Examples herein. In another embodiment, one can prepare block copolymer micelles for sustained release of a MetAP-2 inhibitor using the method is disclosed in U.S. Pat. No. 6,623,729, which is incorporated in its entirety herein by reference and is further illustrated in the following steps:

Step 1: Preparation of Block Copolymer. A block copolymer containing a hydrophobic part having hydroxyl group at one end and a hydrophilic part at the other end is prepared by copolymerization of a biodegradable polyester polymer and a polyethylene glycol (PEG) polymer in the presence of stannous octate as a catalyst: The copolymerization is performed at 160-200.quadrature for 2-6 hours under a vacuum condition. The polyester polymer includes polylactic acid (PLA), polyglycolic acid (PGA), poly(D,L-lactic-co-glycolic acid)(PLGA), poly(caprolactone), poly(valerolactone), poly(hydroxy butyrate) or poly(hydroxy valerate), and in some embodiments PLA and methoxypolyethyleneglycol is used as the polyethyleneglycol polymer.

Step 2: Binding of Linker by an Activation of Functional Groups of Block Copolymer. The block copolymer is dissolved in an organic solvent and reacted with a linker at room temperature in the presence of pyridine and nitrogen: The organic solvent includes, but without limitation, methylenechloride, and the linker includes p-nitrophenyl chloroformate, carbonyldiimidazole (CDI), N,N'-disuccinimidyl carbonate (DSC), or a mixture of these compounds, preferably p-nitrophenyl chloroformate. The reaction is carried out for 2 to 6 hours, with a molar ratio of block copolymer: linker:pyridine ranging from 1:2:2 to 1:2:6.

Step 3: Preparation of a Conjugate of Drug and Biodegradable Polymer. The linker-bound block copolymer is conjugated to a drug by covalent linkage to obtain a micelle monomer of a conjugate of drug and block copolymer, where the block copolymer obtained by reacting with hydrazine may be used: The block copolymer reacted with hydrazine forms a micelle monomer by binding the linker to a ketone group of a MetAP-2 inhibitor, such as a fumagillol derivative, while the block copolymer without hydrazine reaction forms a micelle monomer by binding the linker to an amine group of a MetAP-2 inhibitor, such as a fumagillol derivative. Preferably, the MetAP-2 inhibitor is TNP-470. In alternative embodiments, other MetAP-2 inhibitors are equally suitable for copolymer conjugation. In yet another embodiment, other drugs or chemotherapeutic agents are used in addition to a MetAP-2 inhibitor, for example anticancer agents such as, but without limitation, doxorubicin, adriamycin, cisplatin, taxol and 5-fluorouracil.

Step 4: Preparation of Sustained Release Micelle. The micelle monomers prepared in Step 3 are dispersed in an aqueous solution to prepare sustained release micelles. When micelle monomers are dispersed in a certain concentration, micelles are formed spontaneously by thermodynamic equilibrium. Sustained release micelles thus prepared release a drug by way of hydrolysis and enzymatic action in vivo, and the released drug exerts the same effect as free drug does.

Conjugation of MetAP-2 Inhibitors with Copolymers

In the composition and methods disclosed herein, a MetAP-2 inhibitor, for example TNP-470, is associated with a block copolymer.

As used herein, the term "associated with" means that one entity is in physical association or contact with another. Thus, a MetAP-2 inhibitor "associated with" a block copolymer can be either covalently or non-covalently joined to the block copolymer. It is preferred that the association be covalent. The association can be mediated by a linker moiety, particularly where the association is covalent. The term "association" or "interaction" or "associated with" are used interchangeably herein and as used in reference to the association or interaction of a MetAP-2 inhibitor, e.g., TNP-470 with a block copolymer, refers to any association between the MetAP-2 inhibitor and the block copolymer, for example a diblock copolymer comprising a hydrophilic polymer moiety and a hydrophobic polymer moiety, either by a direct linkage or an indirect linkage.

An indirect linkage includes an association between a MetAP-2 inhibitor and the block copolymer, wherein said a MetAP-2 inhibitor and block copolymer are attached via a linker moiety, e.g., they are not directly linked. Linker moieties include, but are not limited to, chemical linker moieties. In some embodiments, a linker between the MetAP-2 inhibitor and the copolymer is formed by reacting the polymer and a linker selected e.g., from the group consisting of p-nitrophenyl chloroformate, carbonyldiimidazole (CDI), N,N'-disuccinimidyl carbonate (DSC), cis-aconitic anhydride, and a mixture of these compounds.

A direct linkage includes any linkage wherein a linker moiety is not required. In one embodiment, a direct linkage includes a chemical or a physical interaction wherein the two moieties, i.e. the a MetAP-2 inhibitor and the block copolymer interact such that they are attracted to each other. Examples of direct interactions include covalent interactions, non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, a MetAP-2 inhibitor, such as TNP-470 and the block copolymer are not linked via a linker, e.g., they are directly linked. In a further embodiment, a MetAP-2 inhibitor and the block copolymer are electrostatically associated with each other.

In one embodiment, the linker is a peptide linker. In another embodiment, the peptide linker is enzymatically cleavable, e.g., by a protease enzyme that cleaves the linkage to release the MetAP-2 inhibitor. Most preferably, the peptide linkage is capable of being cleaved by preselected cellular enzymes, for instance, those found in lysosomes of cancerous cells or proliferating endothelial cells. Alternatively, an acid hydrolysable linker could comprise an ester or amide linkage and be for instance, a cis-aconityl linkage. A pH sensitive linker can also be used. Cleavage of the linker of the conjugate results in release of active MetAP-2 inhibitor. Thus the MetAP-2 inhibitor must be conjugated with the polymer in a way that does not alter the activity of the agent. The linker preferably comprises at least one cleavable peptide bond. Preferably the linker is an enzyme cleavable oligopeptide group preferably comprising sufficient amino acid units to allow specific binding and cleavage by a selected cellular enzyme. Preferably the linker is at least two amino acids long, more preferably at least three amino acids long. Cleavable linkers are described, e.g., in U.S. Pat. No. 7,332,523, which is incorporated herein by reference. An example of a preferred peptide linker is Gly-Phe-Leu-Gly (see U.S. Pat. No. 7,332,523). Other linker are known to those of skill in the art.

Pharmaceutical Compositions and Administration:

The MetAP-2 inhibitor in the formulations and compositions as disclosed herein is particularly useful in methods of treating conditions in which MetAP-2 activity is involved in or required for the pathology of the condition, including, but not necessarily limited to conditions in which MetAp-2 is either over-expressed or over-active in a mammal, for example a human. Such conditions, herein also referred to as a "MetAP-2-dependent disease or disorder" are selected from a group including, but not necessarily limited to cancer, angiogenic disease or disorder, autoimmune or inflammatory disease or disorder, ascites formation, psoriasis, age-related macular degeneration, uveitis, thyroid hyperplasia, preeclampsia, rheumatoid arthritis and osteoarthritis, Alzheimer's disease, obesity, pleura effusion, atherosclerosis, endometriosis, diabetic/other retinopathies, neovascular glaucoma, age-related macular degeneration, hemangiomas, and corneal neovascularization, HIV, HPV, herpes and other viral infections, anthrax, IPF, COPD, multiple sclerosis, other sclerotic diseases, transplant rejection, lupus, asthma and other conditions described herein as associated with MetAP-2 activity.

In one embodiment, a MetAP-2-dependent disease or disorder is cancer, where the cells are rapidly dividing neoplastic cancer cells, and where the neoplastic cells require an efficient blood supply to maintain continued growth of the tumor. As used herein, cancer refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of a MetAP-2 inhibitor in the formulations and compositions as disclosed herein is useful to inhibit proliferation at the primary disease site, and in the case of cancer, at secondary tumor sites; embodiments of the invention serve to prevent and limit the progression of the disease. Any disease that requires a continuous proliferation of cells, either primary cells, endothelial cells, adjacent cells or others in order to perpetuate the disease is a candidate target. For example, candidates for the treatment of cancer as described herein include, but are not limited to carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In one embodiment, a MetAP-2-dependent disease or disorder is age-related macular degeneration. It is known that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. In order for new blood vessels to grow (neovascularization) beneath the retina and leak blood and fluid, endothelial cells must proliferate. This proliferation is uneven, and results in the leakage described above, which causes permanent damage to light-sensitive retinal cells, which die off and create blind spots in central vision or the macula.

In one embodiment, a MetAP-2-dependent disease or disorder is diabetic retinopathy—abnormal blood vessel growth associated with diabetic eye diseases. In diabetic retinopathy and retinopathy of prematurity (ROP) VEGF is released which promotes blood vessel formation—thus, the disease or disorder is an angiogenic disease or disorder. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels, having proliferated too quickly and unevenly, are faulty, so they leak, bleed and encourage scar tissue that detaches the retina, resulting in severe loss of vision. Such growth is the hallmark of diabetic retinopathy, the leading cause of blindness among young people in developed countries. In one embodiment, the subject in need of treatment can be a mammal, such as a dog or a cat, preferably a human.

In one embodiment, a MetAP-2-dependent disease or disorder is rheumatoid arthritis.[44] Rheumatoid arthritis (RA) is characterized by synovial tissue swelling, leukocyte ingress and new blood vessel growth from existing vessels. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Endothelial cell proliferation is now recognized as a key event in the formation and maintenance of the pannus in RA (Paleolog, E. M., 2002). Thus, RA is an angiogenesis-related disease or disorder. Even in early RA, some of the earliest histological observations are blood vessels. A mononuclear infiltrate characterizes the synovial tissue along with a luxuriant vasculature. Endothelial cell proliferation is integral to formation of the inflammatory pannus and without it, leukocyte ingress could not occur (Koch, A. E., 2000). Disruption of the formation of new blood vessels would not only prevent delivery of nutrients to the inflammatory site, it could also reduce joint swelling due to the additional activity of VEGF, a potent proangiogenic factor in RA, as a vascular permeability factor.

In one embodiment, a MetAP-2-dependent disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with an anti-proliferative effects, seem to prevent Alzheimer's disease and/or influence the outcome of AD patients. Therefore, it has been speculated that in AD endothelial cell proliferation in the brain vasculature may play an important role in AD, that is, AD can be an angiogenesis-related or -mediated disease. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-proliferative or anti-angiogenic strategies can interfere with endothelial cell activation in AD (Schultheiss C., el. al., 2006; Grammas P., et. al., 1999) and can be used for preventing and/or treating AD.

In one embodiment, a MetAP-2-dependent disease or disorder is obesity. It has been shown that the MetAP-2 inhibitor TNP-470 was able to prevent diet-induced and genetic obesity in mice (Ebba Brakenhielm et. al., Circulation Research, 2004; 94:1579). TNP-470 reduced vascularity in the adipose tissue, thereby inhibiting the rate of growth of the adipose tissue and obesity development. Obesity is thus an angiogenesis-related or -mediated disease or disorder.

In one embodiment, a MetAP-2-dependent disease or disorder is endometriosis. Excessive endometrial angiogenesis is proposed as an important mechanism in the pathogenesis of endometriosis (Healy, D L., et. al., 1998). The endometrium of patients with endometriosis shows enhanced endothelial cell proliferation. Moreover there is an elevated expression of the cell adhesion molecule integrin vβ3 in more blood vessels in the endometrium of women with endometriosis when compared with normal women. Strategies that inhibit endothelial cell proliferation can be used to treat endometriosis.

The MetAP-2 inhibitor in the formulations and compositions as disclosed herein is particularly useful in methods of inhibiting cell proliferation, including angiogenesis at a site of tumorigenesis in a mammal[45] and proliferation of T cells. The MetAP-2 inhibitor in the formulations and compositions as disclosed herein administered at such sites and in such varied ways prevents or inhibits endothelial cell proliferation and blood vessel formation at the site thereby inhibiting the development and growth of the tumor. The MetAP-2 inhibitor in the formulations and compositions as disclosed herein can also be administered at inflammation sites and in such varied ways prevents or inhibits proliferation of T cells and for the suppression of T cell differentiation.

In some embodiments, the compositions as disclosed herein comprise a MetAP-2 inhibitor that inhibits proliferation of blood vessel endothelial cells, thus having anti-angiogenesis effect or inhibition of angiogenesis. Accordingly, the compositions as disclosed herein comprising MetAP-2 inhibitors can be used in methods for treating angiogenesis-mediated conditions in which MetAP-2 is involved in the pathology, such as inhibiting growth and metastasis of cancer as well as treating other various diseases where inappropriate angiogenesis occurs or proliferation of blood vessel endothelial cells occur, for example but not limited to, inflammatory diseases, autoimmune diseases, diabetic retinopathy, rheumatoid arthritis, and psoriasis. Accordingly, the compositions comprising MetAP-2 inhibitors as disclosed herein can be used as a cancer metastasis inhibitor or therapeutic agent against cancer, autoimmune or inflammatory diseases, uveitis, diabetic retinopathy, rheumatoid arthritis, psoriasis and other retinopathies such as retinopathy of prematurity.

Actual dosage levels of active ingredients in the pharmaceutical compositions as described herein can be varied so as to obtain an amount of the active compound(s) which is effective to achieve the desired therapeutic response for a particular subject or patient. The selected dosage level will depend upon the activity of the particular MetAP-2 inhibitor, the type of administration composition (i.e. tablet versus liquid oral administration versus ocular versus topical versus inhaled, for example), the severity of the condition being treated and the condition and prior medical history of the patient being treated.

The phrase "therapeutically effective amount" of a compound, e.g., a MetAP-2 inhibitor as described herein means a sufficient amount of the compound to treat disorders, at a reasonable benefit/risk ratio applicable to any medical treatment. It will be understood, however, that the total daily usage of the compositions and formulations as disclosed herein will be decided by the attending physician within the scope of sound medical judgment. A "therapeutically effective amount" as the term is used herein need not eradicate a disease. Rather, a therapeutically effective amount will at least slow progression of a disease (as non-limiting example, the growth of a tumor or neoplasm) relative to progression without the therapeutic agent, for example the composition as disclosed herein comprising a MetAP-2-block copolymer conjugate. Thus, it is preferred, but not required that the therapeutic agent actually eliminate the disease.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the compositions and formulations as disclosed herein which are employed; and like factors well known in the medical arts. For example, it is well within the skill of the art to either start doses of the compound at levels lower than required to achieve the desired therapeutic effect and to gradually increase the dosage until the desired effect is achieved, or start doses of the compound at high levels and to gradually decrease the dosage until the desired effect is achieved, as appropriate for the care of the individual patient.

The compositions as disclosed herein can also be administered in prophylatically or therapeutically effective amounts. The formulations and compositions as disclosed herein can be administered along with a pharmaceutically acceptable carrier. A prophylatically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

The term "effective amount" as used herein refers to the amount of therapeutic agent of pharmaceutical composition to alleviate at least some of the symptoms of the disease or disorder. The term "effective amount" includes within its meaning a sufficient amount of pharmacological composition to provide the desired effect. The exact amount required will vary depending on factors such as the type of disease or disorder to be treated, the severity of the disease or disorder, the potential drug resistance level of the disease or disorder, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation.

Efficacy of treatment can be judged by an ordinarily skilled practitioner. As disclosed in the Examples, efficacy can be assessed in animal models of disease or disorder, for example treatment of a rodent with a model disease or disorder, and any treatment or administration of the compositions or formulations that leads to a decrease of at least one symptom of the disease or disorder, for example an inhibiton or reduction in the indicia of uveitis in the model described herein indicates effective treatment.

In addition, the amount of each component to be administered also depends upon the frequency of administration, such as whether administration is once a day, twice a day, 3 times a day or 4 times a day, once a week; or several times a week, for example 2 or 3, or 4 times a week.

As an example only, TNP-470 administration will be described in greater detail as a representative example of the administration procedures for all MetAP-2 inhibitors in general. For 6-O—(N-chloroacetylcarbamoyl)fumagillol (TNP-470), the following information may serve as a general guideline for administration. Usually, the formulations and compositions as disclosed herein are administered from once a day to several times a day, for example 2 times a day, three times a day, or four times a day. In alternative embodiments, the formulations and compositions as disclosed herein can be administered, for example three to five times a week, if it is to be plurally administered in a given week. In some modes of administration, e.g., IV administration, it is desirable to dose less frequently, e.g., weekly or biweekly; block copolymer conjugate compounds can be useful in such a regimen.

For example, in one embodiment a suitable dose of the MetAP-2 inhibitor in the formulations and compositions as disclosed herein for a subject in need of treatment can be used according to conventionally used dose ranges of about 1 mg to about 2000 mg TNP-470 equivalent per kilogram of body weight. Generally however, conventional doses of fumagillol derivatives are about 0.1 mg/kg to 40 mg/kg body weight, preferably about 0.5 mg/kg to 20 mg/kg body weight as disclosed in U.S. Pat. No. 5,290,807. In alternative embodiments, where maintenance of suppression of disease or disorder is the goal (e. g. autoimmune or inflammatory disease or disorder), a dose below the threshold used for immunosuppressive therapy or chemotherapy for the initial treatment of acute disease can be used. For example, a suitable dose could be less than the conventionally used chemotherapeutic dose, for example, dose ranges of about 1 µg to 1 mg or 0.1 µg to 1 mg, or 1 mg to 10 mg TNP-470 per kilogram of body weight can be used.

In some embodiments, if TNP-470 is administered once a week, it can be administered in an amount of from about 20 to about 200 mg/m$^2$/week; preferably in an amount of from about 40 to about 180 mg/m$^2$/week; and most preferably in an amount of from about 135 to about 175 mg/m$^2$/week. In some embodiments, if TNP-470 is administered daily, it may be administered in an amount of from about 1 to about 10 mg/m$^2$/day; for example in an amount of from about 1.25 to about 5 mg/m$^2$/day; or in an amount of from about 1 to about 3 mg/m$^2$/day. For continuous administration, the component is usually administered for at least five consecutive days of the week. In some embodiments, the effective amount of a composition as disclosed herein comprising a fumagillol derivative can be determined using an anti-angiogenesis assay as disclosed herein, and in some embodiments, the effective amount is less than the amount used as the conventionally effective dose. Alternatively, where applied to an autoimmune disease, for example, a cytokine release array (e. g. an ELISA) can be used to determine the dose at which inhibition of T cells cytokine occurs. Similar dosage regimes can be applied for formulations of other MetAP-2 inhibitor compositions as disclosed herein.

In an alternative embodiment, higher dosages can be used, provided there is not unacceptable toxicity. For example, dosages in the range of about 50 to about 500 mg/m$^2$/week or more, and sub-ranges within this range are specifically contemplated. Thus, dosages in the range of about 120 to 350 mg/m$^2$/week, 200 to 400 mg/m$^2$/week, etc. are specifically contemplated.

The preferred route of administration of the compositions and formulations as disclosed herein is oral administration. Solid dosage forms for oral administration include, for example but not limited to capsules, tablets, pills, powders and granules. In such solid dosage forms, the compositions as disclosed herein may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The active components can also be in micro-encapsulated form, if appropriate, with one or more of the above-mentioned excipients. In the preparation of pharmaceutical formulations as disclosed herein in the form of dosage units for oral administration the compound selected can be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons*, 21st Ed. The compositions can also be inhaled (pulmonary, nasal), ocular (eyedrop), sub-lingual, suppository, or topical (e.g., an ointment).

To enhance the activity of anti-inflammtory or autoimmune treatments, use of adjunct treatments is contemplated. In particular, MetAP-2 inhibitors such as TNP-470 have been tested in conjunction with treatment with various other drugs to enhance efficacy for treatment of diseases induced by abnormally stimulated neovascularization, such as inflammatory diseases (rheumatism and psoriasis among others), diabetic retinopathy, cancer and other diseases and conditions as discussed elsewhere herein.

Soft gelatin capsules can be prepared with capsules containing a mixture of the active compound or compounds of the invention in vegetable oil, fat, or other suitable vehicle for soft gelatin capsules. Hard gelatin capsules can contain granules of the active compound. Hard gelatin capsules can also contain the targeted delivery composition including the targeting moiety and the carrier particle as well as the therapeutic agent in combination with solid powdered ingredients such as lactose, saccharose, sorbitol, mannitol, potato starch, corn starch, arnylopectin, cellulose derivatives or gelatin.

Liquid dosage forms for oral administration include pharmaceutically acceptable emulsions, solutions, suspensions, syrups and elixirs. In addition to the active components, the liquid dosage forms may contain inert diluents commonly used in the art such as, for example, water or other solvents that are compatible with the maintenance of a micelle of a diblock copolymer as described herein. Liquid preparations for oral administration can also be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol provided that such solvent is compatible with maintaining the micelle form. If desired, such liquid preparations can contain coloring agents, flavoring agents, saccharin and carboxymethyl cellulose or other thickening agents. Liquid preparations for oral administration can also be prepared in the form of a dry powder to be reconstituted with a suitable solvent prior to use.

Besides inert diluents, the oral compositions may also include adjuvants such as wetting agents, emulsifying and suspending agents, sweetening, flavoring and perfuming agents Transdermal patches may also be used to provide controlled delivery of the formulations and compositions as disclosed herein to specific regions of the body. Such dosage forms can be made by dissolving or dispensing the component in the proper medium. Absorption enhancers can also be used to increase the flux of the compound across the skin.

The rate can be controlled by either providing a rate-controlling membrane or by dispersing the compound in a polymer matrix or gel. Such transdemal patches are useful for treating parts of the body where abnormally stimulated neovascularization or inflammation occurs, such as inflammatory diseases, for example, uveitis, rheumatism and psoriasis among others, or other skin related inflammatory or autoimmune disease or disorder.

A further form of topical administration is to the eye, for example as a treatment for retinopathy, such as diabetic retinopathy or retinopathy of prematurity (ROP) or for the treatment of immune-mediated conditions of the eye such as autoimmune diseases, e. g. uveitis, allergic or inflammatory conditions, and corneal transplants. Components of the formulation described herein can be delivered in a pharmaceutically acceptable ophthalmic vehicle, such that the component is maintained in contact with the ocular surface for a sufficient time period to allow the component to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment or an encapsulating material.

In an alternative embodiment, the compositions and formulations as disclosed herein can be also administered via rectal or vaginal administration. In such embodiments, the compositions and formulations as disclosed herein can be in the form of suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active component.

Dosage units for rectal or vaginal administration can be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

To further protect the active ingredient, the MetAP-2 inhibitor-copolymer conjugates described herein can be used in admixture or in combination with a gastric acid secretion-inhibitor and/or an antacid.

Gastric acid secretion inhibitors include, for example $H_2$ blockers (e.g. famotidine, cimetidine, ranitidine hydrochloride, etc.) and proton pump inhibitors (e.g. lansoprazole, omeprazole, etc.). As an antacid, compounds which elevate the intragastric pH level, such as magnesium carbonate, sodium hydrogen carbonate, magnesium hydroxide, magnesium oxide and magnesium hydroxide can be employed. The oral dosage forms of the compositions and formulations as disclosed herein can be administered after the intragastric pH has been increased to alleviate the influence of gastric acid by the administration of a gastric acid secretion inhibitor and/or antacid.

Alternatively, compositions and formulations as disclosed herein can be in a form of enteric-coated preparation for oral administration comprising a MetAP-2 inhibitor-block copolymer conjugate. In some embodiments, an MetAP-2 inhibitor containing core for coating with an enteric coating film can be prepared using an oleaginous base or by other known formulation methods without using an oleaginous base. In some embodiments, the compositions and formulations as disclosed herein in the form of the drug-containing core for coating with a coating agent may be, for example, tablets, pills and granules.

The excipient contained in the core is exemplified by saccharides, such as sucrose, lactose, mannitol and glucose, starch, crystalline cellulose and calcium phosphate. Useful binders include polyvinyl alcohol, hydroxypropyl cellulose, macrogol, Pluronic F-68, gum arabic, gelatin and starch. Useful disintegrants include carboxymethyl cellulose calcium (ECG505), crosslinked carboxymethylcellulose sodium (Ac-Di-Sol), polyvinylpyrrolidone and low-substituted hydroxypropyl cellulose (L-HPC). Useful lubricants and antiflocculants include talc and magnesium stearate.

The enteric coating agent is an enteric polymer which is substantially insoluble in the acidic pH and is at least partially soluble at weaker acidic pH through the basic pH range. The range of acidic pH is about 0.5 to about 4.5, preferably about 1.0 to about 2.0. The range of weaker acidic pH through basic pH is about 5.0 to about 9.0, preferably about 6.0 to about 7.5. Specifically, cellulose acetate phthalate, hydroxypropylmethylcellulose phthalate, hydroxypropylmethyl acetate succinate (Shin-Etsu Chemicals), methacrylic copolymers (Rhon-Pharma, Eudragit® L-30D-55, L100-55, L100, S100, etc.), etc. can be mentioned as examples of the enteric coating agent. These materials are effective in terms of stability, even if they are directly used as enteric compositions.

In the case of forming micelles, for example, spherical microparticles having particle diameters of about 0.01 μm to about 1000 μm are generated, or more preferably about 0.01 to about 5 μm (about 10 nm to about 5,000 nm). This formation can be performed by the methods as disclosed in the Examples or as disclosed in Japanese Patent Application JP-A-223533/1991. In some embodiments, micelles between 50 and 500 nm are useful in the compositions as disclosed herein, for example about 50-100 nm, 100-150 nm, 150-200 nm, 200-250 nm, 250-300 nm, 300-350 nm, 350-400 nm, 450-500 nm. In some embodiments, the micelles are about 130 nm as disclosed in the examples.

The concentration or content of the MetAP-2 inhibitor in the composition can be appropriately selected according to the physicochemical properties of the composition. When the composition is in a liquid form, the concentration is about 0.0005 to about 30% (w/v) and preferably about 0.005 to about 25% (w/v). When the composition is a solid, the content is about 0.01 to about 90% (w/w) and preferably about 0.1 to about 50% (w/w).

If necessary, additives such as a preservative (e.g. benzyl alcohol, ethyl alcohol, benzalkonium chloride, phenol, chlorobutanol, etc.), an antioxidant (e.g. butylhydroxyanisole, propyl gallate, ascorbyl palmitate, alpha-tocopherol, etc.), and a thickener (e.g. lecithin, hydroxypropylcellulose, aluminum stearate, etc.) can be used in the compositions and formulations as disclosed herein.

It is noted that diblock copolymer conjugates as described generally need no further emulsifiers. Nonetheless, if necessary, one can use an additional emulsifier with the compositions and formulations as disclosed herein. Examples of emulsifiers that might be used include pharmaceutically acceptable phospholipids and nonionic surfactants. The emulsifiers can be used individually or in combinations of two or more. The phospholipid includes naturally occurring phospholipids, e.g. egg yolk lecithin, soya lecithin, and their hydrogenation products, and synthetic phospholipids, e.g. phosphatidylcholine, phosphatidylethanolamine, etc. Among them, egg yolk lecithin, soya lecithin, and phosphatidylcholine derived from egg yolk or soybean are preferred. The nonionic surfactant includes macro-molecular surfactants with molecular weights in the range of about 800 to about 20000, such as polyethylene-propylene copolymer, polyoxyethylene alkyl ethers, polyoxyethylene alkylarylethers, hydrogenated castor oil-polyoxyethylene derivatives, polyoxyethylene sorbitan derivatives, polyoxyethylene sorbitol derivatives, polyoxyethylene alkyl ether sulfate, and so on. The proportion of the emulsifier is selected so that the concentration in a final administrable composition will be in the range of about 0.1 to about 10%, preferably about 0.5 to about 5%.

In addition to the above-mentioned components, a stabilizer for further improving the stability of the compositions and formulations as disclosed herein, such as an antioxidant or a chelating agent, an isotonizing agent for adjusting the osmolarity, an auxiliary emulsifier for improving the emulsifying power, and/or an emulsion stabilizer for improving the stability of the emulsifying agent can be incorporated. The isotonizing agent that can be used includes, for example, gylycerin, sugar alcohols, monosaccharides, disaccharides, amino acids, dextran, albumin, etc. These isotonizing agents can be used individually or in combination, with two or more. An emulsion stabilizer that can be used, which includes cholesterol, cholesterol esters, tocopherol, albumin, fatty acid amide derivatives, polysaccharides, polysaccharide fatty acid ester derivatives, etc.

The compositions and formulations as disclosed herein can further comprise a viscogenic substance which can adhere to the digestive tract mucosa due to its viscosity expressed on exposure to water. The examples of the viscogenic substance include, but are not particularly limited as long as it is pharmaceutically acceptable, such as polymers (e.g. polymers or copolymers of acrylic acids and their salts) and natural-occurring viscogenic substances (e.g. mucins, agar, gelatin, pectin, carrageenin, sodium alginate, locust bean gum, xanthan gum, tragacanth gum, arabic gum, chitosan, pullulan, waxy starch, sucralfate, curdlan, cellulose, and their derivatives). Furthermore, for controling the release of the active drug or for formulation purposes, the additives conventionally used for preparing the oral compositions can be added. Example of the additives include excipients (e.g. lactose, corn starch, talc, crystalline cellulose, sugar powder, magnesium stearate, mannitol, light anhydrous silicic acid, magnesium carbonate, calcium carbonate, L-cysteine, etc.), binders (e.g. starch, sucrose, gelatin, arabic gum powder, methylcellulose, carboxymethylcellulose, carboxymethylcellulose sodium, hydroxypropylcellulose, hydroxypropylmethylcellulose, polyvinylpyrrolidone, pullulan, dextrin, etc.), disintegrators (e.g. carboxymethylcellulose calcium, low-substituted hydroxypropylcellulose, croscarmellose sodium, etc.), anionic surfactants (e.g. sodium alkylsulfates etc.), nonionic surfactants (e.g. polyoxyethylene sorbitan fatty acid esters, polyoxyethylene fatty acid esters, polyoxyethylene-castor oil derivatives, etc.), antacids and mucous membrane protectants (e.g. magnesium hydroxide, magnesium oxide, aluminum hydroxide, aluminum sulfate, magnesium metasilicate aluminate, magnesium silicate aluminate, sucralfate, etc.), cyclodextrin and the corresponding carboxylic acid (e.g. maltosyl-beta-cyclodextrin, maltosyl-beta-cyclodextrin-carboxylic acid, etc.), colorants, corrigents, adsorbents, antiseptics, moistening agents, antistatic agents, disintegration retardants, and so on. The proportion of these additives can be appropriately selected from the range that can keep the stability and absorption of the basis.

The compositions and formulations as disclosed herein for oral administration of the present invention may also include flavoring agents. Such agents include, for example, anise oil, lavender oil, lemon oil, orange essence, rose oil, powder green tea, bergamot oil, (alpha[liter]) borneol, Natural Peal Extract AH-10, Sugar, bitter essence, pine flavor etc.

In the case of forming micelles, for example, spherical microparticles having particle diameters of about 0.1 nm to about 1000 nm, this formation can be achieved by methods known in the art (e.g. JP-A-223533/1991). In some embodiments, micelles between 50 and 500 nm are useful in the compositions as disclosed herein, for example about 50-100 nm, 100-150 nm, 150-200 nm, 200-250 nm, 250-300 nm, 300-350 nm, 350-400 nm, 450-500 nm. In some embodiments, the micelles are about 130 nm as disclosed in the examples.

The compositions and formulations as disclosed herein can exhibit potent pharmacological activity with low toxicity such that they are useful as a medicament for prevention and treatment for, interalia, MetAP-2-associated disease in mammals (e.g. mouse, rat, monkey, bovine, canine, human, etc.), said MetAP-2-associated disease including, for example, (1) autoimmune or inflammatory diseases such as uveitis, rheumatoid arthritis, (2) diabetic retinopathy, and (3) benign and malignant tumors and fibrotic diseases such as idiopathic pulmonary fibrosis, or cystic fibrosis. It is particularly useful when the dosage form of the compositions and formulations as disclosed herein insures an effective blood concentration within the range not causing expression of the side effects of the active substance in prolonged time, or not contributing to new side effects due to prolonged blood circulation or depoting in organ tissue for lack of renal or other clearance mechanism.

Generally, no enteric coating is required for the fumagillol-derivative diblock copolymer formulations described herein to be orally effective. It can be advantageous, however, from the standpoint of stability, that the compositions and formulations as disclosed herein are filled into capsule shells coated with an enteric coating agent as mentioned above for use as an enteric composition. As the capsule shell, for example, soft capsules (e.g. the product of R. P. Sealer) and hard gelatin capsules are used.

The liquid or solid compositions and formulations as disclosed herein can be administered orally. In the case of the liquid form, it can be directly administered e.g., by drinking an elixir or suspension of the composition, or alternatively, into the digestive tract via a catheter or sonde for oral administration or administered in the usual manner in the unit dosage form of a hard capsule or a soft capsule. In the case of the solid form, it can be administered orally as powders, capsules, tablets, or the like in the usual manner. It can also be redispersed in a suitable dispersion medium and administered in a liquid form. Taking a patient with uveitis (body weight: 50 kg) as but one example, the oral dose of the composition as disclosed herein is about 1 mg to about 3 g/day, preferably about 10 mg to about 1 g/day, of a MetAP-2 inhibitor. In some embodiments, the oral dose of the composition as disclosed herein is between the ranges of about 25 mg to about 1 g/day, and in some embodiments less than 25 mg to 1 g/day, for example about 10 mg to about 0.5 g/day, of a MetAP-2 inhibitor.

The compositions and formulations as disclosed herein enhance biodistribution, stability and uptake properties of MetAP-2 inhibitors and increase the pharmacological activity thereof, so that better assurance of therapeutic efficacy is achieved without the need for parenteral administration. The dosage form of the compositions and formulations as disclosed herein is stable and exhibits remarkable inhibiting activity on proliferative activity in oral administration so that it can be used as clinically advantageous oral medicine.

Suspensions, in addition to the active components, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In one embodiment, the delivery is by intranasal administration of the composition, especially for use in therapy of the brain and related organs (e.g., meninges and spinal cord). Along these lines, intraocular administration is also possible. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

In another embodiment, the formulations described herein can be administered in conjunction with an anti-VEGF agent. Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by *Aspergillus fumigates*.

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./ Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (iEterna Zentaris Inc; Quebec City, Calif.) and combinations thereof.

In yet another embodiment, the methods described herein encompass combination therapy in which the formulations and compositions as disclosed herein are used in combination or conjunction with therapeutics, physiotherapy, other immunosuppressive therapy and/or behavioral psychotherapy such as those used in the treatment of autoimmune or inflammatory disease, rheumatoid arthritis, obesity, endometriosis, idiopathic pulmonary fibrosis (IPF), lupus, and Alzheimer's disease.

For examples of treatments of rheumatoid arthritis, there are therapeutic drugs that decrease pain and local inflammation including aspirin and non-steroidal anti-inflammatory drugs or NSAIDS (such as ibuprofen or naproxen) and other immunosuppressive drugs that decrease pain and inflammation while decreasing the growth of abnormal synovial tissue (the tissue that lines the inside of the joint). These drugs include methotrexate and low doses of corticosteroids (such as prednisone or cortisone). Other medications used to treat rheumatoid arthritis include: anti-malarial medications (such as hydroxychloroquine), gold, sulfasalazine, penicillamine, cyclophosphamide, cyclosporine, minocycline, interleukin receptor antagonist and anti-IL2 antibodies.

In particular embodiments, the formulations and compositions as disclosed herein are particularly useful for administration in conjunction therapies used for treatment of diseases associated with vascular permeability, such as vascular complications of diabetes such as non-proliferative diabetic retinopathy and nephropathy, nephrotic syndrome, pulmonary hypertension, burn edema, tumor edema, brain tumor edema, IL-2 therapy-associated edema, and other edema-associated diseases, as disclosed in International Application No: WO2003/086178 and U.S. Patent Applications US2005/0203013 and US2005/0112063 which are incorporated herein in theri entirety by reference. In a particular embodiment, the formulations and compositions as disclosed herein are particularly useful for administration in conjunction with IL-2 therapy, where the limiting factor of IL-2 therapy is IL-2 therapy-associated edema as disclosed in International Application No: WO2003/086178 and U.S. Patent Applications US2005/0203013 and US2005/0112063.

Treatment for Alzhemier's disease include, but are not be limited to, nonsteroidal anti-inflammatory drugs (NSAIDs), estrogen, steroids such as prednisone, vitamin E, menantine, donepezil, rivastigmine, tacrine, and galantamine. Holistic medicine include example such as gingko nuts extracts.

Treatment of endometrosis include, but should not be construed as limited to, a combination oral contraceptives (estrogen plus a progestin), progestins (such as medroxyprogesterone, danazol (a synthetic hormone related to testosterone, gonadotropin-releasing hormone agonists (GnRH agonists such as buserelin, goserelin, leuprolide and nafarelin), and nonsteroidal anti-inflammatory drugs (NSAIDs) for pain control.

Examples of treatment options for obesity include dieting and nutritional counseling, exercise regime, gastric-bypass surgery, and drugs such as a combination of fenfluramine and phentermine (often called fen-phen), orlistat, sibutramine, phentermine, benzphetamine, diethylpropion, mazindol, and phendimetrazine.

In alternative embodiments, the formulations and compositions can comprise a plurality of micelles, wherein some micelles comprise MetAP-2 inhibitor, and other micelles comprise other therapeutic agents, for example chemotherapeutic agents and antineoplastic agents.

The amount of the pharmaceutical composition as disclosed herein when administered to a subject will, of course, be dependent on the subject being treated, the severity of the affliction, the manner of administration, the judgment of the prescribing physician, etc.

The formulations and pharmaceutical composition can, if desired, be presented in a suitable container (e.g., a pack or dispenser device), such as an FDA approved kit, which can contain one or more unit dosage forms containing the carrier portion containing the targeting and immune response triggering portions.

Proliferative Assays

In general, one of skill in the art will know whether a given agent, for example a fumagillol derivative, is an anti-proliferative or anti-angiogenic agent. For the avoidance of doubt, one can use any of a number of in vitro or in vivo assays to evaluate the influence of a given agent on proliferation or angiogenesis. Whether or not a composition or formulation comprising a MetAP-2 inhibitor block copolymer conjugate in accordance with the present invention, can treat or prevent diseases associated with an angiogenesis-mediated condition can be determined by its effect in the mouse model as shown in the Examples below. However, at a minimum, a MetAP-2 inhibitor block copolymer as described herein will have anti-proliferative activity (i.e., at least 50% of the anti-proliferative activity of TNP-470) in a HUVEC assay as described in the Examples herein.

Another useful assay for determining if the compositions and formulations has disclosed herein have anti-proliferative or anti-angiogenesis activity is the CAM assay, which is frequently used to evaluate the effects of endothelial cell proliferation regulating factors because it is relatively easy and provides relatively rapid results. A proliferation-regulating factor useful in the methods and compositions described herein will modify the number of microvessels in the modified CAM assay described by Iruela-Arispe et al., 1999, Circulation 100: 1423-1431. The method is based on the vertical growth of new capillary vessels into a collagen gel pellet placed on the CAM. In the assay as described by Iruela-Arispe et al., the collagen gel is supplemented with a proliferative factor such as FGF-2 (50 ng/gel) or VEGF (250 ng/gel) in the presence or absence of test agents. The extent of the proliferative response is measured using FITC-dextran (50 μg/mL) (Sigma) injected into the circulation of the CAM. The degree of fluorescence intensity parallels variations in capillary density; the linearity of this correlation can be observed with a range of capillaries between 5 and 540. Morphometric analyses are performed, for example, by acquisition of images with a CCD camera. Images are then analyzed by imported into an analysis package, e.g., NHImage 1.59, and measurements of fluorescence intensity are obtained as positive pixels. Each data point is compared with its own positive and negative controls present in the same CAM and interpreted as a percentage of inhibition, considering the positive control to be 100% (VEGF or FGF-2 alone) and the negative control (vehicle alone) 0%. Statistical evaluation of the data is performed to check whether groups differ significantly from random, e.g., by analysis of contingency with Yates' correction.

Additional proliferative assays, including additional assays specifically designed to monitor angiogenic proliferation are known in the art and can be used to evaluate MetAP-2 inhibitors for use in the methods and compositions described herein. These include, for example, the corneal micropocket assay, hamster cheek pouch assay, the Matrigel assay and modifications thereof, and co-culture assays. Donovan et al. describe a comparison of three different in vitro assays developed to evaluate angiogenesis regulators in a human background (Donovan et al., 2001, Angiogenesis 4: 113-121, incorporated herein by reference). Briefly, the assays examined include: 1) a basic Matrigel assay in which low passage human endothelial cells (Human umbilical vein endothelial cells, HUVEC) are plated in wells coated with Matrigel (Becton Dickinson, Cedex, France) with or without angiogenesis regulator(s); 2) a similar Matrigel assay using "growth factor reduced" or GFR Matrigel; and 3) a co-culture assay in which primary human fibroblasts and HUVEC are co-cultured with or without additional angiogenesis regulator(s), the fibroblasts produce extracellular matrix and other factors that support HUVEC differentiation and tubule formation. In the Donovan et al. paper the co-culture assay provided microvessel networks that most closely resembled microvessel networks in vivo. However, the basic Matrigel assay and the GFR Matrigel assay can also be used by one of skill in the art to evaluate whether a given fumagillol derivative is an angiogenesis-inhibiting agent as necessary for the methods and compositions described herein. Finally, an in vitro angiogenesis assay kit is marketed by Chemicon (Millipore). The Fibrin Gel In Vitro Angiogenesis Assay Kit is Chemicon Catalog No. ECM630.

Other proliferative assays are disclosed in International Application No: WO2003/086178 and U.S. Patent Applications US2005/0203013 and US2005/0112063, and involve assaying endothelial cells on a permeable substrate (e.g., a collagen coated inserts of "Transwells"), contacting the assay with a test compound (e.g., a fumagillol derivative block copolymer conjugate), treating the assay with a marker (e.g., FITC label) and a permeability-inducing agent (e.g., vascular endothelial growth factor (VEGF) and platelet-activating factor (PAP) among others), and measuring the rate of diffusion of the marker compare to control. Compounds that are found to affect vascular permeability can be further tested for anti-proliferative activity using existing methods. The bioeffectiveness of MetAP-2 inhibitor block copolymer conjugate as an anti-proliferative or angiogenic agent in a patient being treated with such a block copolymer conjugate can be assessed by methods commonly known by person skilled in the art, for example, as disclosed in International Application No: WO2003/086178 and U.S. Patent Applications US2005/0203013 and US2005/0112063. One approach involves administering to the patient an intradermal injection of histamine before treating the subject with the a MetAP-2 block copolymer conjugate and measuring a histamine-induced local edema. Then, treating the subject with the a MetAP-2 inhibitor block copolymer conjugate, and again administering to the subject an intradermal injection of histamine subsequent to treating the subject with the MetAP-2 inhibitor block copolymer conjugate and measuring the histamine-induced local edema. A decrease in the measurement of the histamine-induced local edema compared to that seen before the treatment with the MetAP-2 inhibitor block copolymer conjugate indicates that the compound is bioeffective.

Compositions or formulations as disclosed herein capable of preventing or treating non-proliferative diabetic retinopathy can be tested by in vitro studies of endothelial cell proliferation and in other models of diabetic retinopathy, such as Streptozotocin. In addition, color Doppler imaging can be used to evaluate the action of a drug in ocular pathology (Valli et al., Ophthalmologica 209(13): 115-121 (1995)). Color Doppler imaging is a recent advance in ulkasonography, allowing simultaneous two-dimension imaging of structures and the evaluation of blood flow. Accordingly, retinopathy can be analyzed using such technology. The manner in which the compositions and formulations as disclosed herein are administered is dependent, in part, upon whether the treatment of a disease associated with vascular hyperpermeability, including non-proliferative retinopathy is prophylactic or therapeutic. For example, the manner in which compositions and formulations as disclosed herein are administered for treatment of retinopathy is dependent, in part, upon the cause of the retinopathy. Specifically, given that diabetes is the leading cause of retinopathy, the compositions and formulations as disclosed herein can be administered preventatively as soon as the pre-diabetic retinopathy state is detected.

Compositions or formulations as disclosed herein can be tested for activity against autoimmune disease or inflammation in standard models of MS or EAU (for uveitis) described herein in the example that follows.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%. The present invention is further explained in detail by the following examples, but the scope of the invention should not limit thereto.

EXAMPLES

The examples presented herein relate to methods, compositions and formulations of MetAP-2 inhibitors for oral or alternative administration, including topical administration. Throughout this specification, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

METHODS

Abbreviations mPEG-PLA=methoxy-poly(ethylene glycol)-poly(lactic acid), Suc=succinated; EDC=ethyl(diethylaminopropyl) carbodiimide; NHS=N-hydroxysuccinimide; en=ethylenamine; DDW=Double distilled water; DMF=Dimethylformamide; DMSO=Dimethyl sulfoxide.
Animals All animal procedures were performed in compliance with Boston Children's Hospital guidelines, and protocols were approved by the Institutional Animal Care and Use Committee.

Log D Measurement for TNP-470

Aqueous solubility is one of the important chemical properties affecting oral absorption of a drug. In order to predict the intestinal absorption of TNP-470, we measured its Log-D value which is a parameter of hydrophobicity determined by the ratio of drug concentration in octanol to that in water at 25° C. (Analiza, Cleveland Ohio). High Log-D values (>2) indicate low water solubility and hence a poor oral availability of a drug. For this study Log-D values of TNP-470 (30 mM) were measured at plasma and stomach pHs: pH=7.4 and pH=2 respectively.

Preparation of PEG-PLA-MetAP-2 Polymersomes (Polymeric-Micelles).

Figure 6A:
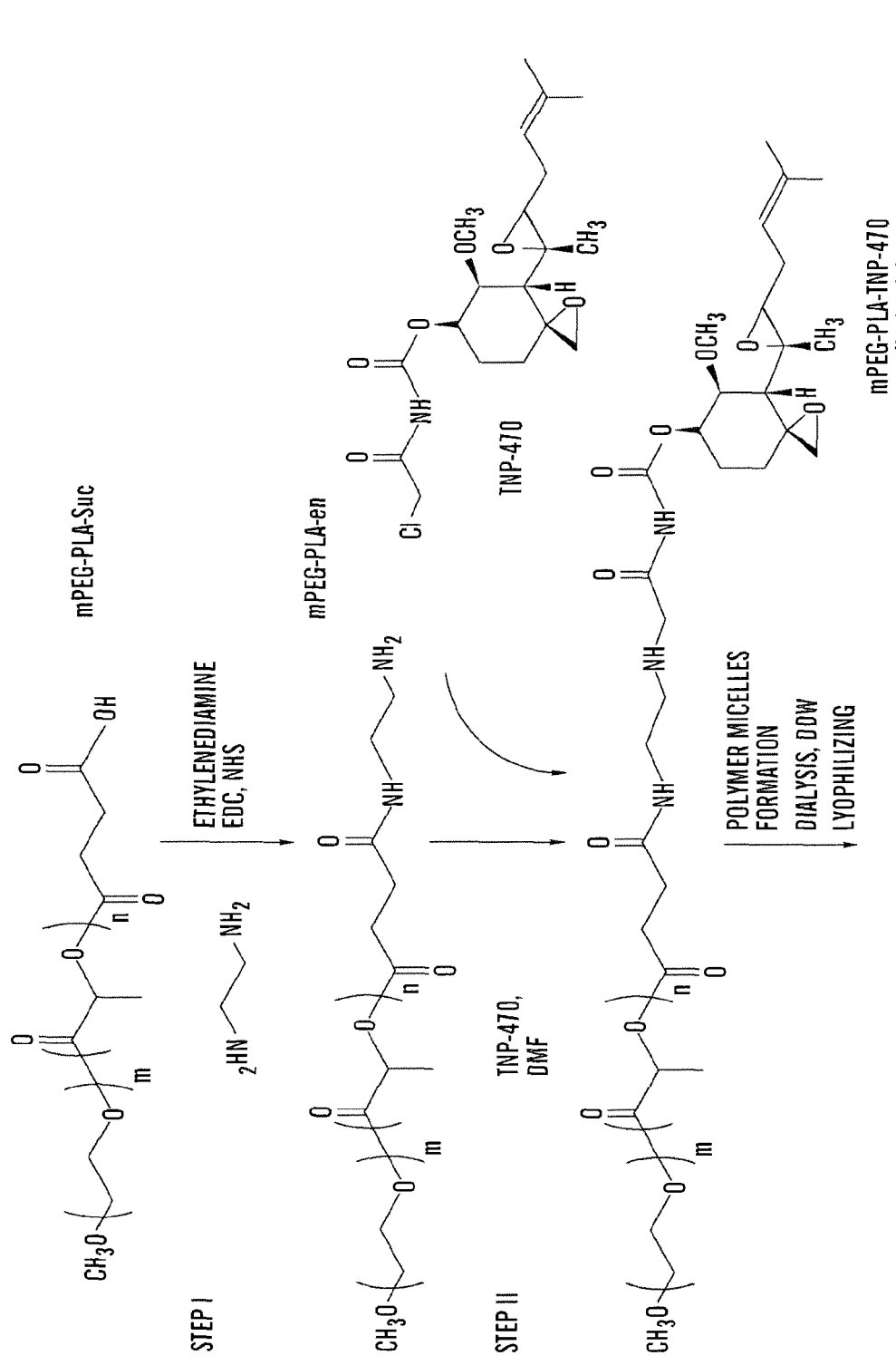
FIG. 6A shows a diagram of a conjugation reaction between TNP-470 and modified mPEG-PLA.

A known MetAP-2 inhibitor, TNP-470 (Takeda) was chosen for its activity, hydrophobicity and poor pharmacokinetic profile (see Placidi, Cancer Res. 55, 3036-3042 (1995)) and was bound to a diblock co-polymer using a two-step conjugation (FIG. 6A). In the first step succinated monomethoxy-poly(ethylene glycol)-poly (lactic acid) (mPEG2000-PLA1000) with free carboxic acid end-groups (Advanced Polymers Materials Inc.), was reacted with ethylenediamine (Sigma-Aldrich). Succinated mPEG-b-PLA-OOCCH2CH2COOH (500 mg) was dissolved in DMSO and reacted with ethyl(diethylaminopropyl) carbodiimide (EDC) and N-hydroxysuccinimide (NHS) in a molar ratio of 1:10:20 (Polymer:EDC:NHS respectively). In an alternative approach, the same amount of succinated mPEG-b-PLA-OOCCH2CH2COOH is dissolved in 10 ml MES buffer at pH 6 and the catalyst is N-hydroxysuccinimide (sulfo-NHS)). A five fold molar excess of ethylendiamine was added and reacted for 4 h at 25° C. The polymer solution was then dialyzed (MWCO 1000, Spectra/Por Biotech Regenerated Cellulose VWR) against DMSO leading to a 65% reaction efficiency. In the second step, the amine containing polymer was mixed with TNP-470 (350 gr), dissolved in DMSO and the solution was stirred for 4 h at 25° C. The polymeric micelles were formed by dialyzing the DMSO solution of the conjugate against double distilled water using a regenerated cellulose dialysis bag (MWCO 1000, Spectra/Por Biotech Regenerated Cellulose, VWR) to obtain micelles with high incorporation efficiency (>90%) and 0.8-1% free drug (w/w). The micelles were then lyophilized and stored at −20° C. in a dry environment until use.

Rhodamine labeled polymeric-micelles were formed using a similar protocol. The mPEG-PLA was conjugated via the N-terminal amine group with Lissamine rhodamine B sulfonyl chloride (Molecular Probes, Eugene, Oreg.) in DMSO. For green fluorescent polymer micelles, a commonly used hydrophobic marker 6-coumarin (Sigma-Aldrich, Mo., USA) at 0.1% w/w was added to the polymeric solution before the final dialysis step.

Characterization of Conjugation by NMR Analysis

Nuclear Magnetic Resonance (NMR) spectrometer analysis (NERCE/BEID, Harvard Medical School) was conducted for each reaction step and Mass spectrometry (Proteomic core, Harvard Medical School) was performed on the conjugate. In order to evaluate the efficiency of ethylendiamine binding to mPEG-PLA (first reaction step, FIG. 6A) and TNP-470 binding to the polymer via the amine (second step, FIG. 6A), we used the colorimetric amine detection reagent: 2,4,6-Trinitrobenozene Sulfonic Acid (TNBSA) (Pierce, Rockford Ill.) was used. TNBSA reacts with primary amines to produce a yellow product whose intensity was measured at 450 nm. To calculate amine concentration in the polymer a linear calibration curve of amino acid was used. To measure TNP-470 loading into polymeric-micelles, we incubated 10 mg/ml Lodamin in 500 μl NaOH (0.1 N) to accelerate PLA degradation. After an overnight incubation with shaking (100 r.p.m) at 37° C., we added Acetonitrile to the samples (1:1 NaOH:Acetonitrile) and analyzed for TNP-470 concentration. TNP-470 concentration was measured using a high-performance liquid chromatography system (HPLC, System Gold® Microbore, Beckman Coulter). A 20-μl portion of each sample was injected into a Nova-pak C18 column (3.9-×150-mm i.d.; Waters), and analyzed using a calibration curve of TNP-470. TNP-470 binding to amine was also measured using TNBSA reagent and was confirmed by subtracting the non-bound drug from the total drug added to the reaction.

Amine Determination

The first step of ethylenediamine binding to the polymer, and the second step of TNP470 conjugation reaction through the free amine, were further verified using (2,4,6-Trinitrobenozene Sulfonic Acid (TNBSA) reagent (Pierce, Rockford Ill.). TNBSA is a sensitive assay reagent which can couple to free amino groups and form a highly chromogenic derivate. The reaction was carried out after the addition of 0.01% (w/v) TNBSA in 0.1M Sodium bicarbonate buffer. A series of PEG-PLA polymer concentrations before and after TNP-470 conjugation were allowed to react for 2 hr in 37° C. with TNBSA and the yellow color was measured using a plate reader.

The correlation between the molar amine concentration and color absorption at 450 nm was determined according to a standard curve done for aspartic acid.

Cell Culture.

Murine Lewis lung carcinoma (LLC) and B16/F10 melanoma cells were obtained from American Type Culture Collection (ATCC, Manassas, Va., USA). Human Umbilical Vascular Endothelial cells (HUVEC) were purchased from Cambrex (USA). The cells were grown and maintained in medium as recommended by the manufacturers. Dulbecco's Modified Eagle's Medium with 10% fetal bovine serum was used for tumor cells and EMB-2 (Cambrex Bio Science Walkersville, Inc.) containing 2% fetal bovine serum and EGM-2 supplements was used for HUVEC.

HUVEC Proliferation Assay

HUVEC were exposed to different concentrations of Lodamin equivalent to 50-1,000 nM free TNP-470 (0.12-2.4 mg/ml micelles) and incubated in a low serum medium for 48 h at 37° C. To rule out a possible cytotoxic effect of the carrier, empty micelles were added to HUVECs as a control (4.8 mg/ml). A WST-1 proliferation assay (Roche Diagnostics) was used. Cell viability was calculated as the percentage of formazan absorbance at 450 nm of treated versus untreated cells. Data were derived from quadruplicate samples in two separate experiments. The effect of Lodamin (60 nM TNP-470 equivalent q.o.d. on HUVEC growth rate was evaluated by daily counting of HUVEC cells up to 5 d and compared to the number of untreated cells or cells treated with Vehicle (same concentration as Lodamin).

Uptake of Polymeric Micelles by HUVEC and their Localization in Cells.

To evaluate the uptake of polymeric micelles by HUVEC, 6-coumarin labeled PEG-PLA micelles or rhodamine conjugated to mPEG-PLA were used. HUVEC were seeded in a 24-well plate ($2\times10^4$ per well) in EGM-2 medium (Cambrex) and were allowed to attach overnight. Fluorescent-labeled micelles (10 mg/ml) were suspended over a bath sonicator for 5 min, and 20 μl of the suspension was added to the cultured cells. After the designated time points (20 min, 2, 4, 7 and 24 h), the cells were washed three-times with PBS and analyzed by flow cytometry, or alternatively fixed with 4% parformaldehyde. For confocal microscopy, cells were mounted using DAPI containing Vectashild (Vector, Laboratories, Burlingame, Calif.). Optical sections were scanned using Leica TCS SP2 AOBS a ×40 objective equipped with 488-nm argon, 543-nm HeNe, and 405-nm diode lasers. To study Lodamin internalization into endothelial cells, confocal microscopy was used to co-localize 6-coumarin labeled polymeric-micelles with endo-lysozome. Live HUVEC cells were imaged in different time points after addition of labeled micelles to cell media (15 μg/ml) up to 1 h. At this point, LysoTracker Red® (Molecular Probes, Eugene, Oreg.) was added to the medium for the detection of acidic intracellular vesicles: Endosomes and Lysosomes. After 20 min of incubation, cells were imaged by confocal using optical sections with 488-nm argon, 543-nm HeNe, and 405-nm diode lasers.

To further verify that polymeric micelle internalization occurs through endocytosis, cell uptake was measured in cold conditions (4° C.) in comparison to cell uptake at 37° C. HUVEC were plated at a concentration of 15,000 cells/ml in two 24-well plates for 24 h. Fluorescent labeled polymeric micelles (15 μg/ml) were added and incubated at different time points: 20, 30, 40 and 60 min (n=3) in cold room (4° C.) and in 37° C. After the designated time points the cells were washed 3 times with PBS and lysed with 100 μl lysis buffer (BD Biosciences). Cell extracts were measured for fluorescent signal in a Wallac 1420 VICTOR plate-reader (Perkin-Elmer Life Sciences) with excitation/emission at 488 nm/530 nm.

Morphology of MetAP-2 Inhibitor Polymeric Micelles by Transmission Electron Microscopy (TEM).

In order to study the morphology of MetAP-2 inhibitor polymersomes, Transmission Electron Microscopy (TEM) images were taken at the day of preparation and one week post preparation. Polymer micelles dispersed in double distilled water were imaged with cryo-TEM (JEOL 2100 TEM, Harvard University—CNS).

In-Vitro TNP-470 Release from MetAP-2 Inhibitor-Polymersomes.

To study the kinetic release of TNP-470, Lodamin (20 mg) was incubated with either 1 ml PBS pH=7.4 or simulated gastric fluid (HCL:ddw pH=1.2). Every few days, supernatant was taken and analyzed for TNP-470 concentration and a cumulative release graph of TNP-470 was determined. TNP-470 concentration was measured using HPLC. TNP-470 was detected as a peak at 6 min with 50% acetonitrile in water at the mobile phase. The flow rate was 1 ml/min, and the detection was monitored at 210 nm wavelength.

Size of MetAP-2 Inhibitor Polymeric Micelles

The average size and size distribution of polymeric micelles were determined by Dynamic Light Scatterer (DLS, DynaPro, Wyatt Technology). The measurements were done at 25° C. using Dynamic V6 software. Lodamin (TNP-470 polymersomes) at 1.5 or 2 mg/ml dispersed in double-distilled water were measured by 20 successive readings with DLS. Micelles' size was also measured after 24 hr to evaluate their structural stability.

Evaluation of Antitumor Activity of MetAP-2 Inhibitor Polymersomes In-Vivo

Animal procedures were performed in the animal facility at Children's Hospital. Eight-week-old male C57BL/6 mice (Jackson Laboratories, Bar Harbor, Mass.) were injected subcutaneously with $1\times10^6$ Lewis Lung Carcinoma cells (LLC) at the back. When tumors reached a volume of 100 $mm^3$ the mice were divided into 5 groups, and treated every day for 12 days with TNP-470 polymeric micelles, administrated orally using a gavage needle. Different doses of polymersomes were given daily: 15 mg/kg (5 mice), 30 mg/kg (3 mice) and 60 mg/kg (1 mice) TNP-470 equivalent, respectively (5, 10, 20 mg polymeric drug per mouse, respectively). The control groups were five mice that were given the same dose of polymersomes without the drug, and five mice that were given drinking water.

Every two days the weight of the mice was monitored and tumors dimensions were measured using a caliper. Tumor volume was calculated according to an ellipsoid formula.

Absorption Kinetics of Polymeric Micelles in the Gastrointestinal Tract

A non-invasive IVIS 200 in-vivo imaging system (Xenogen system 3.0) was used in order to track the polymeric micelles labeled with fluorescent marker in a manner similar to the cell uptake study. Fluorescent polymersomes were given orally to three nude mice, the mice were anesthetized using an Isofluran chamber, and images were taken after different time periods. All the images were taken under identical conditions.

Corneal Micropocket Assay

In order to evaluate the antiangiogenic properties of Lodamin, the corneal micropocket angiogenesis assay was performed as previously detailed[29]. Pellets containing 80 ng carrier-free recombinant human bFGF or 160 ng VEGF (R&D Systems, Minneapolis, Minn.) were implanted into micropockets created in the cornea of anesthetized mice. Mice were treated daily with 15 mg/kg TNP-470 equivalent of Lodamin for 6 d, and then the vascular growth area was measured using a slit lamp. The area of neovascularization was calculated as vessel area by the product of vessel length measured from the limbus and clock hours around the cornea, using the following equation: Vessel area (mm2)= [$\pi$×clock hours×vessel length (mm)×0.2 mm].

Body Distribution, Intestinal Absorption and Toxicity of Lodamin

For all biodistribution studies we used a fluorescent marker for tracking Lodamin. Mice were administered 6-coumarin labeled mPEG-PLA by oral gavage for 3 d (100 µl of 1.5 mg/ml). On the third day of treatment, after 8 h of fasting, animals were sacrificed and spleen, kidney, brain, lungs, liver, intestine, stomach, and bladder were collected. The fluorescent 6-coumarin was extracted from the tissues by incubation with formamide for 48 h at 25° C. Samples were centrifuged and signal intensity of fluorescence of supernatants was detected with a Wallac 1420 VICTOR plate-reader (Perkin-Elmer Life Sciences) with excitation/emission at 488 nm/530 nm. The results were normalized to protein levels in the corresponding tissues. Tissue autofluorescence was corrected by subtracting the fluorescent signal of non-treated mouse organs from the respective readings in treated mice. Similarly, levels of fluorescent signal in mouse sera were measured in different time points (1, 2, 4, 8, 24, 48 and 72 h) using excitation/emission readings at 488 nm/530 nm.

In order to analyze cell uptake in the different tissues in tumor bearing mice, PEG-PLA-rhodamine micelles (100 µl of 1.5 mg/ml) or water were orally administered to C57Bl/6J mice bearing LLC tumors (200 mm$^3$) for 3 d. Organs were removed, incubated for 50 min in collagenase (Liberase Blendzyme 3; Roche Diagnostics Corp., IN) in 37° C. to obtain a single cell suspension. These suspensions were analyzed by flow cytometry in order to quantify the uptake of micelles into different tissue cells when compared to those in the untreated mouse.

In order to evaluate intestinal absorption, mPEG-PLA-rhodamine micelles were orally administered to C57Bl/6J mice after 8 h of food fasting. After 2 h mice were sacrificed and 2.5 cm segments of the small intestine were removed, washed, and analyzed by histology and confocal microscopy. The rhodamine-labeled polymeric micelles were detected by confocal microscopy (Leica TCS SP2 AOBS) with a 488-nm argon laser line. Actin filaments were stained with phalloidin-FITC (Sigma) and nuclei were stained by DAPI (Sigma). To further study the uptake of Lodamin in the intestine, high resolution images were imaged with cryo-TEM. Intestines from treated (as above) and untreated mice were excised and immersed immediately in a freshly prepared 4% paraformaldehyde in PBS pH 7.4 for 2 h at 25° C. The samples were washed in PBS, transferred to a 30% sucrose solution overnight at 4° C. and embedded in OCT and kept at −80° C. until processing. Fifteen sections with 10 µm each were prepared and processed for Confocal microscopy or TEM. Four TEM samples were fixed for 30 min in freshly prepared 2% paraformaldehyde, 2.5% glutaraldehyde, 0.025% $CaCl_2$ in 0.1 M sodium cacodylate buffer, pH 7.4 and subsequently postfixed for 30 min in 1% osmium tetroxide in 0.1 M sym collidine buffer, pH 7.4 at 25° C., stained en bloc in 2% uranyl acetate, dehydrated, and embedded under inverted plastic capsules. Samples were snapped free of the glass coverslips by a cycle of rapid freezing and thawing. Thin sections were cut en face with diamond knives using a LEICA UCT Ultramicrotome. Specimens were examined using a JEOL 2100 TEM.

To exclude tissue toxicity, histological analysis (H&E) of liver, intestine, lung and kidneys was conducted (Beth-Israel pathology department, BIDMC). To further exclude liver toxicity we analyzed serum levels of liver enzymes: ALT, AST (Done at Shriners Burns Hospital, Boston, Mass.). These studies were performed on 20 d-long Lodamin treated mice (15 mg/kg TNP-470 equivalent q.d.) and compared to untreated mice (n=3-4).

Oral Administration of Lodamin In-Vivo and Primary Tumor Experiments

Animal procedures were performed in the animal facility at Children's Hospital Boston using 8 week old C57Bl/6J male mice (Jackson Laboratories, Bar Harbor, Me.).

For tumor experiments: LLC cells (1×10$^6$) or B16/F10 melanoma cells (1×10$^6$) were implanted subcutaneously in 8 week old C57Bl/6J male mice (Jackson Laboratories, Bar Harbor, Me.). Oral availability of free TNP-470 was compared to that of Lodamin. A dose of 30 mg/kg q.o.d. of free TNP-470 and an equivalent dose of Lodamin (Lodamin, 6 mg in 100 µl/d) were administered to LLC tumor bearing mice (~100 mm$^3$) and tumor growth was followed for 18 d. Free drug was given as a suspension in double distilled water and freshly prepared before each dose. Additionally, we compared different doses and frequencies of Lodamin treatment: 15 mg/kg q.d., 15 mg/kg q.o.d. and 30 mg/kg q.o.d. To eliminate any possible effect of the vehicle (polymer without drug) one group of mice was given micelles without drug and tumor progression was compared to water treated mice.

For the melanoma tumor experiment, a dose of 15 mg/kg q.d. Lodamin was administered to B16/F10 melanoma bearing mice. In all experiments, tumor size and animal weight were monitored every 2 d. Tumor volume was measured with calipers in two diameters as follows: (width)×(length)×0.52. Note that all the above Lodamin doses are presented as TNP-470 equivalent.

Oral Administration of Lodamin and Liver Metastasis Experiments

To examine the effect of oral Lodamin treatment on metastasis development and prevention, liver metastases were generated by spleen injection. C57Bl/6J mice (n=14) were anaesthetized with Isoflurane and prepared for surgery. A small abdominal incision was made in the left flank and the spleen was isolated. B16/F10 tumor cells in suspension (50 µl, 5×105 in DMEM medium without serum) were injected into the spleen with a 30-gauge needle, and the spleen was returned to the abdominal cavity. The wound was closed with stitches and metal clips. After 2 d mice were divided into two groups, one was treated daily with oral Lodamin (15 mg/kg) using gavage and the second group was administered water by gavage. After 20 d, we terminated the experiment. Mice were killed and autopsied, livers and spleens were removed by surgical dissection, imaged, and histology was carried out. Liver and spleen tissues were stained with Hematoxylin & Eosin to evaluate tissue morphology and detect metastasis. Immunohistochemistry was carried out to specifically detect B16/F10 cells in the liver using anti-mouse melanoma antibody (HMB45, abCAM) and using DAB staining.

Evaluation of Neurotoxicity with Balance Beam Motor Coordination Test

A slightly modified balance beam motor coordination test was performed on three groups of mice: Oral Lodamin treated mice (30 mg/kg eq. q.o.d.), free TNP-470 (30 mg/kg) subcutaneously injected mice and water treated mice (administered by gavage). The mice were pretreated for 14 d (n=4-5 per group) and then the mice were allowed to acclimate to the procedure room for 1 h, after which they were trained in 3 trials to cross a wide (20 mm width×1 m length) balance beam. All the mice crossed the wide beam without making foot-slip errors. The mice were then trained on a narrow (4 mm width×1 m length) beam for 3 trials. At the end of the training trials, no freezing behavior was observed, and the mice would start to walk within 4 seconds of being placed on the beam. The mice were then videotaped as they performed in 3 test trials of 3 beam crossings each—a total of 9 crossings per mouse. The 3 trials were separated by at least 1 h to avoid fatigue of the mice. Videotaped crossings were scored for number of foot-slip errors and time to cross. All experiments and scoring of the different groups were performed by an investigator who has been no knowledge regarding the treatment regime of the mice.

MetAP-2 Inhibitor Polymersome Effect on Angiogenesis, Proliferation and Apoptosis in Tumor Tissues Histologic evaluation of tissue was performed on 8 µm thick frozen sections of LLC tumors that were removed from two random Lodamin-treated or untreated mice 14 d post treatment (15 mg/kg q.d. TNP-470 equivalent). Tumors were sectioned and analyzed for cell markers, 20 microscope fields (×400) were imaged.

Tissues were stained with Hematoxylin & Eosin to detect tissue morphology. Immunohistochemistry was carried out using Vectastain Elite ABC kit (Vector Laboratories, Burlingame, Calif.). Primary antibodies included CD31 (BD Biosciences, San Jose, Calif.) for microvessel staining and anti-Ki-67 (DAKO, CA, USA) detection of proliferation. Detection was carried out using a 3,3'-diaminobenzidine chromogen, which results in a positive brown staining. Apoptotic cells were detected by reacting the tissues with Terminal deoxynucleotide transferase mediated dUTP-biotin nick end labeling (TUNEL) using a kit (Roche) following the company's protocol. Vessels were detected in the same tissues by anti-CD31 and secondary FITC anti-mouse antibody (Jackson ImmunoResearch) conjugated antibody (green) and nuclei were detected by DAPI (blue).

Statistical Analysis

In-vitro data are presented as mean±SD, whereas in-vivo data are presented as mean±SE. Differences between groups were assessed using unpaired two-tailed Student's t-test, and $P<0.05$ was considered as statistically significant.

Example 1

Block copolymer micelles (polymersomes) have been proposed for the delivery of hydrophobic drugs with low aqueous solubility (such as Paclitaxel). The amphiphilic nature of diblock copolymers such as poly (lactide)-poly (ethylene glycol) (PLA-PEG), enables the formation of micelles in aqueous media. In an aqueous environment, the diblock copolymer is self-assembled into a structure of hydrophobic core, formed by the association of the hydrophobic polymer and the drug, and a hydrophilic shell, formed by the hydrophilic polymer, commonly PEG.

Block copolymers as disclosed in U.S. Pat. No. 4,745,160 (which is incorporated herein by reference) have been used form water insoluble, amphiphilic, non-crosslinked linear, branched or graft block copolymers having polyethylene glycol as the hydrophilic component and poly(D-, L-, or D, L-lactic acids) as the hydrophobic components.

Block copolymers as disclosed in U.S. Pat. No. 5,543,158 (which is incorporated herein by reference) have been described to form nanoparticles or microparticles that are solid particles that are suspended in water that are formed from a water-insoluble block copolymer consisting essentially of poly(alkylene glycol) and poly(lactic acid). The molecular weight of the block copolymer is high and the copolymer is insoluble in water. In the nanoparticle or microparticle, the biodegradable moieties of the copolymer are in the core of the nanoparticle or microparticle and the poly(alkylene glycol) moieties are on the surface of the nanoparticle or microparticle in an amount effective enough to decrease uptake of the nanoparticle or microparticle by the reticuloendothelial system. Nanoparticles are prepared by dissolving the block copolymer and drug in an organic solvent, forming an oil and water emulsion by sonication or stirring, and collecting the nanoparticles containing the drug following precipitation. It does not provide for the solubilization of hydrophobic drugs.

The inventors demonstrate that MetAP-2 inhibitor TNP-470 was successfully conjugated to a modified PEG-PLA polymer through its amine, and formed nano-size polymersomes. A schematic diagram of the conjugation process is shown in FIG. 6A. Step I demonstrates the reaction between succinated mPEG-PLA and ethylendiamine that results in an amine terminated polymer. Step II demonstrates the reaction between the amine reactive polymer and the terminal chlorine of TNP-470. The conjugate is then dialyzed against water in an excess of TNP-470 to form polymeric micelles. The inventors demonstrate, using images taken by TEM, that spherical micelles were formed and size measurement with DLS showed a low range of size distribution around 10 nanometers. By using confocal microscopy images of fluorescent-labeled polymersomes, the inventors demonstrate rapid uptake by Human Umbilical Vein Endothelial Cells (HUVECs), and when TNP-470 polymersomes were added, a significant inhibition of HUVECs proliferation was shown (as compared to no effect of the carrier itself).

In-vivo studies done on mice showed a significant inhibition of subcutaneous Lewis Lung Carcinoma tumors with C57/BL mice given a daily oral administration of TNP470 micelles. A dose of 15 mg/kg TNP-470 equivalent showed 63% inhibition without any weight loss to the mice.

NMR results from the different reaction steps are shown in FIG. 1. The results show the binding of the ethylendiamine through the carboxic acid group at the original polymer, and the TNP-470 binding to the polymer through the amine.

Amine Determination.

Figure 2:
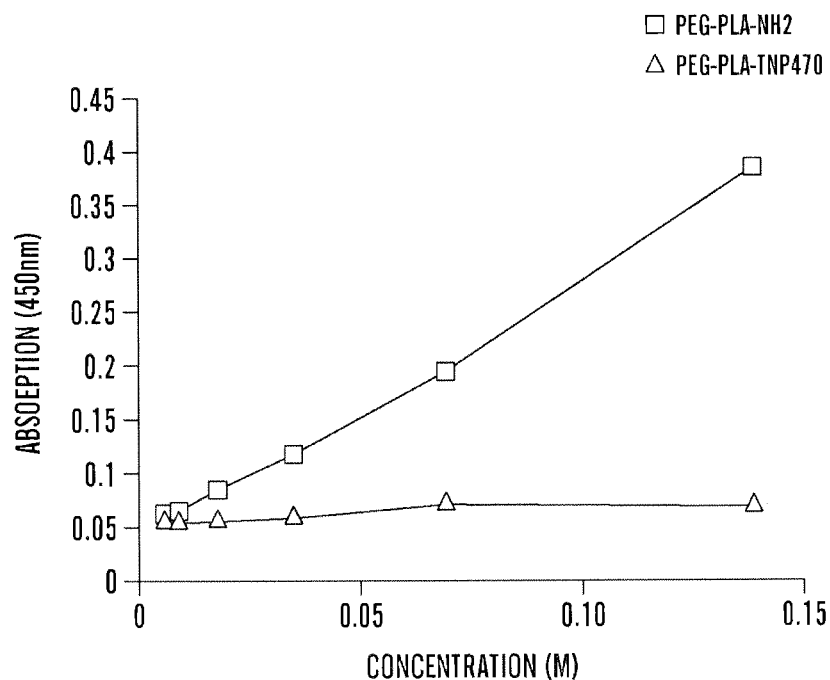
FIG. 2 shows amine levels of mPEG-PLA-en polymer before and after TNP-470 binding. TNBSA reaction was performed as described in the Examples; levels of 450 nm absorption indicate the levels of free amines.

To further verify the binding of TNP-470 to the modified PEG-PLA through the amine in the polymer and the terminal chlorine in the drug, a TNBSA reagent reaction for the detection of free amino groups was performed. According to the results (FIG. 2) the polymer was saturated with ethylendiamine. Correlation between molar amine groups in the modified polymer and absorption in 450 nm were determined by a theoretical value from a standard curve done for aspartic acid (not shown). Moreover, after TNP-470 conjugation, no free amines were detected, indicating that the polymer was saturated with TNP-470 conjugated through the amine group at the polymer.

Morphology of MetAP-2 Inhibitor Polymeric Micelles by Transmission Electron Microscopy (TEM).

In order to study the morphology of TNP-470-micelles, Transmission Electron Microscopy (TEM) images were taken at the day of preparation (data not shown).

Polymersomes dispersed in double distilled water were imaged with cryo-TEM (JEOL 2100 TEM, Harvard university-CNS). The images show that the self-assembled polymersomes had a uniform spherical morphology.

HUVEC Proliferation.

Figure 4A:
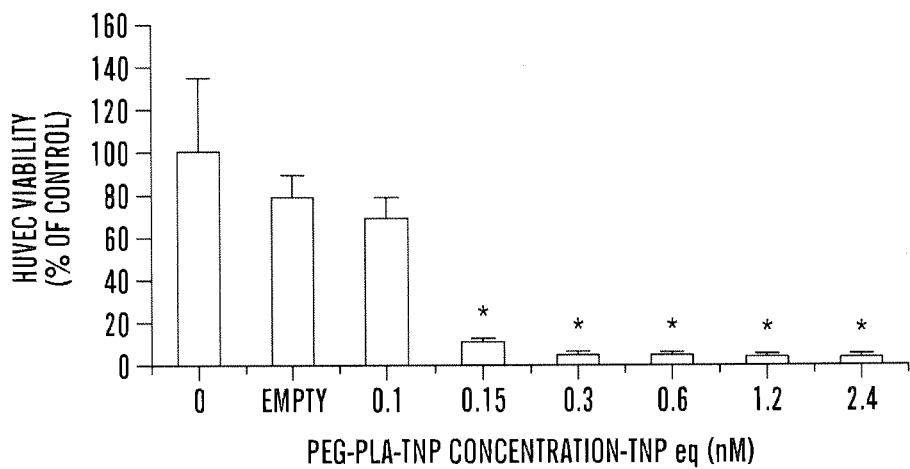
FIG. 4A shows inhibition of human umbilical vein epithelial cell (HUVEC) proliferation by MetAP-2 inhibitor polymersomes. Different concentrations of TNP-470 micelles (comprising between 62.5-1000 nM of TNP-470 equivalent) showed a cytostatic effect on HUVECs as measured by WST-1 ($*p<0.0005$).
Figure 4B:
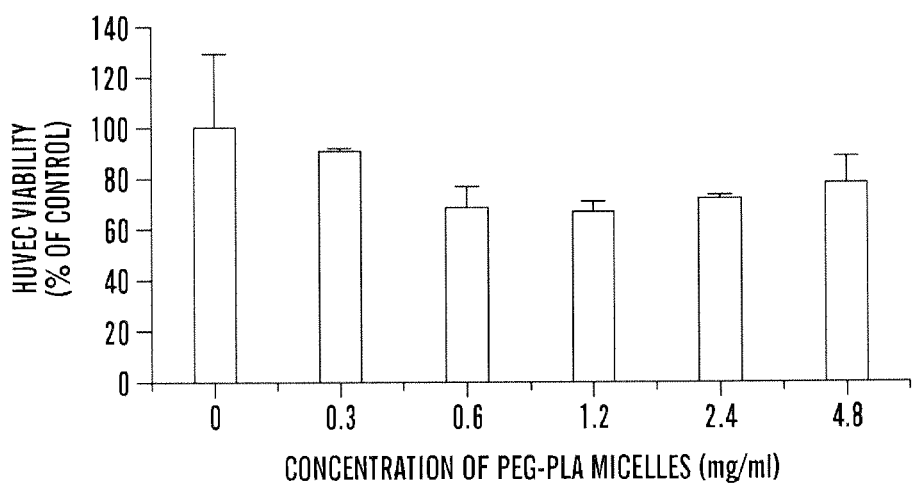
FIG. 4B shows that HUVEC proliferation was not affected by polymeric micelles without MetAP-2 inhibitor. No significant differences in proliferation were detected, even with a double concentration of carrier than that of the MetAP-2 inhibitor polymersomes.

The effect of different concentrations of TNP-470 polymersomes on the proliferation of HUVECs was evaluated using a WST-1 reagent. FIG. 4 shows the inhibition in proliferation after 48 hr of incubation. FIG. 4A shows the effect of TNP-470 micelles, and FIG. 4B shows the effect of micelles without drug on HUVECs. A significant inhibition of HUVEC proliferation was detected from 0.3 mg/ml and up to 2.4 mg/ml micelles, which are 62.5 nM-1000 nM TNP-470 equivalent (88% and 95% inhibition respectively). The same concentrations of polymeric micelles without TNP-470, as well as double concentration (4.8 mg/ml) showed no significant effect on HIJVEC proliferation.

Example 2

Cellular Uptake Studies.

In order to evaluate the kinetics of polymersomes uptake by HUVECs in in-vitro condition, HUVECs were incubated with fluorescent polymersomes, washed and imaged by confocal microscopy. HUVECs were incubated with the micelles for 20 min, 4 hr and 24 hr. After 20 min. micelles were already uptaken by the cells and located at the cytoplasm (data not shown). After 2 hr, 4 hr, 7 hr and 24 hr the uptake increased and the micelles were detected as concentrated spots inside cell cytoplasm (data not shown).

In Vivo Effects of PEG-PLA-MetAP-2 Inhibitor Micelles.

Figure 5B:
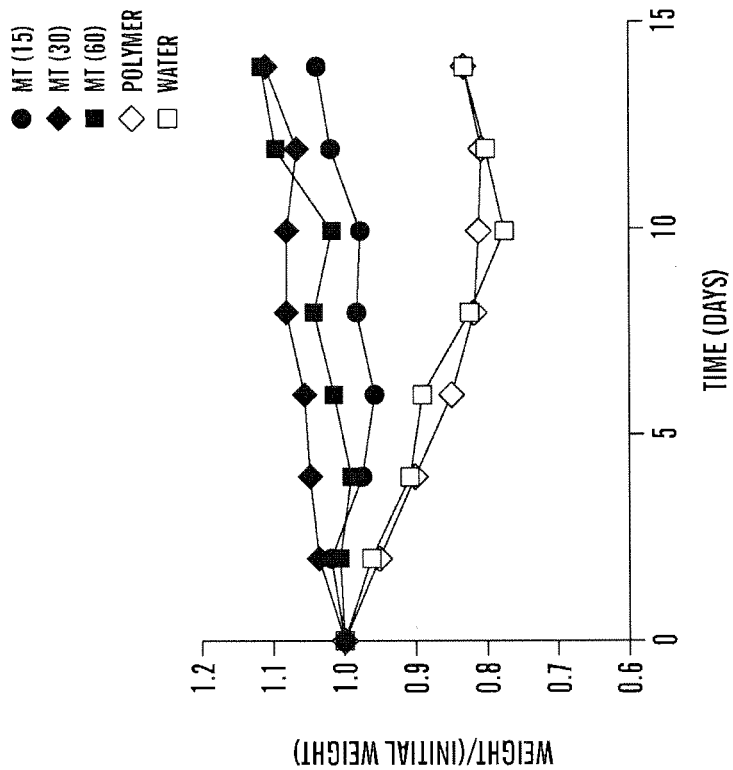
FIG. 5B shows the effect of TNP-470 polymersomes on mice weights. Mice were weighed q.o.d, the results are an average weight of mice in each group.
Figure 5A:
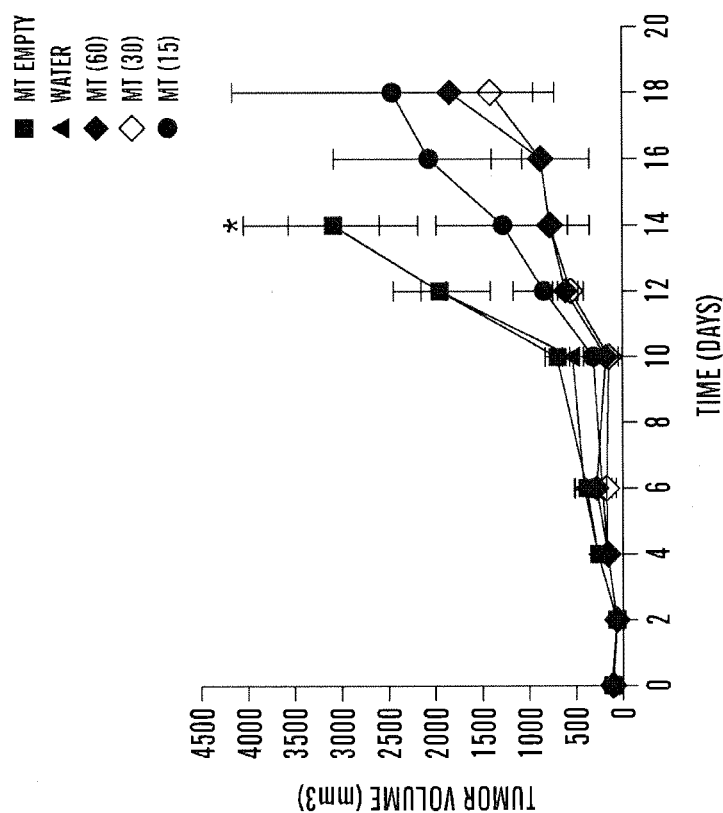
FIG. 5A shows the effect of MetAP-2 inhibitor polymersomes on tumor volume. Tumor volume, measured during 14-18 days of daily oral administration of TNP-470 polymeric micelles to C57/BL mice ($*p<0.05$).

C57/BL mice bearing s.c LLC tumors showed inhibition in tumor growth when treated with PEG-PLA-TNP-470 micelles given orally. All doses showed a significant effect already after 14 days of daily treatment, as shown in FIG. 5A. The controlled groups had to be scarified on day 14, and the treatment continued up to day 18. The lowest dose (15 mg/kg TNP-470 equivalent) showed a significant inhibition of tumor growth (63%) after 14 days (*p<0.05), without any weight loss to the mice. whereas higher doses of 30 mg/kg and 60 mg/kg TNP-470 equivalent showed 74%, 75% inhibition respectively, but also caused almost 20% weight loss (FIG. 5B).

Absorption of Polymeric Micelles in the Gastrointestinal Tract.

The non-invasive Xenogen system was used to track the absorption kinetics of the polymersomes after oral administration. The micelles were concentrated at the gastrointestinal tract within 10 min post administration (GI track) (data not shown). Apparently the absorption was rapid and after 1 hr fluorescent signal was found near the bladder and the prostate glands. After 24 hr the signal was still detectable.

Example 3

Chemical and Physical Characterization of MetAP-2 Inhibitor Polymersomes

In an effort to predict the oral availability of TNP-470, the hydrophobicity of Lodamin was measured using log-D parameter. The measured Log-D values were 2.39 at pH=2 and 2.57 at pH=7.4. The high Log-D values (>2) indicate a very low solubility in water. This property indicates that the designed Lodamin had with improved solubility and oral availability.

Figure 3:
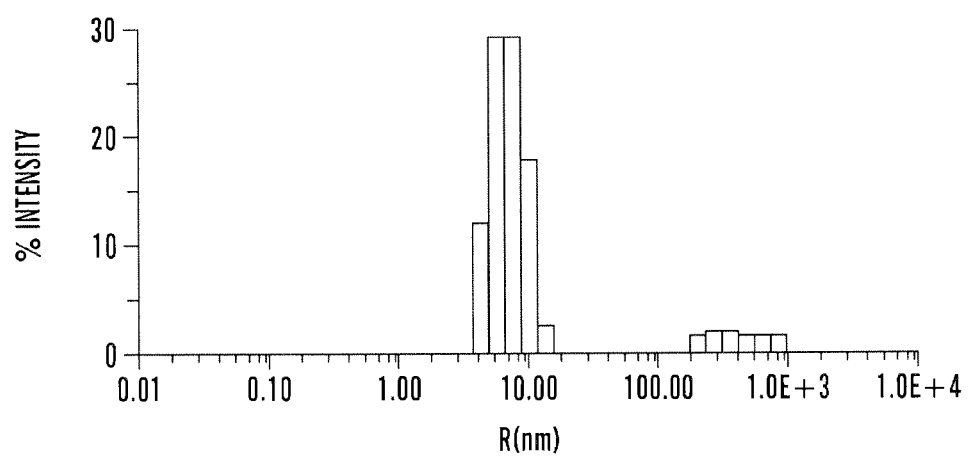
FIG. 3 shows TNP-470 polymersomes' size ranges. A typical DLS graph showing diameter distribution of TNP-470 polymersomes.

The formulation of Lodamin and the conjugation of TNP-470 are described in detail in the Methods. The chemical and physical properties of Lodamin were characterized. First, the binding of TNP-470 to mPEG-PLA was confirmed by $^3$H NMR (data not shown) and mass spectrometry showing an average m/z of 3687 for mPEG-PLA-TNP-470. FIG. 6A demonstrates the reaction of Lodamin preparation. Using amine detection reagent, the incorporation efficiency of ethylenediamine to mPEG-PLA was determined as 65%, and in the second step TNP-470 was shown to be bound in high efficiency of >90%. Lodamin contained 0.8-1% (w/w) free TNP-470 as determined HPLC. The average size and size distribution of Lodamin was determined by a DLS (FIG. 3) on the day of preparation and after 10 d of incubation in aqueous medium to evaluate Lodamin stability (n=4). The majority of micelles (90%) at day of preparation were 7.8-8 nm in diameter, with a small population of larger particles (200-400 nm). The size remained almost unchanged after 10 days.

The morphology of Lodamin was characterized by TEM. (FIG. 6B). The images showed that the polymeric micelles had acquired a uniform spherical structure, which remained stable after two weeks of incubation in water at 37° C. Since the drug is located in the PLA core of the micelle structure and PLA is spontaneously hydrolyzed in an aqueous environment, we studied the release kinetics of TNP-470 from Lodamin. A slow-release kinetic of TNP-470 was obtained following incubation in PBS (pH=7.4) or in gastric liquid (pH=1.2). The TNP-470 was released over a period of 28 d with an early peak burst of ~30% after the first day of incubation (FIG. 6C).

Endothelial Cells Take Up MetAP-2 Inhibitor Polymersomes by Endocytosis

Figure 7A:
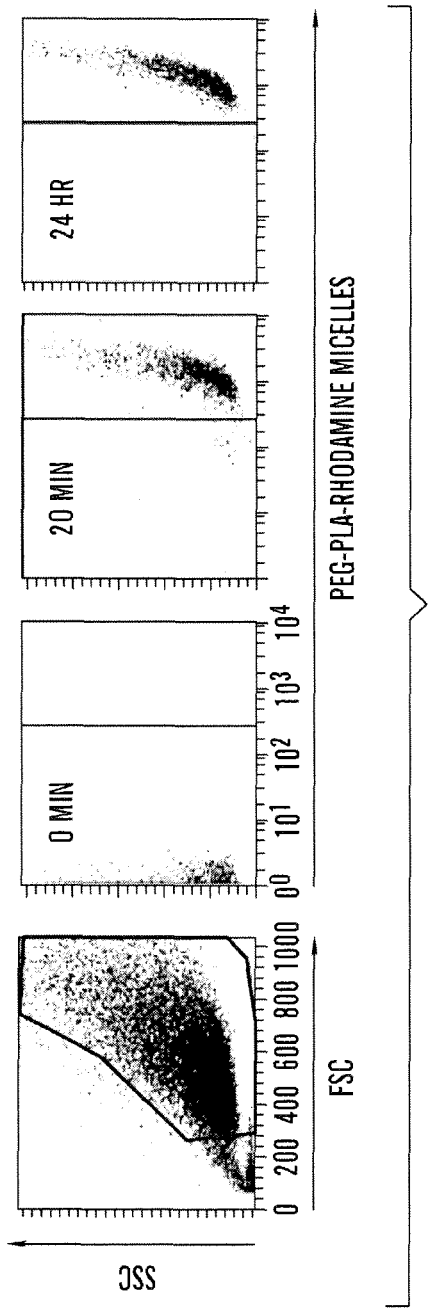
FIG. 7A shows flow cytometry analysis of uptake of Rhodamine labeled mPEG-PLA micelles by HUVEC (FL2high) at 0 min, 20 min and 24 h of incubation with micelle. Incubation after 2, 4 and 7 h showed a similar pattern as after 24 h of incubation (not shown).

The uptake of polymeric micelles by HUVEC and its kinetics was evaluated initially. HUVEC were incubated with 6-coumarin labeled mPEG-PLA micelles for 20 min, 2, 4 and 7 h and were imaged by confocal microscopy. Confocal images show HUVEC uptake of polymeric micelles labeled with 6-coumarin after 20 min and 7 h incubation time periods (data not shown). In Live HUVEC cells as were imaged 1 h post the addition of labeled micelles to cell media (15 μg/ml, in green). LysoTracker Red® was used to detect Endosomes and Lysosomes. Overlay between micelles and Endo-lysosomes is represented in yellow/orange color (data not shown). As soon as 20 min after incubation, micelles were taken up by the cells and was located in their cytoplasm. After 2 h the uptake was maximal and after 4 to 7 h micelles were detected as defined aggregates inside the cytoplasm. Flow cytometry analysis of HUVEC incubated with rhodamine-labeled polymeric micelles for the same incubation times confirmed a maximal uptake after 2 h (FIG. 7A), while, no difference was observed between 2 to 24 h of incubation. In live-cell analysis, co-localization of Lyso-tracker staining with the micelles suggests endocytosis mechanism of uptake. Incubation of the micelles with HUVEC in cold conditions reduced micelle's uptake by up to 55%, confirming the endocytosis process (data not shown).

MetAP-2 Inhibitor Polymersomes Inhibit Proliferation of Endothelial Cells

Figure 7B:
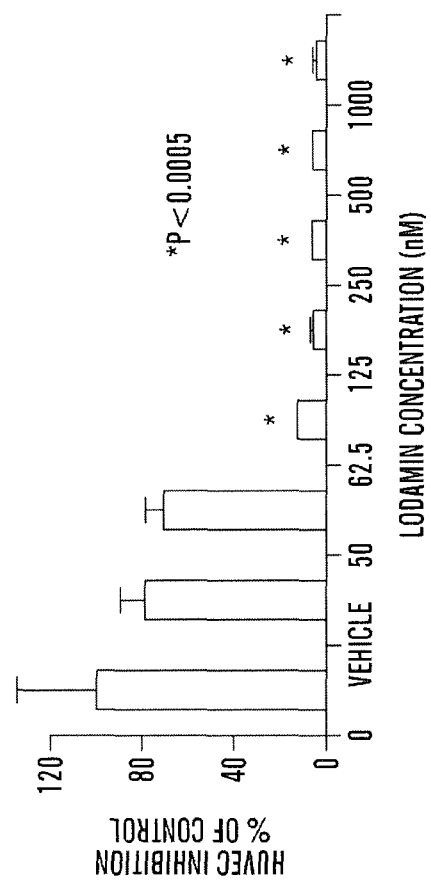
FIG. 7B shows inhibition of HUVEC proliferation by different concentrations of Lodamin 50-1,000 nM TNP-470 equivalent. Empty polymeric micelles were also added as a control (n=8, $*P<0.0005$).
Figures 7C, 7D:
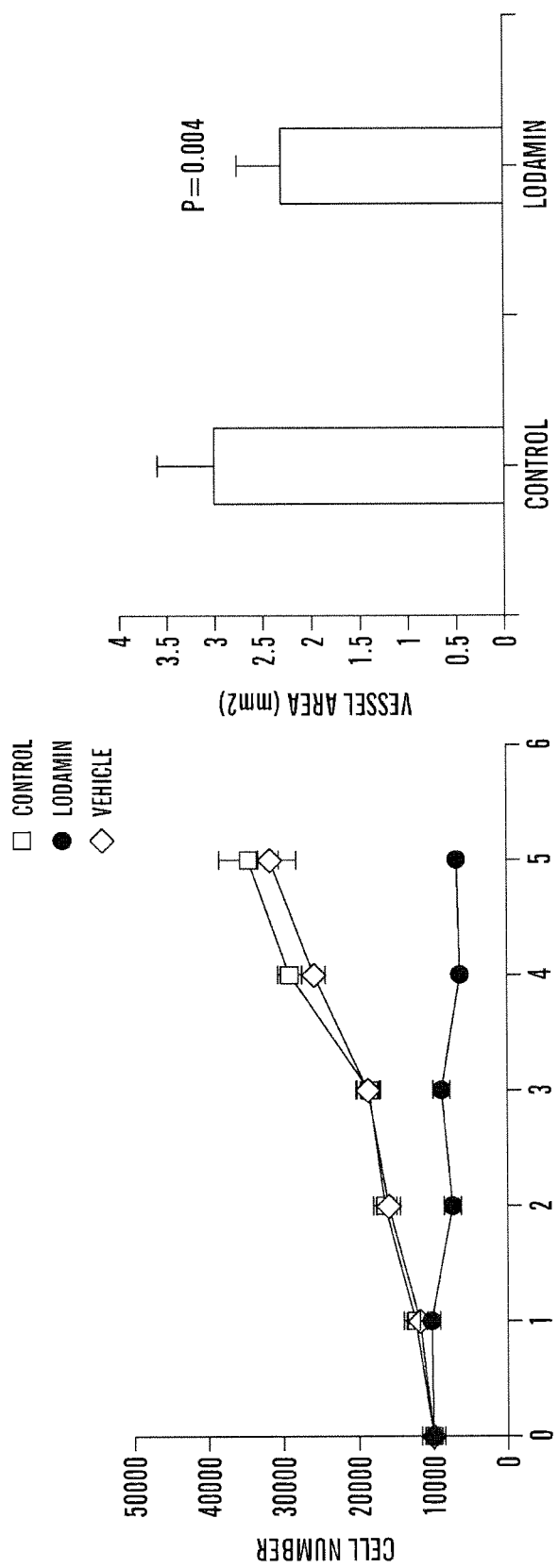
FIG. 7C shows the HUVEC growth curve (●) of cells treated q.o.d. with Lodamin (60 nM TNP-470 equivalent) (□) Untreated cells and (◇) Vehicle treated cells.
FIG. 7D shows shows the quantification of neovascularization area in the cornea in a Corneal Micropocket assay (n=10, mean±SD). Inhibition of angiogenesis in Lodamin treated mouse (15 mg/kg q.d.) with respect to control.

Following polymeric-micelle uptake studies, the effect of Lodamin on the proliferation of endothelial cells was evaluated. Lodamin (62.5 nM-1,000 nM TNP-470 equivalent) inhibited HUVEC proliferation by 88% to 95% respectively after 48 h (FIG. 7B). The growth of HUVEC treated with Lodamin (60 nM TNP-470 equivalent) was completely inhibited compared to untreated cells or cells treated by vehicle only. No substantial cytotoxic effect was found (FIG. 7C).

MetAP-2 Inhibitor Polymersomes Inhibit VEGF and bFGF-Induced Angiogenesis In Vivo The anti-proliferative and antiangiogenic properties of Lodamin were evaluated in-vivo by the corneal micropocket assay[29]. Mice were treated with daily oral Lodamin (15 mg/kg q.d.) or vehicle for 6 d. Newly formed blood vessels grew towards the bFGF pellet (data not shown) in representative eyes of untreated mice. Treated mice show the inhibition of bFGF induced angiogenesis in representative eyes. Quantification of the proliferative area (FIG. 7D) showed 31% inhibition of angiogenesis, compared to vehicle (P=0.00016, n=10). Similar results were obtained with VEGF 165 (160 ng) induced angiogenesis in the cornea (data not shown), in this case Lodamin resulted in 40% inhibition of vessel area.

Polymeric Micelles: Absorption by the Intestine

To study the intestinal absorption of mPEG-PLA-rhodamine micelles, mice were administered oral polymeric-micelles. After 2 h mice were euthanized and isolated segments of the small intestine were fixed and imaged using confocal microscopy. A histological section of gut epithelial cells of Lodamin treated mouse was observed with TEM. The polymeric micelles were intensively taken up by columnar epithelium lining the luminal side of the small intestine. In a high magnification of small intestine villi, micelles are clearly detected in the lamina propria and in the vicinity of the blood vessels, indicating transepithelial absorption. In high resolution TEM images of single gut epithelial cells, many endosomes loaded with the drug were detected (data not shown). Microvilli (MV) structures and endosomes loaded with polymeric micelles (data not shown) are detected. Bar=500 nm (left) and 200 nm (right). Confocal microscopy image also confirms the TEM observations. Note the polymeric micelles can be detected in the lamina propria in the vicinity of blood vessels. The actin filaments were stained with phalloidin-FITC, nuclei were labeled with DAPI and mPEG-PLA were labeled with rhodamine, bars=5 µm. These vesicles were different in contrast and number than in an intestine of untreated mouse. These data support the premise that Lodamin was absorbed by the villous structure of the intestine by endocytosis.

Body Distribution of Polymeric-Micelles, Accumulations in Tumors and Toxicity

Figure 8D:
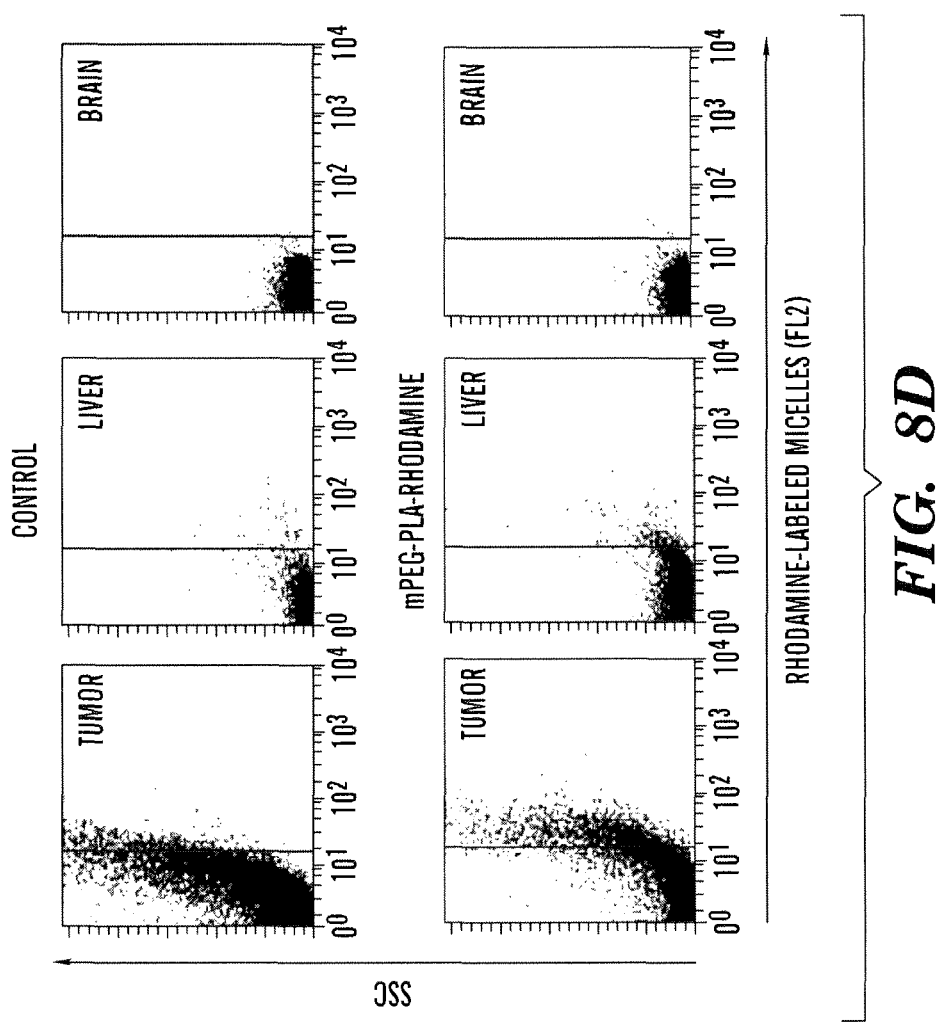
FIG. 8D shows the FACS analysis graphs of single-cell suspensions from three representative organs (tumor, liver, brain) taken from a mouse bearing Lewis lung carcinoma after controlled enzymatic degradation. The $FL2^{high}$ represents those cells that contain the mPEG-PLA-rhodamine micelles.

The biodistribution and tissue uptake of orally administered labeled MetAP-2 inhibitor polymersomes were studied by treating mice with fluorescent labeled PEG-PLA micelles for 3 d. After harvesting the tissue, tissue drug concentration was quantified by dye extraction or by flow cytometry. The results of the fluorescent dye extraction method (FIG. 8A) showed that as expected, a high concentration of fluorescent signal was detected in the stomach and the small intestine, where the liver showed the highest level. Importantly, the brain showed no presence of fluorescent signal. In the serum, labeled micelles were already detected after 1 h post oral administration, peaking after 2 h and were still detected up to 72 h. Accordingly, in tumor bearing mice, flow cytometry analysis of enzymatically digested tissues (FIGS. 8C and D) demonstrated a large uptake of labeled micelles by the liver, and no uptake by brain cells. Importantly, the highest uptake of micelles was detected in tumor cells. In FIG. 8C the percentage of $FL2^{high}$ cells, i.e. cells that absorbed rhodamine-labeled micelles is demonstrated. Taken together, these results indicate that the drug is mostly concentrated in the tumor and in the gastrointestinal organs (although to a lower extent) and not in the brain.

No tissue abnormalities were detected in histological analysis (H&E) of liver, intestine, lung and kidneys of MetAP-2 inhibitor polymersome treated mice (15 mg/kg TNP-470 equivalent q.d., for 20 d) when compared to untreated mice (data not shown). In addition, no significant differences were found in mouse serum liver-enzyme profile of MetAP-2 inhibitor polymersome treated mice compared to untreated mice. In Lodamin treated group ALT concentration was 41±9 u/l and AST was 120±39 u/l whereas in the untreated group the ALT concentration was 37.5±4 u/l and AST concentration was 152±131 u/l.

MetAP-2 Inhibitor Polymersomes Inhibit Primary Tumor Growth

Figures 9A, 9B:
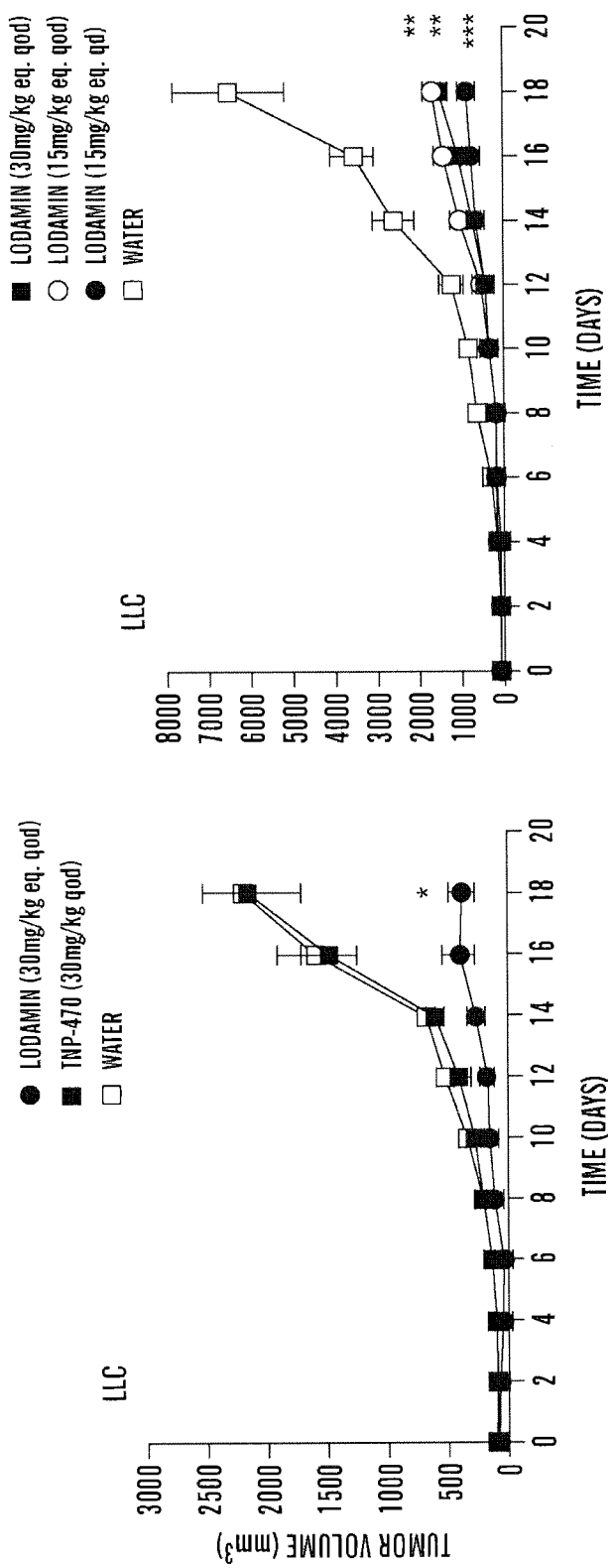
FIG. 9A shows the effect of free or conjugated TNP-470 on established primary tumor-Lewis lung carcinoma tumors: effect of 30 mg/kg. q.o.d. of free TNP-470 (■) given orally, compared to equivalent dose of Lodamin (x) or water (□), (n=5 mice per group, $*P<0.05$).
FIG. 9B shows the Lewis lung carcinoma volume during 18 d of different frequencies and doses of Lodamin: 30 mg/kg. q.o.d. (x), 15 mg/kg q.o.d. (○), 15 mg/kg q.d. (●), and water (□) by gavage (n=5 mice per group, $*P<0.05$.

The biological efficacy of Lodamin was evaluated as an anti-cancer agent in tumor bearing mice. When mice were given oral free TNP-470 at a dose of (30 mg/kg q.o.d.) no inhibition in the growth of subcutaneous LLC tumors was observe (FIG. 9A). The equivalent dose of Lodamin, however, resulted in a significant inhibition of tumor growth (FIG. 9A). This inhibition was observed after 12 d of Lodamin treatment, and at day 18 tumor growth was inhibited by 83%. Different dosing strategies of Lodamin were tested: 15 mg/kg q.d., 30 mg/kg q.o.d. and 15 mg/kg q.o.d., resulting 87%, 77%, and 74% of tumor volume inhibition respectively (FIG. 9B). The vehicle (PEG-PLA) showed no effect on tumor growth and was similar to untreated control mice (FIG. 9C).

Figure 9F:
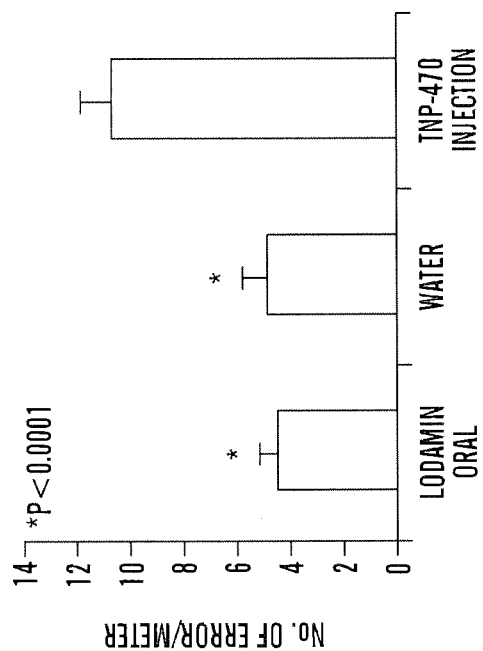
FIG. 9F shows the neurotoxcity of Lodamin on treated mice (10 d, 30 mg/kg q.o.d.) compared to mice treated with subcutaneous (30 mg/kg q.o.d.) free TNP-470 or water given by gavage. Balance beam test was quantified by foot-slip errors and the numbers of slips per meter are presented (n=4-5 mice per group). $*P<0.05$, $P<0.01$, $*P<0.0001$ (results are mean±SE).
Figure 9E:
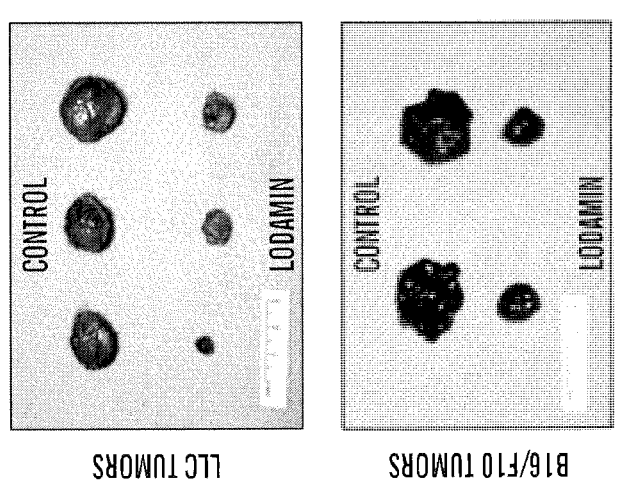
FIG. 9E shows some representative Lewis lung carcinoma and B16/F10 tumors removed from mice at day 18 post treatment with oral Lodamin at 30 mg/kg q.o.d., and 15 mg/kg e.d. respectively, and from control untreated mice.

In another tumor model, B16/F10 melanoma tumors were induced subcutaneously and their growth was also inhibited by oral Lodamin (15 mg/kg q.d.). This treatment was effective as of day 4, and after 13 d 77% volume inhibition was obtained (FIG. 9D). No apparent side-effects or weight loss were detected in either tumor models. Higher doses of Lodamin: 30 mg/kg q.d., and 60 mg/kg. q.o.d., showed substantial tumor inhibition, however, it was accompanied by weight loss (data not shown). FIG. 9E shows representative tumors of treated or untreated LLC or B16/F10 tumors.

MetAP-2 Inhibitor Polymersomes Did not Cause Neurotoxicity in Mice

Since the biodistribution study indicated that Lodamin does not cross the blood brain barrier, we further tested if the possible penetration of escaped free drug into the brain might still result in neurotoxicty and cerebellar dysfunction. To examine this, mice were subjected to a sensitive test of motor coordination: crossing a narrow (4 mm) balance beam30. As shown in FIG. 9F Lodamin-treated mice (30 mg/kg q.o.d. for 14 d) performed in this challenge similar to control (water treated) mice, whereas mice injected with free TNP-470 (30 mg/kg q.o.d.) committed over twice as many errors (P<0.0001). These results indicate that Lodamin treatment avoids the cerebellar neurotoxicity observed with unconjugated TNP-470 treatment.

Oral MetAP-2 Inhibitor Polymersomes Inhibit Angiogenesis and Cell Proliferation in Tumors and Induce Tumor Cell Apoptosis The effect of Lodamin on the histological structure of the LLC tumors was tested. Both treated and untreated tumors showed a dense cellular structure (data not shown). Lewis lung carcinoma (LLC) tumors were removed from Lodamin treated or untreated mice and sectioned. Tissues were stained with Hematoxylin & Eosin (H&E) to detect tissue morphology. Immunostaining with anti-CD31 was used to detect microvesselsand anti-Ki67 nuclear antigen for cell proliferation. TUNEL staining was used for the detection of apoptotic cells. Cell nuclei were stained with DAPI. Sections were counterstained with Eosin (nuclei). The tumors of untreated mice had a net organization of small and large vessels with apparent lumen structure as demonstrated by CD-31 immunostaining. In contrast, Lodamin treated tumors formed very small undeveloped vessels (data not shown). Lodamin treated tumors showed less cellular proliferation than untreated tumors, as detected by the nuclear marker KI-67. TUNEL staining for the detection of apoptosis in the tissues indicated an enhanced apoptosis in Lodamin treated tumors. Lodamin treated tumor had less vessels but high levels of apoptosis predominantly of tumor cells. In the control tissue, apoptotic cells were found in the capsule of the tumor but less in the center of the tissue.

Figure 9G:
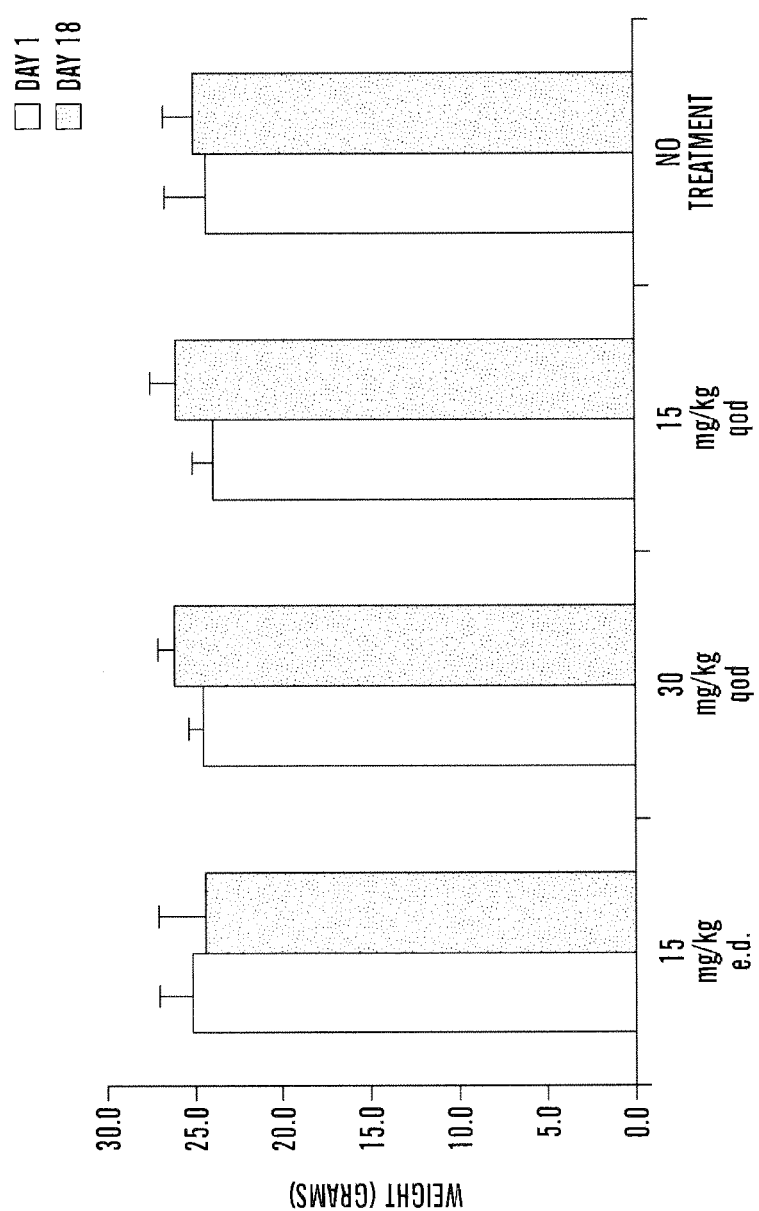
FIG. 9G shows the mice's weight on day 1 and day 18 post treatment with oral polymeric micelle TNP-470 (Lodamin).

In addition, the new oral formulation of the MetAP-2 inhibitor TNP-470 did not cause any weight loss or other apparent side-effects in the mice (FIG. 9G).

MetAP-2 Inhibitor Polymersomes Prevent Development of Liver Metastasis

Figure 10A:
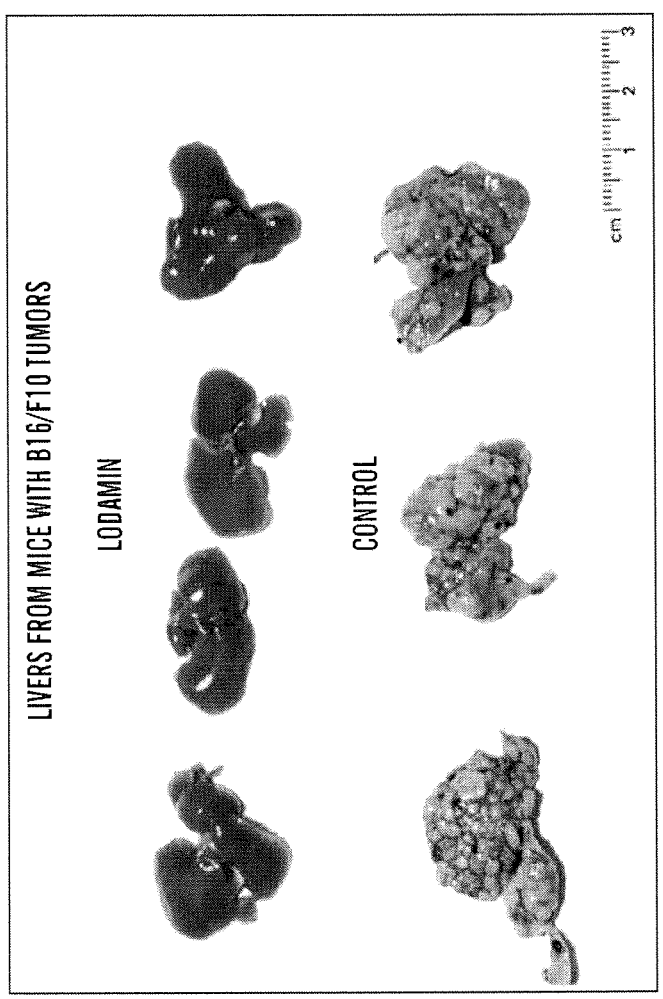
FIG. 10A shows the livers removed from Lodamin-treated or untreated mice with B16/F10 tumors, 20 d post cell injection. Control livers were enlarged with wide-spread macroscopic malignant nodules and extensive cirrhosis.
Figure 10C:
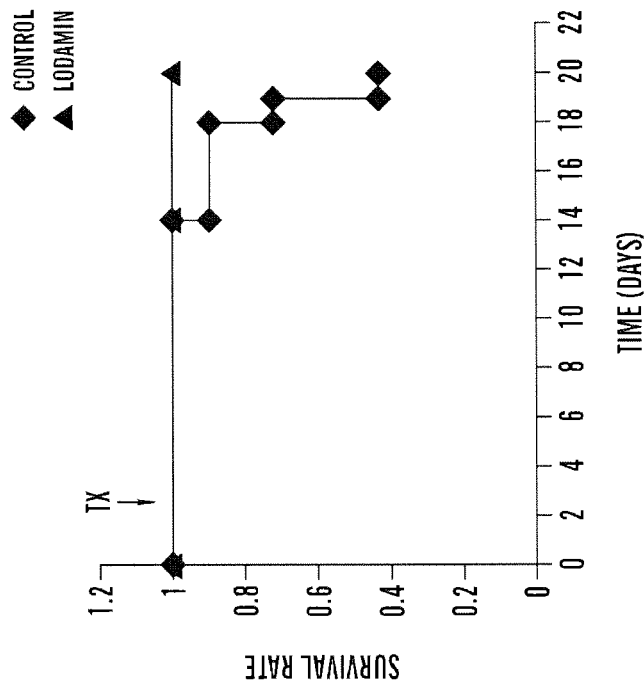
FIG. 10C shows the survival curve of treated versus control mice with B16/F10 tumors (n=7). Treatment started at day three (TX) after cell injection (arrow).
Figure 10B:
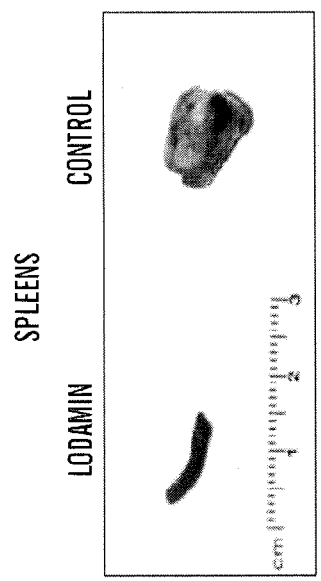
FIG. 10B shows the spleens removed from Lodamin-treated or untreated mice with B16/F10 tumors. Control spleens had large masses compared to treated mice with normal spleen morphology.

The effect of oral Lodamin administration on liver metastases was tested after spleen injection of B16/F10. Oral Lodamin treatment dramatically affected development of liver metastasis. After 18 d of treatment mice were autopsied. All untreated mice had ascites while their enlarged livers had macroscopic malignant nodules and extensive cirrhosis, (FIG. 10A). In contrast, Lodamin-treated mice had no macroscopic metastasis in the abdomen and in the liver (FIG. 10A). Their organs had normal morphology and no weight-loss or other apparent side-effects were found. Immunohistology showed only a few sporadic B16/F10 cells in the liver, which had not developed into lesions (data not shown). Only one treated mouse out of seven had malignant nodules in its liver, but the liver was smaller than in the untreated control and had less cirrhosis. The spleens of all Lodamin treated mice had normal morphology compared to the congestion found in the enlarged spleens of control mice (FIG. 10B). Twenty days post B16/F10 cell injection into the spleen, 4 out of 7 control mice had died while all treated mice survived (FIG. 10C).

In this study, the inventors describe for the first time the development of a nontoxic oral formulation of the MetAP-2 inhibitor TNP-470, named Lodamin, as a potent anti-proliferative and anti-metastatic drug. TNP-470, a highly potent anti-proliferative/antiangiogenesis agent, is a leading candidate for chronic administration for cancer maintenance therapy and metastasis prevention.

The challenge that the inventors faced was based on the fact that TNP-470 has very poor oral availability as illustrated by its high Log D values, indicating low water solubility[35]. In order to make the drug suitable for oral administration, this property of TNP-470 was altered while retaining its activity by conjugating it with mPEG-PLA to form mPEG-PLA-TNP-470 polymeric micelles i.e. Lodamin. Unlike TNP-470 which is only dissolvable in organic solvents, Lodamin can be suspended in water to form polymeric micelles caused by the amphiphilic nature of PEG-PLA[26]. In this structure the drug is located in the core of the micelle protected from the harsh gastrointestinal environment[36]. Polymer micelles have previously been used for the delivery of hydrophobic drugs[37,38] and gene delivery[39]. Lodamin acquired a stable spherical morphology of nanomicelles, as imaged by TEM. In addition, PLA which is a biodegradable and biocompatible polymer, hydrolyzes in an aqueous environment and allows a slow-release of TNP-470. In-vitro studies showed a continuous release of TNP-470 from Lodamin over almost a month period, where the majority of the drug was released after 4 d (in both gastric and plasma pH conditions), although acidic environment is known to accelerate degradation of PLA we observed only a minor effect on day 15. While not wishing to be bound by theory, one possible explanation may be the masking effect of the PEG shell which delays the water penetration to the PLA core and slows the release of the drug through diffusion of this layer. In culture, Lodamin was rapidly taken up by endothelial cells via endocytosis and retained the original antiangiogenic activity of the free TNP-470 as demonstrated by the inhibition of HUVEC proliferation and growth rate.

PEG-PLA micelles penetrated the gut epithelial layer into the submucosa as shown by using fluorescent marker. The mechanism of Lodamin penetration to gut epithelial cells seems to be via endocytosis as detected by high resolution TEM imaging. In serum, labeled micelles had long blood circulation time of at least 72 h post administration, a significant increase compared to free drug which was detected in mice sera up to 2 h post-administration. Biodistribution showed relatively high concentration in the liver because oral administration delivers the drug directly from the intestine to the liver. However, no liver toxicity was observed by histology and by liver enzymes profile after 20 d of daily Lodamin treatment.

Lodamin given orally to mice showed substantial anti-proliferative effects (83% reduction), while free TNP-470 given orally had no effect. The effect on LLC growth was dose dependent, as 30 mg/kg q.o.d. was more effective than 15 mg/kg. q.o.d., and a dose of daily 15 mg/kg q.d. was more effective than 30 mg/kg q.o.d. (a double dose given every 2 d). A similar anti-proliferative effect of Lodamin was also observed with melanoma B16/F10 tumors, confirming the broad biological effect of Lodamin, very much like the original free TNP-470. Immunohistochemical studies carried out on LLC tumor tissues showed a reduction of proliferation and angiogenesis induced by Lodamin. Using TUNEL staining we detected a high level of tumor cell apoptosis following the Lodamin treatment, whereas in the controls much of the apoptosis occurred on the capsule of the tumor. These results indicate that the prevention of angiogenesis by Lodamin leads to tumor cell apoptosis, thus making Lodamin a cytotoxic drug, in addition to an antiangiogenic drug.

One of the most notable effects of oral Lodamin is the prevention of liver metastasis in mice. Liver metastasis is very common in many tumor types and has often been associated with poor prognosis and survival rate. The inventors chose the intrasplenic model for induction of liver metastasis, in which the transition time of B16/F10 from spleen to liver microvasculature post spleen injection in mice was found to be very fast (20% of the injected cells after 15 min) 40. Mice injected with B16/F10 cells into the spleen had a low survival rate. They developed ascites, macroscopic malignant nodules, and extensive cirrhosis in their livers 20 d post injection. However, all oral Lodamin treated mice survived up to this point and had normal liver (except one mouse) and spleen morphology without any other apparent side-effects. Immunohistology of treated mice's livers showed some rare sporadic B16/F10 cells which remained dormant over the 18 d of oral Lodamin treatment, compared to large metastasic tumors found in the untreated mice. It should be noted that Lodamin's effect on secondary tumor growth is in addition to its effect on the primary tumor.

While not wishing to be bound by theory, this dramatic effect may be due to the oral route of administration in which Lodamin is absorbed in the gastrointestinal tract and concentrated in large quantities in the liver via the portal vein. These results indicate that Lodamin can prevent the development of metastasis in the liver associated with different tumor types. Importantly, this property of the polymeric micelles might be used for enabling oral availability of other antiangiogenic or anti-cancer drugs to target liver metastasis.

In summary, oral Lodamin is therapeutically effective in the treatment of solid tumors and metastasis in mice. It captures the antiproliferative properties of free TNP-470 while adding important advantages: oral availability, improved biodistribution, tumor accumulation, continual release, improved solubility, proper clearance, and low related side-effects. In addition to use for the treatment or suppression of known, existing tumors, its use is contemplated, among others, for cancer patients as a long-term maintenance angiogenesis inhibitor to prevent tumor recurrence. Furthermore, it is also contemplated for use as maintenance therapy for chronic MetAP-2-related diseases such as age-related macular degeneration, endometriosis and rheumatoid arthritis. Other contemplated uses are described elsewhere herein.

Example 4

MetAP-2 Inhibitor Polymersomes Inhibit Glioblastoma Tumor Growth

Figure 11A:
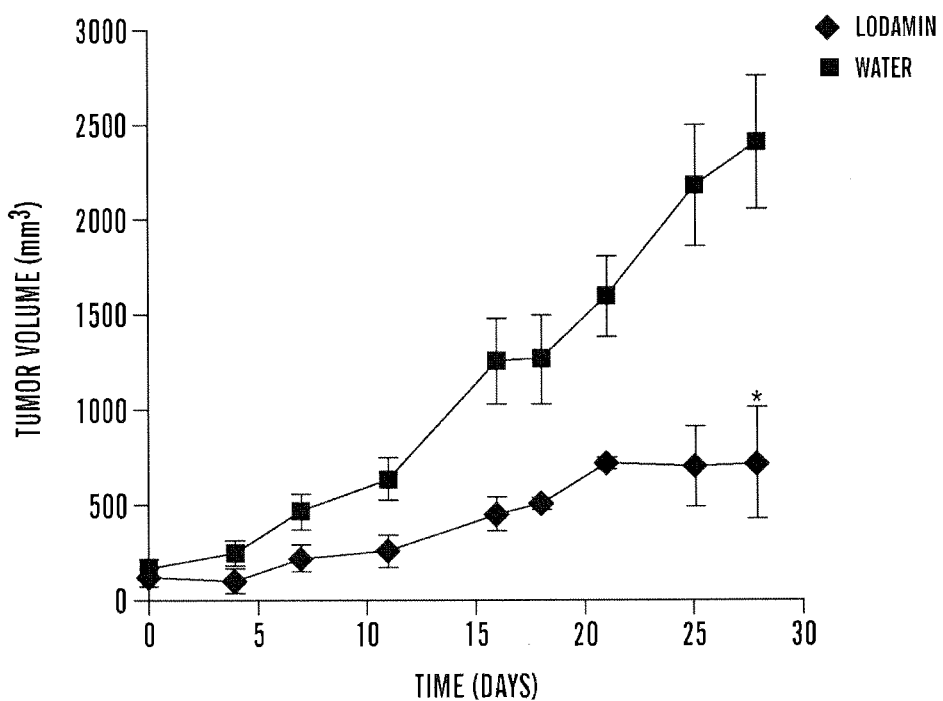
FIG. 11A shows the effect of Lodamin administered orally by gavage on established human glioblastoma tumors (U87-MG tumors) growth in nude mice: 15 mg/kg. q.d of Lodmain (solid diamonds) given orally, water (solid squares), (n=5-10 mice per group, *p<0.05).
Figure 11B:
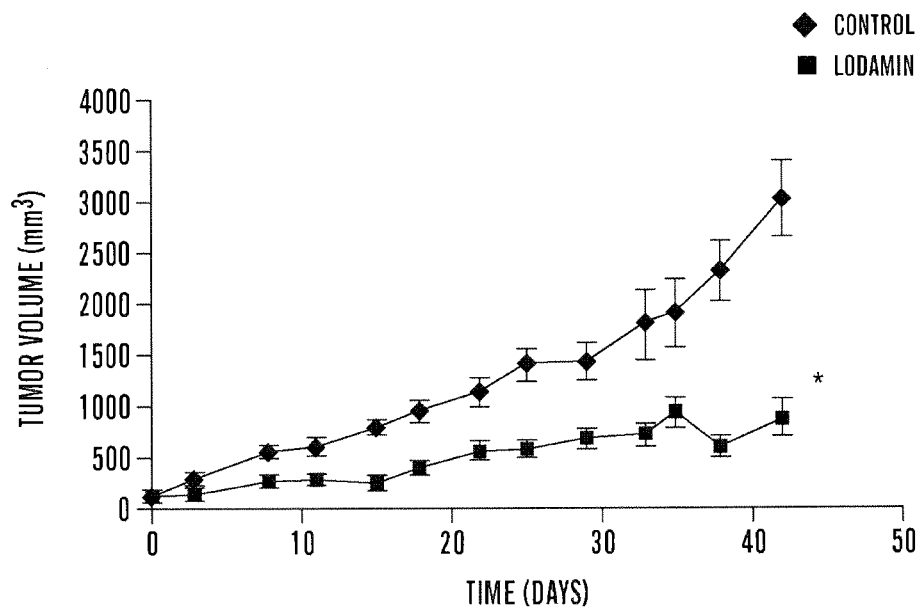
FIG. 11B shows the effect of Lodamin given in drinking water at a dose of 15 mg/kg q.d. (solid squares), water with Lodamin was changed every 3 days. *p<0.05 (results are mean±SE). The mice had established human glioblastoma tumors (U87-MG tumors) growth.

The effect of Lodamin on human brain tumor (U87MG, Glioblastoma) was studied using subcutaneous tumor-bearing nude mice. Treatment with Lodamin started when tumors were in volume of ~100 mm$^3$. Lodamin that was given by gavage (FIG. 11A) in a daily dose of 15 mg/kg TNP-470 equivalent, inhibited tumor volume by 70% after 30 days. When Lodamin was given in drinking water at the same dose (FIG. 11B) a 71% inhibition of tumor volume was obtained after 42 days.

Example 5

MetAP-2 Inhibitor Polymersomes Prolong Survival of Mice Bearing Lung Metastasis

C57/Bl mice were injected into their tail-veins with 2.5×10$^5$ B16/F10 cells. Day after injection the mice were divided into 3 groups: 10 mice were given a daily oral administration of Lodamin (15 mg/kg TNP-470 equivalent), 9 mice were given IP injection with the same Lodamin dose, and 10 mice remained untreated. Mice survival was followed up to 40 days post treatment.

Figure 12:
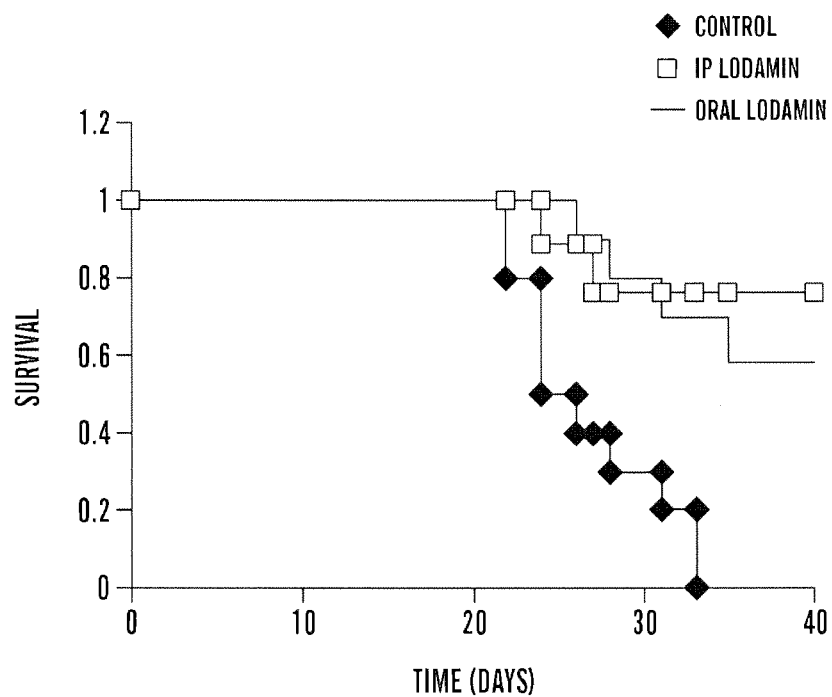
FIG. 12 shows the Kaplan-Meier survival curve of C57/Bl mice treated with Lodamin given at a dose of 15 mg/kg q.d TNP-470 equivalent IP (n=9, white squares), oral (n=10, solid line) or without any treatment (n=10, diamond black).

Lodamin treated mice showed a prolonged survival as can be seen in Kaplan-Meier survival curve (FIG. 12). After 32 days all control mice died, compared to 6 and 5 mice that lived at day 40 in the IP Lodamin treated group and Oral Lodamin group respectively.

Example 6

MetAP-2 Inhibitor Polymersomes Inhibit Angiogenesis in Matrigel Angiogenesis

In-Vivo Matrigel Angiogenesis Assay was conducted in order to assess the antiangiogenic properties of Lodamin. Matrigel (BD bioscience) which was remained in 4° C. overnight was mixed with fibroblast growth factor-2 (FGF-2) to obtain a final FGF-2 concentration of 1 μg/ml. Nine C57/Bl mice were injected with Matrigel (500 μl) in two sites subcutaneously. Three mice got a daily oral treatment with Lodamin (15 mk/kg/day TNP-470 equivalent). In three mice the Matrigel was mixed with Lodamin (5 mg/ml) and no further treatment was performed and three untreated mice with Matrigel implant were used as a control.

After 8 days, mice were euthanized and the Matrigel implant harvested, washed twice with PBS, and then one of the implant was immediately frozen on dry ice and used for histology assessment of blood vessels using CD-31 antibody. The second implant was enzymaticaly digested using collagenase (Librease, Roche) to obtain single cell suspension which again was analyzed by FACS to quantify the number of endothelial cells using CD-31 and CD-45 antibodies (endothelial cells are CD31+CD45−).

Figure 13A:
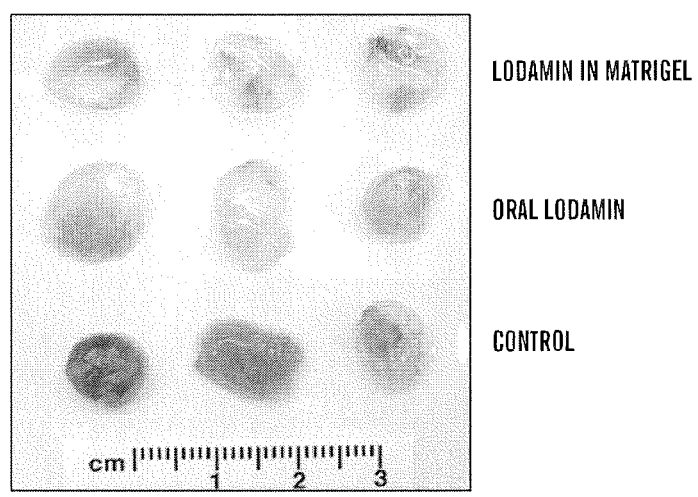
FIG. 13A shows the effects of Lodamin on angiogenesis in Matrigel implants, the implants were removed 8 days post injection from mice.
Figure 13B:
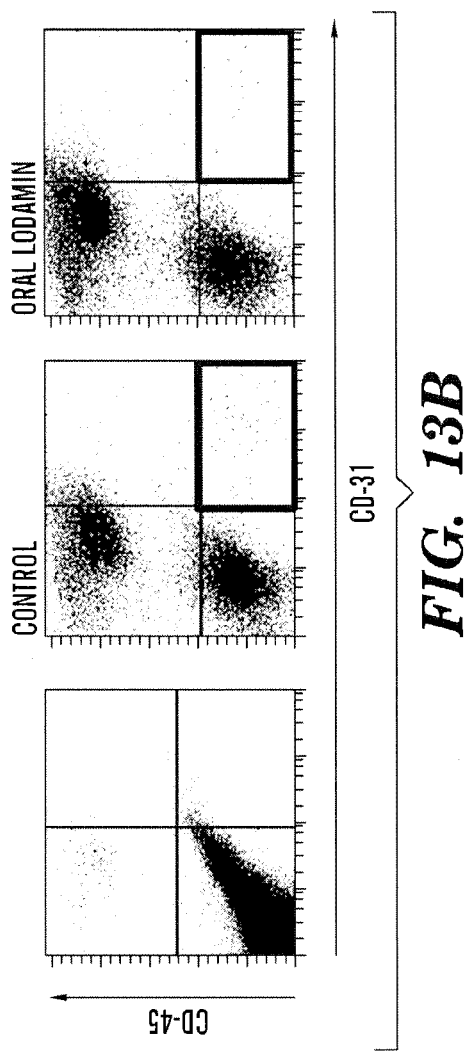
FIG. 13B shows FACS analysis of the Matrigel incorporated cells in Lodamin-treated and non-treated mice, CD45-CD31+ represents the endothelial cells.

The implants of Lodamin treated mice, both the one with the mixture of matrigel and Lodamin or the mice treated orally with Lodamin, showed a significant reduction in blood vessels inside the implants (FIG. 13A). Histology showed less vessels in Lodamin treated mice and less dense tissue. FACS analysis suggests 70% reduction in the percent of endothelial cells which were attracted to the implant (FIG. 13B).

Example 7

Lodamin has Anti-Inflammation Activity

Figure 16:
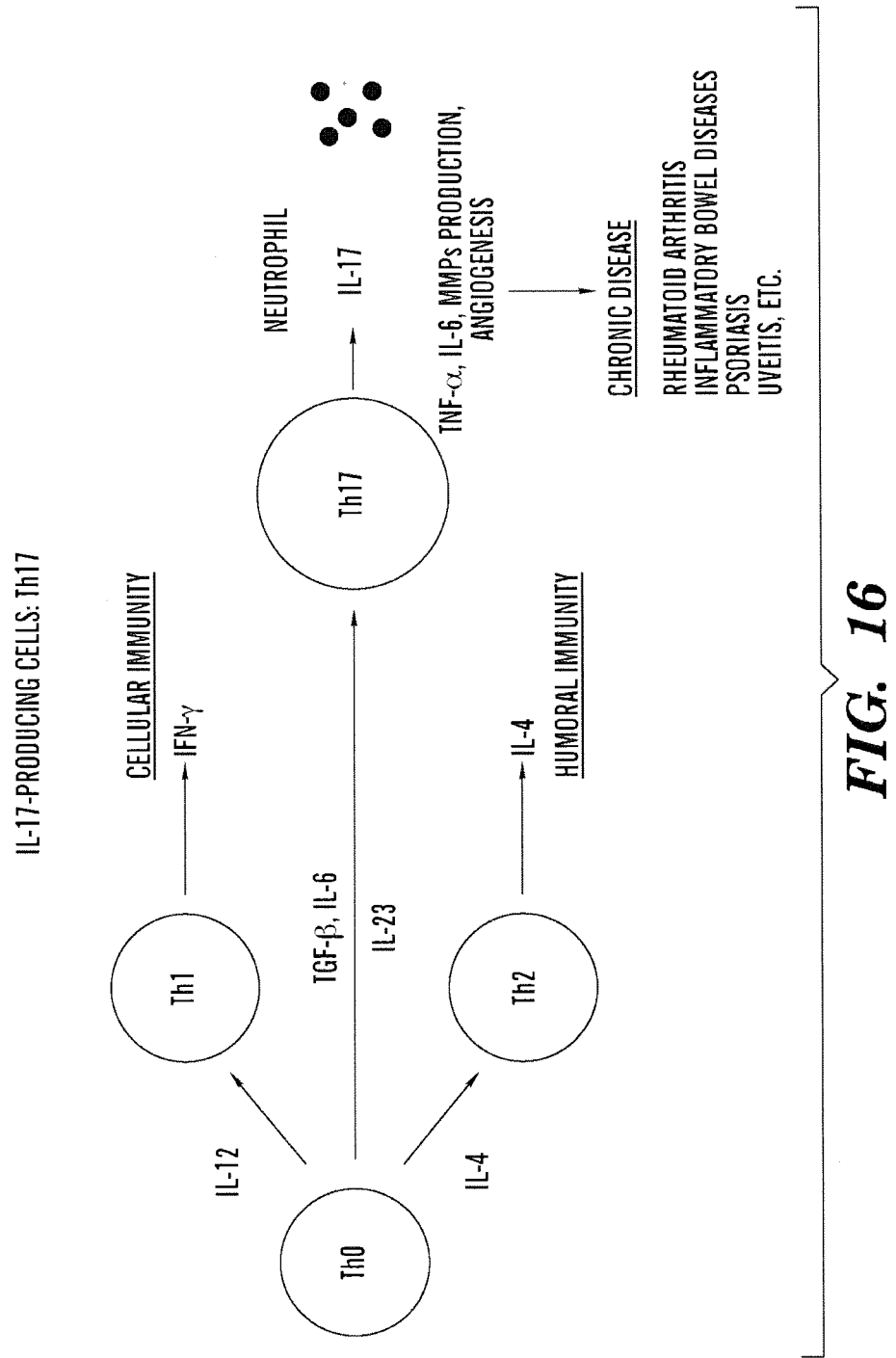
FIG. 16 is a schematic diagram showing the activation of Th17 cells and the role of Th17 cell play in T-cell mediated inflammation and T cell mediated diseases such as autoimmune diseases.
Figure 17:
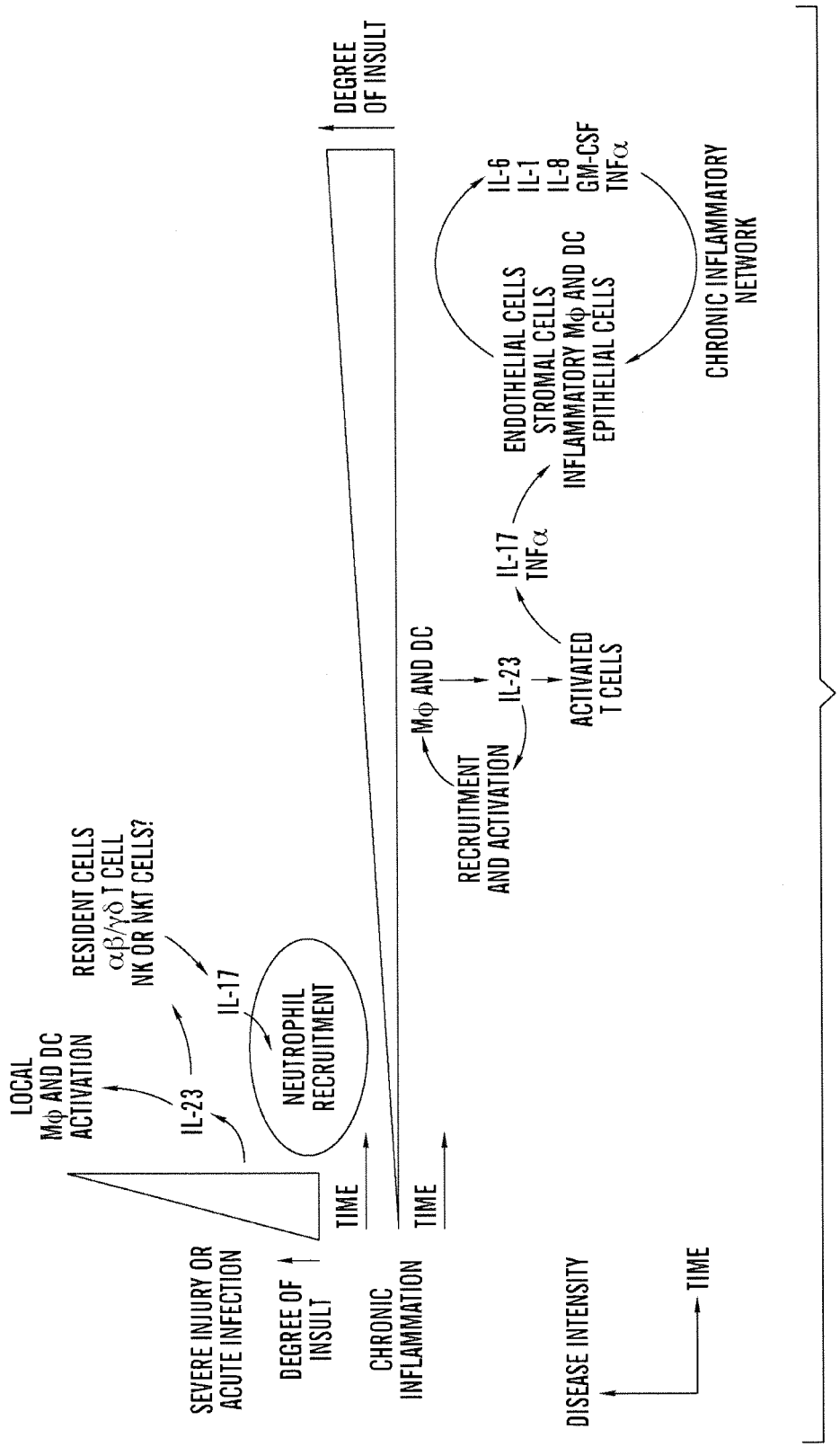
FIG. 17 is a schematic diagram showing the effects of IL-17 in acute and chronic inflammation.

Activation of Th17 cells plays an important role in the immune system in response to infection, injury, irritant and external insult to the body. Activated Th17 cells secrete a number of cytokines: IL-17, TNF-α, IL-6 etc; induced MMP production and promote angiogenesis, and recruit other immune cells such as neutrophils (FIG. 16). However, prolong activation of Th17 cells have been shown to lead to chronic diseases such as rheumatoih arthritis, inflammatory bowol diseases, psoriasis and uveitis to name a few (FIG. 17) (Nature 2, 20028, 453:1051-1057; Annu. Rev. Immunol. 2009, 27:485-517).

Human endogenous uveitis, such as Behcet's disease, Vogt-Koyanagi-Harada disease, Sarcoidosis, is known to be one of the sight-threatening intraocular diseases. Complications, such as cystoid macular edema, secondary glaucoma and proliferative vitreoretinopathy, can cause permanent loss of vision.

Uveitis encompasses all inflammatory processes of the middle layers of the eye, also called the uveal tract or uvea. The uvea includes the iris (colored part of the eye), choroid (a thin membrane containing many blood vessels) and ciliary body (the part of the eye that joins these together). The uvea is very important because its many veins and arteries transport blood to the parts of the eye that are critical for vision. Uveitis may cause inflammation of all three structures that make up the uvea. Alternately, only one of the structures may be affected. For instance, in the type of uveitis affecting only the iris, the condition is caller iritis, or anterior uveitis. Intermediate uveitis is also known as iridocyclitis, and posterior uveitis is known as choroiditis or chorioretinitis.

Figure 18A:
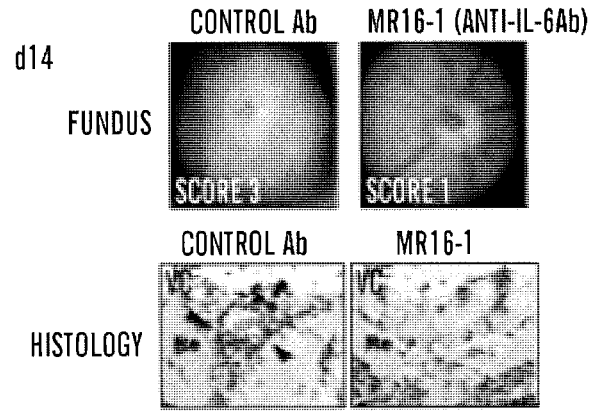
FIG. 18A shows the Experimental Autoimmune Uveitis (EAU) as a model of human endogenous uveitis. After immunizing C57BL/6 mice with interphotoreceptor retinoid-binding protein, IRBP), EAU severity was assessed clinically and histopathologically. This autoimmune disease model is a T-cell mediated disease and Th17 cells have been implicated in the pathogenesis of the disease (Rheumatology, 2009, 48: 347-54).

As an inflammatory eye condition, uveitis can occur alone or it can occur as part of a generalized inflammatory process in systemic autoimmune diseases. In many cases of uveitis, several immunosuppressive drugs are needed to control the inflammation process in the eye. However, long-term administration of these drugs can cause severe side effects. FIG. 18A shows the Experimental Autoimmune Uveitis, (EAU) as a model of human endogenous uveitis. After immunizing C57BL/6 mice with interphotoreceptor retinoid-binding protein, IRBP), EAU severity was assessed by clinically and histopathologically. This autoimmune disease model is T-cell mediated disease and Th17 cells have been implicated in the pathogenesis of the disease.

Figure 18B:
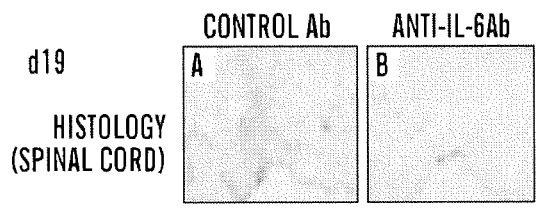
FIG. 18B shows the Experimental Allergic (Autoimmune) Encephalomyelitis (EAE) as a model of human multiple sclerosis. The C57BL/6 mice were immunized with myelin oligodendrocyte glycoprotein (MOG), after which the paralysis severity is assessed. This autoimmune disease model is a T-cell mediated disease and Th17 cells have been implicated in the pathogenesis of the disease (PNAS, 2008, 105:9041-6).

Multiple sclerosis (MS) is a chronic inflammatory autoimmune disease affecting the central nervous system. Previous studies of Experimental Autoimmune Encephalomyelitis (EAE), a murine model of MS, indicated that autoimmune responses were initiated by a subset of myelin-specific $CD4^+$ T cells. FIG. 18B shows the Experimental Allergic (Autoimmune) Encephalomyelitis, EAE as a model of human multiple sclerosis. The C57BL/6 mice were immunized with myelin oligodendrocyte glycoprotein (MOG), after which the paralysis severity will be assessed. This autoimmune disease model is T-cell mediated disease and Th17 cells have been implicated in the pathogenesis of the disease.

Figure 19:
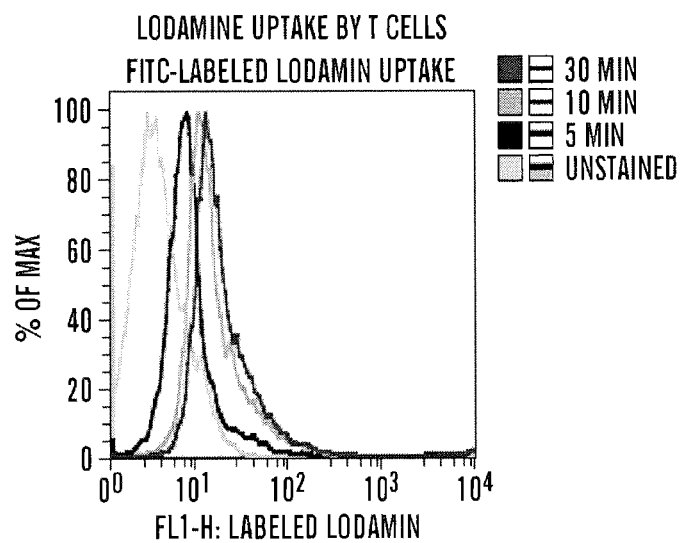
FIG. 19 shows the FITC-labeled Lodamin uptake by T cells. CD4+ cells were purified from splenocytes and lymph nodes cells by MACS, then cultured with 6-coumarin-labeled Lodamin for the indicated minutes. Fluorescence intensity was analyzed by flow cytometry.

Lodamin has previously been shown to inhibit angiogenesis and tumor growth by oral administration without adverse side effects. To confirm that Lodamin can be uptaken by T cells, fluorescence-labeled Lodamin were used; FIG. 19 shows the FITC-labeled Lodamin uptake by T cells. $CD4^+$ cells were purified from splenocytes and lymph nodes cells by MACS, then cultured with 6-coumarin-labeled Lodamin for the indicated minutes. Fluorescence intensity was analyzed by flow cytometry. Lodamin was uptaken the T cells within 5 minutes of incubation and after 10 minutes the cells were saturated with the drug. This data indicate fast endocytosis kinetics.

Figure 20:
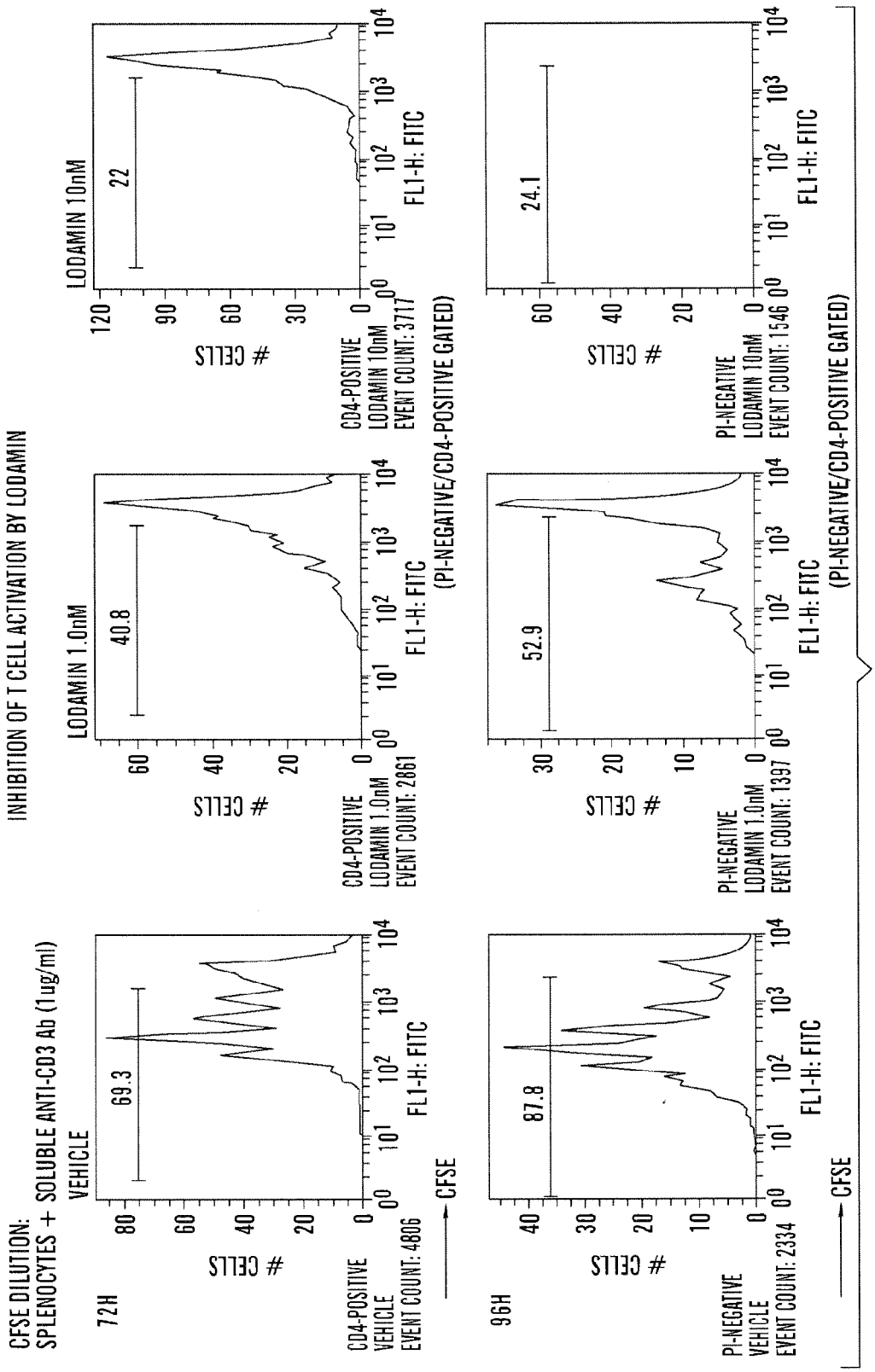
FIG. 20 shows the inhibition of T cell proliferation by Lodamin after 72 and 96 hours using carboxyfluorescein succinimidyl ester (CFSE) dye.

Cellular proliferation is an essential feature of the adaptive immune response. In order to evaluate Lodamin's potential in inhibitng T cell proliferation, a calorimetric technique was used. Carboxyfluorescein succinimidyl ester (CFSE) dye was used to stain and monitor the number of cell divisions during cell proliferation. To evaluate the effect of Lodamin for T cell proliferation, T cells were stained with CFSE dye and stimulated with anti-CD3 antibody. FIG. 20 shows the inhibition of T cell proliferation by Lodamin after 72 and 96 hours using CFSE dilution.

Figure 21:
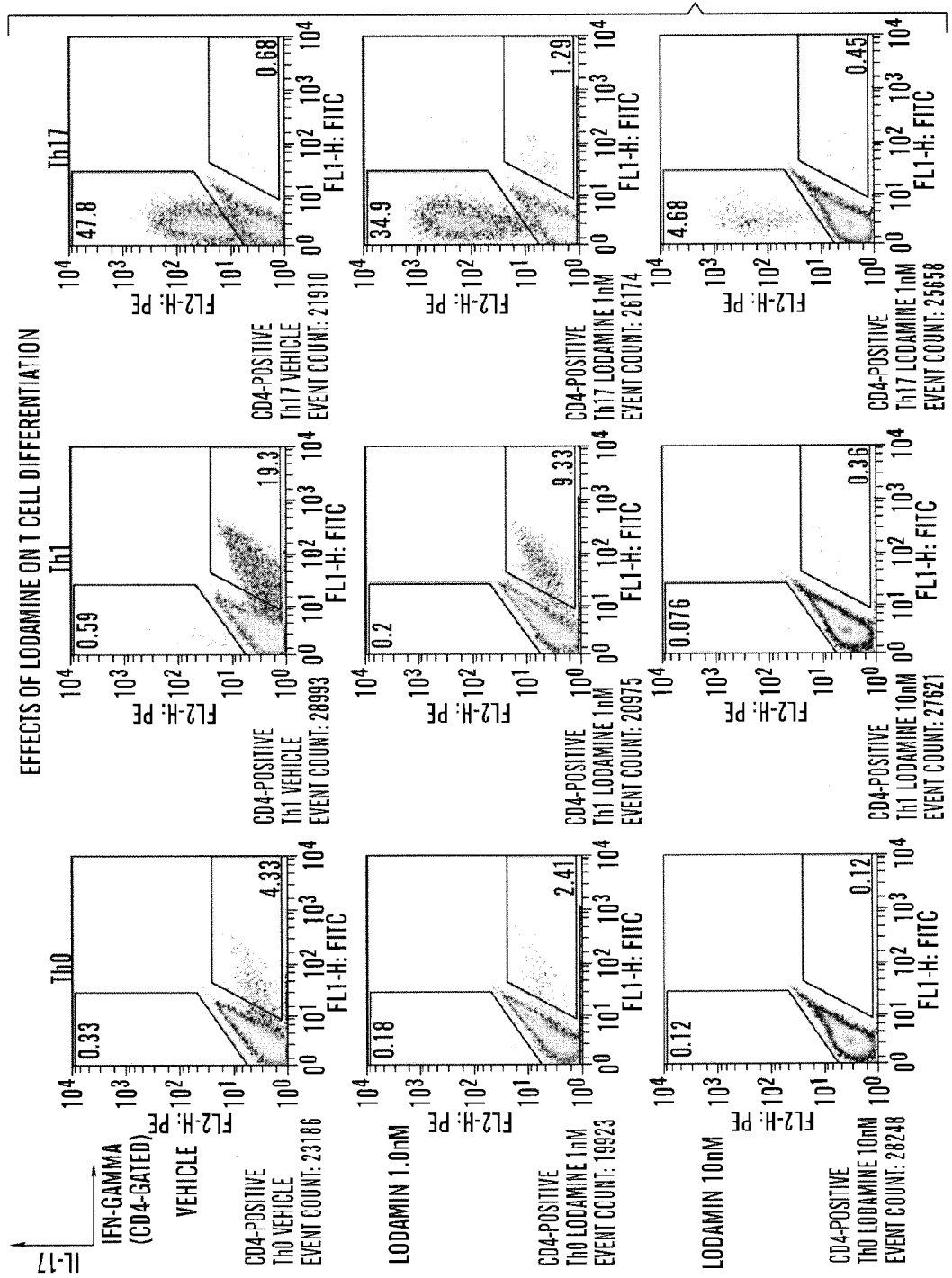
FIG. 21 shows the effects of Lodamin on T cell differentiation as analyzed by intracellular cytokine staining. Whole splenocytes were stimulated with soluble anti-CD3 (1 µg/ml) under the following conditions for 72 h: Th0 condition: anti-IFNγ Ab (1 µg/ml), anti-IL-4 Ab (1 µg/ml); Th1 condition: IL-12 (10 ng/ml), anti-IL-4 Ab (1 µg/ml); Th17 condition: TGFβ1 (2 ng/ml), IL-6 (20 ng/ml), anti-IFNγ Ab (1 µg/ml), anti-IL-4 Ab (1 µg/ml) in the presence of vehicle (control, no Lodamin), Lodamin 1.0 nM, and Lodamin 10 nM as indicated. Expansion of Th1/Th17 cells was evaluated by intracellular cytokine staining.

IL-17-producing T cells have recently been classified as a new effector T cell subset. Th17, are different from Th1 and Th2 subsets and they play a significant role in autoimmune disease progression. To evaluate the effect of Lodamin on T cell differentiation into Th1 and Th17, T cells were cultured in several conditions in the presence of Lodamin. FIG. 21 shows the effects of Lodamin on T cell differentiation as analyzed by intracellular cytokine staining. Whole splenocytes were stimulated with soluble anti-CD3 (1 μg/ml) in each of the three conditions for 72 h: Th0 condition: anti-IFNγ Ab (1 μg/ml), anti-IL-4 Ab (1 μg/ml); Th1 condition: IL-12 (10 ng/ml), anti-IL-4 Ab (1 μg/ml); Th17 condition: TGFβ1 (2 ng/ml), IL-6 (20 ng/ml), anti-IFNγ Ab (1 μg/ml), anti-IL-4 Ab (1 μg/ml) in the presence of vehicle (control, no Lodamin), Lodamin 1.0 nM, and Lodamin 10 nM as indicated. Lodamin inhibit the differentiation of T cells from splenocytes into Th1/Th17.

Figure 22A:
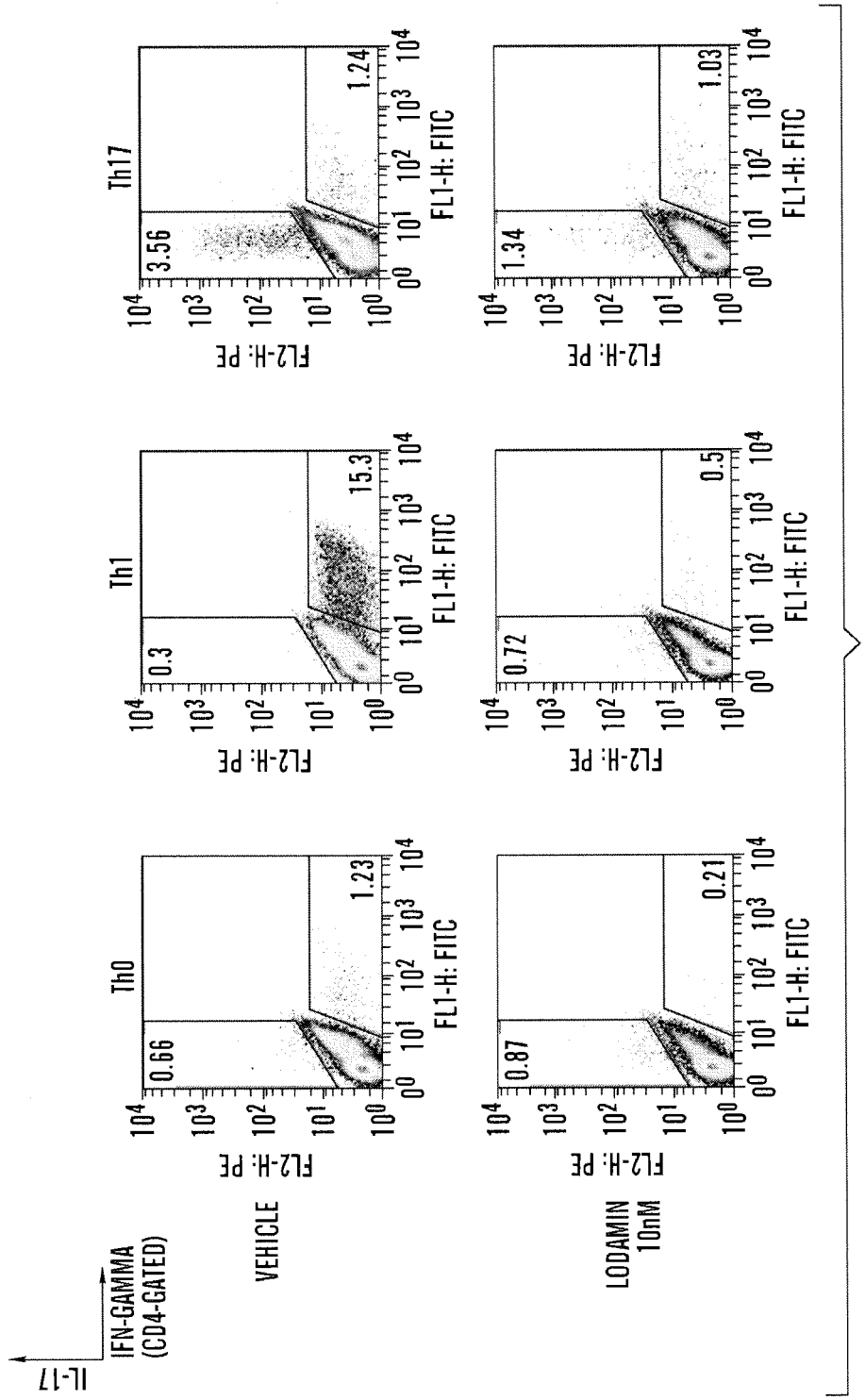
FIG. 22A shows the effects of Lodamin on T cell differenianion without antigen presenting cells (APC) as analyzed by intracellular cytokine staining. Purified CD4+ CD25− T cells were stimulated with plate-bound anti-CD3 (5 µg/ml) and soluble anti-CD28 (0.5 µg/ml) under the following conditions for 72 h: Th0 condition: anti-IFNγ Ab (1 µg/ml), anti-IL-4 Ab (1 µg/ml); Th1 condition: IL-12 (10 ng/ml), anti-IL-4 Ab (1 µg/ml); Th17 condition: TGFβ1 (2 ng/ml), IL-6 (20 ng/ml), anti-IFNγ Ab (1 µg/ml), anti-IL-4 Ab (1 µg/ml) in the presence of vehicle (control, no Lodamin), Lodamin 1.0 nM, and Lodamin 10 nM as indicated. Expansion of Th1/Th17 cells was evaluated by intracellular cytokine staining.

To further expand and study the effect of Lodamin in suppressing T cell differentiation, intracellular cytokine staining was performed. FIG. 22A shows the effects of Lodamin on T cell differentiation without antigen presenting cells (APC) as analyzed by intracellular cytokine staining. Purified $CD4^+CD25^-$ T cells (not activated Th effector cells) were stimulated with plate-bound anti-CD3 (5 μg/ml) and soluble anti-CD28 (0.5 μg/ml) with each conditions for 72 h: Th0 condition: anti-IFNγ Ab (1 μg/ml), anti-IL-4 Ab (1 μg/ml); Th1 condition: IL-12 (10 ng/ml), anti-IL-4 Ab (1 μg/ml); Th17 condition: TGFβ1 (2 ng/ml), IL-6 (20 ng/ml), anti-IFNγ Ab (1 μg/ml), anti-IL-4 Ab (1 μg/ml) in the presence of vehicle (control, no Lodamin), Lodamin 1.0 nM, and Lodamin 10 nM as indicated. The intracellular cytokine staining and FACS analysis show that Lodamin significantly reduces IL-17.

Figures 22B, 22C:
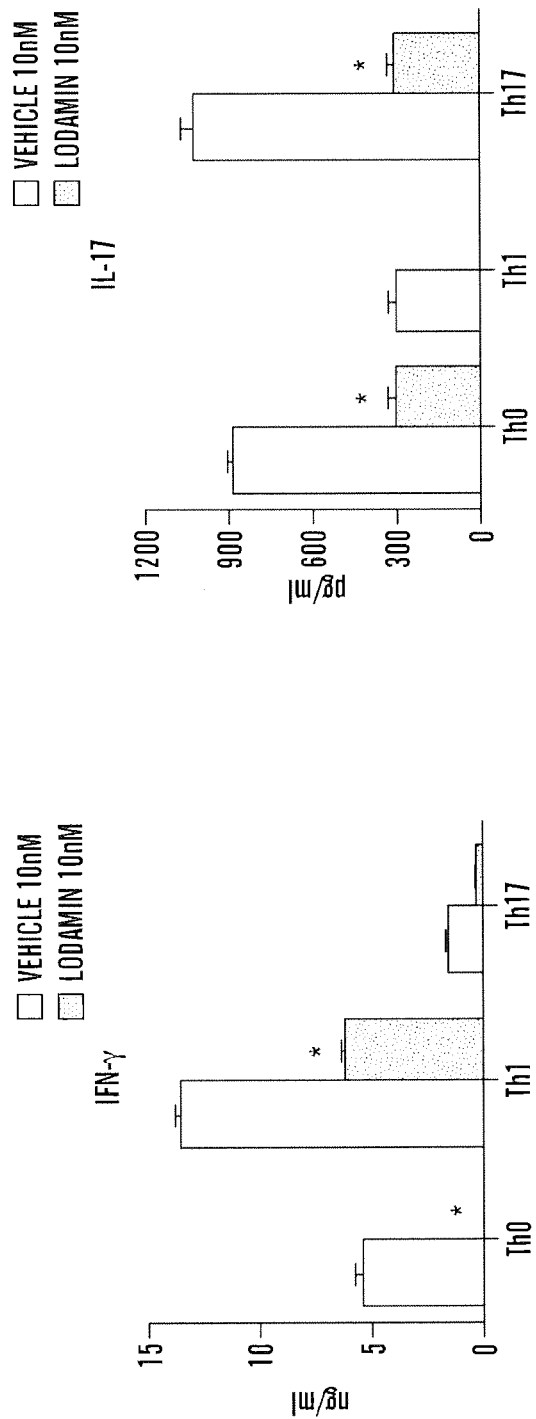
FIG. 22B shows the effects of Lodamin on IFN-γ production in CD4+CD25− T cells stimulated with plate-bound anti-CD3 (5 µg/ml) and soluble anti-CD28 (0.5 µg/ml) as analyzed by ELISA. The conditions for Th0, Th1 and Th17 were the same as for FIG. 22A.
FIG. 22C shows the effects of Lodamin on IL-17 production in CD4+CD25-T cells stimulated with plate-bound anti-CD3 (5 µg/ml) and soluble anti-CD28 (0.5 µg/ml) as analyzed by ELISA. The conditions for Th0, Th1 and Th17 were the same as for FIG. 22A.

The effect of Lodamin on the production of Th0 and Th17 cytokines from T cells was evaluated using ELISA. FIG. 22B shows the effects of Lodamin on IFN-γ production in $CD4^+CD25^-$ T cells (T effector cells) stimulated with plate-bound anti-CD3 (5 μg/ml) and soluble anti-CD28 (0.5 μg/ml) as analyzed by ELISA. The conditions for Th0, Th1 and Th17 were same as FIG. 22A. These data indicate that Lodamin significantly inhibited or reduced IFN-γ production in all three cells: Th0, Th1 and Th17.

Lodamin also had a similar inhibitory action on IL-17 production in Th0, Th1 and Th17 cells. FIG. 22C shows the effects of Lodamin on IL-17 production in $CD4^+CD25^-$ T cells stimulated with plate-bound anti-CD3 (5 μg/ml) and soluble anti-CD28 (0.5 μg/ml) as analyzed by ELISA. The conditions for Th0, Th1 and Th17 were same as FIG. 22A. These data indicate that Lodamin significantly inhibited or reduced IL-17 production in all three cells: Th0, Th1 and Th17.

Based on the fact that T cells can uptake Lodamin, and the effects of Lodamin on T cell activation and proliferation, the suppression of T cell differentiation and of cytokine production, the inventors tested whether Lodamin has anti-inflammatory effect. To elucidate these effect for T cells, cytokine production by anti-CD3 stimulated $CD4^+$ T cells were analyzed. FIG. 23A shows the effects of increasing amounts of Lodamin on IFN-γ production in $CD4^+$ T cells stimulated with plate-bound anti-CD3 (1 μg/ml) for three days as analyzed by ELISA. FIG. 23B shows the effects of increasing amounts of Lodamin on IL-17 production in $CD4^+$ T cells stimulated with plate-bound anti-CD3 (1 μg/ml) for three days as analyzed by ELISA. These data show that Lodamin significantly inhibited or reduced IFN-γ and IL-17 cytokine production, indicating that Lodamin has anti-inflammatory effect by way of inhibiton of cytokine production. IFN-γ and IL-17 cytokines are chosen as representative cytokines known to be associated with inflammation.

As previous studies demonstrated that Th17 cells are the dominant pathogenic cellular component in autoimmune inflammatory diseases. Here, the inventors found that Lodamin modulates Th17 differentiation. The inventors further investigated the anti-inflammatory effect of Lodamin using animal model of ocular autoimmune disease. FIG. 24 shows the use of oral administration of Lodamin to ameliorate experimental autoimmune uveoretinitis (EAU). EAU was induced by immunizing C57BL/6 mice with human interphotoreceptor retinoid-binding protein (IRBP) 1-20. Lodamin at a dose of 30 mg/kg, or vehicle was orally administrated every other day after immunization. EAU severity was evaluated clinically and histopathologically on day 21.

To understand the mechanism of the suppressive effect in Lodamin-administered mice, antigen-specific IFN-γ/IL-17 production from regional lymph node cells were analyzed. FIGS. 25A and 25B show the suppression of antigen-specific cytokine production by lymph nodes from Lodamin administered EAU mice. On day 21 after immunization, draining lymph node cells were harvested and IRBP-specific IFN-γ (FIG. 25A) and IL-17 (FIG. 25B) production was analyzed by ELISA.

One possible mechanism of action of Lodamin is that Lodamin affect the expansion regulatory T cells, resulting in a reduction of Th1/Th17 development and thus, disease progression. Foxp3 have been widely known as indispensable transcription factor for regulatory T cells. To exclude the possibility of described above, Foxp3 expression in regional lymph node cells were analyzed. FIG. 26 shows the Foxp3 expression, as a representative marker for regulatory T cells, by draining lymph node cells from Lodamin administered EAU mice (n=5). On day 21 after immunization, draining lymph node cells were harvested and cell surface was stained with APC-labeled anti-CD4 antibody, followed by intracellular Foxp3 staining.

Figure 27:
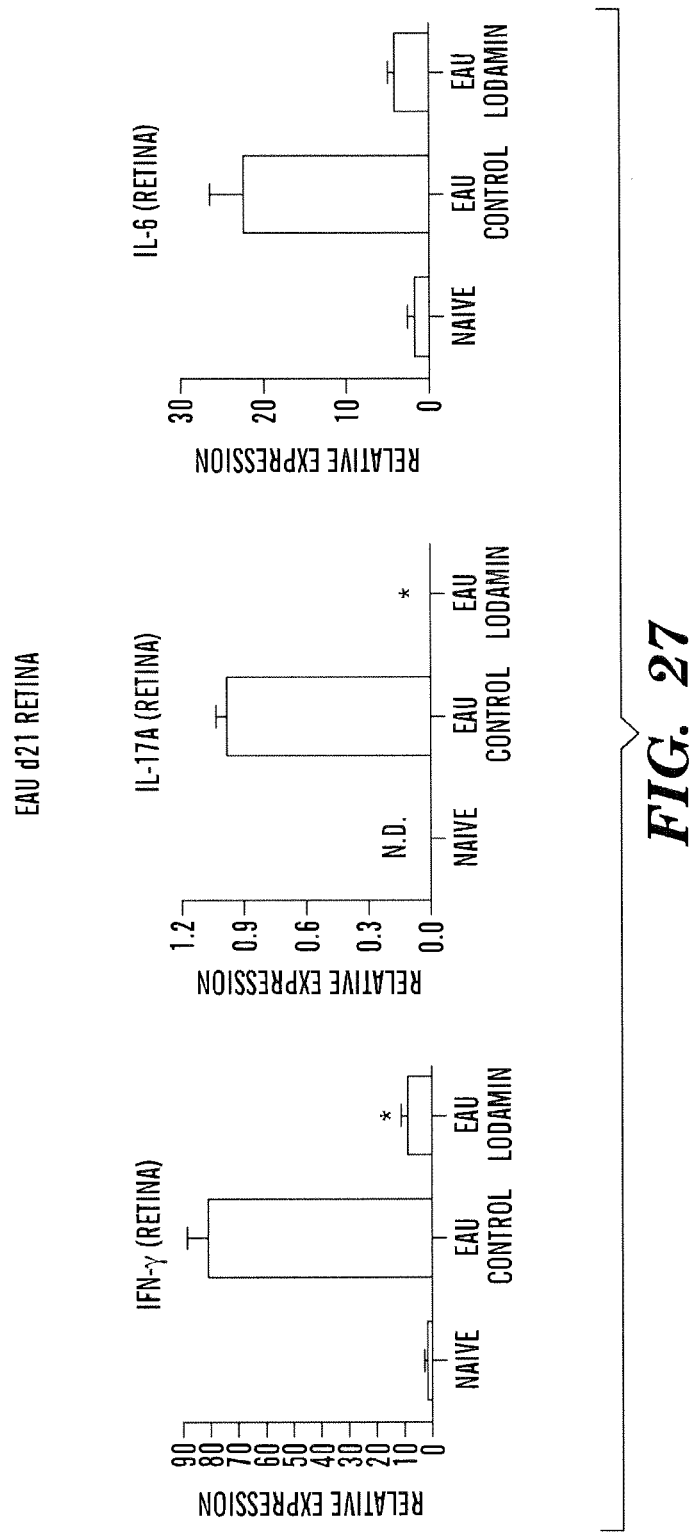
FIG. 27 shows the suppression of intraocular cytokine expression of IFN-γ, IL-17A and IL-6 from Lodamin administered EAU mice (n=3). On day 21, mRNA from retinas was isolated for quantitative real-time PCR (qPCR). qPCR for indicated cytokines were performed.

To elucidate the local (eye) inflammatory milieu, retinas were subjected to polymerase chain reaction (PCR). FIG. 27 shows the suppression of intraocular cytokine expression of IFN-γ, IL-17A and IL-6 from Lodamin administered EAU mice (n=3). On day 21, mRNA from retinas was isolated for quantitative real-time PCR (qPCR). qPCR for indicated cytokines were performed.

The references cited herein and throughout the application are incorporated herein by reference.

Although the foregoing invention has been described in some detail by way of illustration and example for the purposes of clarity of understanding, one skilled in the art will easily ascertain that certain changes and modifications may be practiced without departing from the spirit and scope of the appended claims.

REFERENCES

1. Holmgren, L., O'Reilly, M. & Folkman, J. Dormancy of micrometastases: balanced proliferation and apoptosis in the presence of angiogenesis suppression. Nat. Med. 1, 149-153 (1995).
2. Naumov, G., Folkman, J. Strategies to prolong the nonangiogenic dormant state of human cancer. in Antiangiogenic cancer therapy, Edn. 1. (ed. W. Darren, Herbst, R S, Abbruzzese, J L.) 3-23 (CRS press, Taylor and Francis group, 2007).
3. Ingber, D. et al. Synthetic analogue of fumagillin that inhibit angiogenesis and suppress tumour growth. Nature 348, 555-557 (1990).
4. Folkman, J., Kalluri, R. Tumor angiogenesis. in Cancer Medicine Vol. 1. (ed. D. Kufe, Pollock, R E., Weischselbaum, R R., Bast, R C., Gansler, T S., Holland, J F., Frei, E.) 161-194 (Hamilton, Ontario: BC Decker Inc, 2003).
5. Yamaoka, M., Yamamoto, T., Ikeyama, S., Sudo, K., Fujita, T. Angiogenesis inhibitor TNP-470 (AGM-1470) potently inhibits the tumor growth of hormone-independent human breast and prostate carcinoma cell lines. Cancer Res. 53, 5233-5236 (1993).
6. Shusterman, S., Grupp, S A., Barr, R., Carpentieri, D., Zhao, H., Maris, J M. The angiogenesis inhibitor tnp-470 effectively inhibits human neuroblastoma xenograft growth, especially in the setting of subclinical disease. Clin. Cancer Res. 7, 977-984 (2001).
7. Yanase, T., Tamura, M., Fujita, K., Kodama, S., Tanaka, K. Inhibitory effect of angiogenesis inhibitor TNP-470 on tumor growth and metastasis of human cell lines in vitro and in vivo. Cancer Res. 53, 2566-2570 (1993).
8. Takamiya, Y., Brem, H., Ojeifo, J., Mineta, T. & Martuza, R. AGM-1470 inhibits the growth of human glioblastoma cells in vitro and in vivo. Neurosurgery 34, 869-875 (1994).
9. Takamiya, Y., Friedlander, R M., Brem, H., Malick, A., Martuza, R L Inhibition of angiogenesis and growth of human nerve-sheath tumors by AGM-1470. J Neurosurg 78, 470-476 (1993).
10. Emoto, M., Tachibana, K., Iwasaki, H., Kawarabayashi, T. Antitumor effect of TNP-470, an angiogenesis inhibitor, combined with ultrasound irradiation for human uterine sarcoma xenografts evaluated using contrast color Doppler ultrasound. Cancer Sci. 98, 929-935 (2007).
11. Nahari, D. et al. Tumor cytotoxicity and endothelial Rac inhibition induced by TNP-470 in anaplastic thyroid cancer. Mol. Cancer Ther. 6, 1329-1337 (2007).
12. Kanamori, M., Yasuda, T., Ohmori, K., Nogami, S., Aoki, M. Genetic analysis of high-metastatic clone of RCT sarcoma in mice, and its growth regression in vivo in response to angiogenesis inhibitor TNP-470. J. Exp. Clin. Cancer Res. 26, 101-107 (2007).
13. Sin, N., Meng, L., Wang, M Q., Wen, J J., Bornmann, W G., Crews, C M. The anti-angiogenic agent fumagillin covalently binds and inhibits the methionine aminopeptidase, MetAP-2. Proc. Natl. Acad. Sci. USA 94, 6099-6103 (1997).
14. Zhang, Y., Griffith, E., Sage, J., Jacks, T. & Liu, J. Cell cycle inhibition by the anti-angiogenic agent TNP-470 is mediated by p53 and p21WAF1/CIP1. Proc Natl. Acad. Sci. USA 97, 6427-6432 (2000).
15. Mauriz, J. et al. Cell-cycle inhibition by TNP-470 in an in vivo model of hepatocarcinoma is mediated by a p53 and p21WAF1/CIP1 mechanism. Transl. Res. 149, 46-53 (2007).
16. Kruger, E., Figg, W D. TNP-470: an angiogenesis inhibitor in clinical development for cancer. Expert. Opin. Investig. Drugs 9, 1383-1396 (2000).
17. Kudelka, A., Verschraegen, C. & Loyer, E. Complete remission of metastatic cervical cancer with the angiogenesis inhibitor TNP-470. N. Engl. J. Med. 338, 991-992 (1998).
18. Tran, H. et al. Clinical and pharmacokinetic study of TNP-470, an angiogenesis inhibitor, in combination with paclitaxel and carboplatin in patients with solid tumors. Cancer Chemother. Pharmacol. 54, 308-314 (2004).
19. Kudelka, A. et al. A phase I study of TNP-470 administered to patients with advanced squamous cell cancer of the cervix. Clin. Cancer Res. 3, 1501-1505 (1997).
20. Herbst, R. et al. Safety and pharmacokinetic effects of TNP-470, an angiogenesis inhibitor, combined with paclitaxel in patients with solid tumors: evidence for activity in non-small-cell lung cancer. J. Clin. Oncol. 20, 4440-4447 (2002).
21. Stadler, W., Kuzel, T., Shapiro, C., Sosman, J., Clark, J., Vogelzang, N J. Multi-institutional study of the angiogenesis inhibitor TNP-470 in metastatic renal carcinoma. J. Clin. Oncol. 17, 2541-2545 (1999).
22. Logothetis, C. et al. Phase I trial of the angiogenesis inhibitor TNP-470 for progressive androgen-independent prostate cancer. Clin. Cancer Res. 7, 1198-1203 (2001).

23. Bhargava, P. et al. A phase I and pharmacokinetic study of TNP-470 administered weekly to patients with advanced cancer *Clin. Cancer Res.* 5, 1989-1995 (1999).
24. Satchi-Fainaro, R. et al. Targeting angiogenesis with a conjugate of HPMA copolymer and TNP-470. *Nat Med* 10, 255-261 (2004).
25. Cretton-Scott, E., Placidi, L., McClure, H., Anderson, D. & Sommadossi, J. Pharmacokinetics and metabolism of O-(chloroacetyl-carbamoyl) fumagillol (TNP-470, AGM-1470) in rhesus monkeys. *Cancer Chemother. Pharmacol.* 38, 117-122 (1996).
26. Kataoka, K., Harada, A., Nagasaki, Y. Block copolymer micelles for drug delivery: design, characterization and biological significance. *Adv. Drug Deliv. Rev.* 47, 113-131 (2001).
27. Harris, J. & Chess, R. Effect of pegylation on pharmaceuticals. *Nat. Rev. Drug Discov.* 2, 214-221 (2003).
28. Edlund, U. & Albertsson, A. Degradable polymer microspheres for controlled drug delivery. *Adv. Polym. Sci.* 157, 67-112 (2001).
29. Rogers, M., Birsner, A. & D'Amato, R. The mouse cornea micropocket angiogenesis assay. *Nat. Protoc.* 2, 2545-2550 (2007).
30. Antoine, N. et al. AGM-1470, a potent angiogenesis inhibitor, prevents the entry of normal but not transformed endothelial cells into the G1 phase of the cell cycle. Cancer Res 54, 2073-6 (1994).
31. Folkman, J. Tumor angiogenesis. in Accomplishments in cancer research (eds. Wells, S. J. & Sharp, P.) 32-44 (Lippincott Williams & Wilkins, New York, 1998).
32. Folkman, J. Tumor angiogenesis. in Cancer Medicine (eds. Holland, J. et al.) 132-152 (B. C. Decker Inc., Ontario, Canada, 2000).
33. Folkman, J., Klement, G. Platelet biomarkers for the detection of disease. *US and International Patent* 20060204951 (2006).
34. Kim, E. S. & Herbst, R. S. Angiogenesis inhibitors in lung cancer. Curr Oncol Rep 4, 325-33 (2002).
35. Kwon, Y. Handbook of Essential Pharmacokinetics, Pharmacodynamics and Drug Metabolism for Industrial Scientists. (Plenum Pub New York; 2001).
36. Pierri, E. & Avgoustakis, K. Poly(lactide)-poly(ethylene glycol) micelles as a carrier for griseofulvin. *J. Biomed. Mater. Res. A* 75, 639-647 (2005).
37. Kakizawa, Y., Kataoka, K. Block copolymer micelles for delivery of gene and related compounds. *Adv. Drug Deliv. Rev.* 54, 203-222 (2002).
38. Torchilin, V. Targeted polymeric micelles for delivery of poorly soluble drugs. *Cell. Mol. Life Sci.* 61, 2549-2559 (2004).
39. Nishiyama, N., Kataoka, K. Current state, achievements, and future prospects of polymeric micelles as nanocarriers for drug and gene delivery. *Pharmacol. Ther.* 112, 630-648 (2006).
40. Duncan, R. Polymer conjugates as anticancer nanomedicines. Nat. Rev. Cancer 6, 688-701 (2006).
41. Bernier, S. G., Westlin, W. F. & Hannig, G., Fumagillin class inhibitors of methionine aminopetidase-2. *Drugs of the Future* 30, 497-508 (2005).
42. Lui, S., Widom, J., Kemp, C. W., Crews, C. M., & Clardy, J., Structure of human methionine aminopeptidase-2 complexed with fumagillin. Science 282, 1324-1327 (1998).
43. Wang et al., Tumor suppression by a rationally designed reversible inhibitor of methionine aminopeptidase-2. Cancer Res. 63, 7861-7869 (2003).
44. Bainbridge et al., Arthritis Res. and Therapy, vol. 9, No. 6.
45. Wang et al., Correlation of tumor growth suppression and methionine aminopetidase-2 activity blockade using an orally active inhibitor, Proc. Natl. Acad. Sci. U.S.A., 105, 1838-1843 (2008).
46. Roskoski, Src protein—tyrosine kinase structure and regulation, Biochemical and Biophysical Research Communications 324 (2004) 1155-1164
47. Tucker, et al., Ectopic expression of methionine aminopeptidase-2 causes cell transformation and stimulates proliferation; Oncogene (2008), 1-10.

The invention claimed is:

1. A method of treating an autoimmune disease in a subject in need thereof, the method comprising administering a formulation comprising micelles comprised of a fumagillol derivative having anti-inflammation activity, wherein the fumagillol derivative is covalently associated with a block copolymer comprising a hydrophilic polymer moiety and a hydrophobic polymer moiety, and wherein the hydrophilic polymer moiety is a poly(ethylene glycol) (PEG) polymer and the hydrophobic polymer moiety of said block copolymer is selected from the group consisting of poly(L-lysine), poly(aspartic acid), polyglycolic acid (PGA), poly (D, L-lactic co-glycolic acid) (PLGA), poly(valerolactone), poly(hydroxybutyrate), poly(hydroxyvalerate), poly(caprolactone) (PCL), and poly(propylene oxide).

2. The method of claim 1, wherein said fumagillol derivative is covalently linked to the hydrophobic moiety of said block copolymer.

3. The method of claim 1, wherein said fumagillol derivative comprises a derivative selected from the group consisting of 6-O—(N-chloroacetylcarbamoyl) fumagillol (TNP-470), 6-O-(4-methoxyaniline)acetyl fumagillol; 6-O-(3,4, 5-trimethexyaniline)acetyl fumagillol; 6-O-(4-(N,N-dimethylethoxy) aniline)acetyl fumagillol; 6-O-(cyclopropylamino) acetyl fumagillol; 6-O-(cyclobutylamino)acetyl fumagillol; 4-((cyclopropylamino)acetyl) oxy-2-(1,2-epoxy-1,5 20 dimethyl-4-hexenyl)-3-methoxy-1-chloromethyl-1 cyclohexanol; and 4-((cyclobutylamino)acetyl) oxy-2-(1,2-epoxy-1,5 dimethyl-4-hexenyl)-3-methoxy-1-chloromethyl-1-cyclohexanol.

4. The method of claim 1, wherein the autoimmune disease results in inflammation of the eye.

5. A method of treating uveitis in a subject in need thereof, the method comprising administering a formulation comprising micelles composed of a fumagillol derivative having anti-proliferation activity and anti-inflammation activity, wherein the fumagillol derivative is covalently associated with a block copolymer comprising a hydrophilic polymer moiety and a hydrophobic polymer moiety, and wherein the hydrophilic polymer moiety is a poly(ethylene glycol) (PEG) polymer and the hydrophobic polymer moiety of said block copolymer is selected from the group consisting of poly(L-lysine), poly(aspartic acid), polyglycolic acid (PGA), poly(D, L-lactic co-glycolic acid) (PLGA), poly (valerolactone), poly(hydroxybutyrate), poly(hydroxyvalerate), poly(caprolactone) (PCL), and poly(propylene oxide).

6. The method of claim 5, wherein said fumagillol derivative is covalently linked to the hydrophobic moiety of said block copolymer.

7. The method of claim 5, wherein said fumagillol derivative comprises a derivative selected from the group consisting of 6-O—(N-chloroacetylcarbamoyl) fumagillol (TNP-470), 6-O-(4-methoxyaniline)acetyl fumagillol; 6-O-(3,4, 5-trimethexyaniline)acetyl fumagillol; 6-O-(4-(N,N-dimethylethoxy) aniline)acetyl fumagillol; 6-O-(cyclopropylamino) acetyl fumagillol; 6-O-(cyclobutylamino)acetyl fumagillol; 4-((cyclopropylamino)acetyl) oxy-2-(1,2-epoxy-1,5 dimethyl-4-hexenyl)-3-methoxy-1-chloromethyl-1 cyclohexanol; and 4-((cyclobutylamino)acetyl) oxy-2-(1,2-epoxy-1,5 dimethyl-4-hexenyl)-3-methoxy-1-chloromethyl-1-cyclohexanol.

* * * * *

UNITED STATES PATENT AND TRADEMARK OFFICE
CERTIFICATE OF CORRECTION

PATENT NO. : 9,782,489 B2
APPLICATION NO. : 15/248043
DATED : October 10, 2017
INVENTOR(S) : Ofra Benny-Ratsaby et al.

Page 1 of 1

It is certified that error appears in the above-identified patent and that said Letters Patent is hereby corrected as shown below:

In the Specification

At Column 1, Lines 22-25, please delete:
"This invention was made with Government support under Grant No.: W81XWH-05-1-0115 awarded by the Department of Defense. The Government has certain rights in the invention."
And insert the following text:
-- This invention was made with government support under grant number W81XWH-05-1-0115 awarded by the U.S. Department of the Army. The Government has certain rights in the invention. --

Signed and Sealed this
Twenty-fourth Day of July, 2018

Andrei Iancu
*Director of the United States Patent and Trademark Office*